United States Patent
Watanabe et al.

(10) Patent No.: US 11,299,485 B2
(45) Date of Patent: Apr. 12, 2022

(54) THIOPHENE DERIVATIVE AND USE THEREOF

(71) Applicant: FUJIMOTO CO., LTD., Matsubara (JP)

(72) Inventors: Mayumi Watanabe, Matsubara (JP); Takashi Ando, Matsubara (JP); Yasuyuki Ueda, Matsubara (JP); Kenya Matsushita, Matsubara (JP); Yasuhiko Mizutani, Matsubara (JP); Jun Takahashi, Matsubara (JP); Mitsuo Yamada, Matsubara (JP); Hironori Yokoyama, Matsubara (JP); Daiki Kanaoka, Matsubara (JP); Kazunori Urabe, Matsubara (JP); Takafumi Ishii, Matsubara (JP)

(73) Assignee: FUJIMOTO CO., LTD., Matsubara (JP)

( * ) Notice: Subject to any disclaimer, the term of this patent is extended or adjusted under 35 U.S.C. 154(b) by 1 day.

(21) Appl. No.: 16/962,218

(22) PCT Filed: Jan. 25, 2019

(86) PCT No.: PCT/JP2019/002596
§ 371 (c)(1),
(2) Date: Jul. 14, 2020

(87) PCT Pub. No.: WO2019/146773
PCT Pub. Date: Aug. 1, 2019

(65) Prior Publication Data
US 2021/0061795 A1 Mar. 4, 2021

(30) Foreign Application Priority Data

Jan. 25, 2018 (JP) .............................. JP2018-010984
Apr. 25, 2018 (JP) .............................. JP2018-084202

(51) Int. Cl.
| | | |
|---|---|---|
| *C07D 409/14* | (2006.01) | |
| *C07D 413/14* | (2006.01) | |
| *A61P 35/00* | (2006.01) | |
| *A61P 29/00* | (2006.01) | |
| *A61P 37/02* | (2006.01) | |
| *A61P 43/00* | (2006.01) | |
| *A61P 37/00* | (2006.01) | |
| *A61K 31/454* | (2006.01) | |
| *A61K 31/4545* | (2006.01) | |
| *A61K 31/5377* | (2006.01) | |
| *A61P 35/02* | (2006.01) | |

(52) U.S. Cl.
CPC ............ *C07D 409/14* (2013.01); *A61P 35/00* (2018.01); *A61P 35/02* (2018.01)

(58) Field of Classification Search
CPC .. C07D 409/14; C07D 495/04; C07D 413/14; A61P 35/02; A61P 35/00; A61P 29/00; A61P 37/02; A61P 43/00; A61P 37/00; A61K 31/454; A61K 31/4545; A61K 31/5377

See application file for complete search history.

(56) References Cited

U.S. PATENT DOCUMENTS

| | | |
|---|---|---|
| 2003/0013712 A1 | 1/2003 | Tullis et al. |
| 2003/0032803 A1 | 2/2003 | Duan et al. |
| 2003/0045552 A1 | 3/2003 | Robarge et al. |
| 2008/0176900 A1 | 7/2008 | Zhang |
| 2011/0196150 A1 | 8/2011 | Man et al. |

FOREIGN PATENT DOCUMENTS

| | | |
|---|---|---|
| JP | 2002-541138 A | 12/2002 |
| JP | 2004-525889 A | 8/2004 |
| JP | 2004-528351 A | 9/2004 |
| JP | 2009-509945 A | 3/2009 |
| JP | 2012-524071 A | 10/2012 |
| WO | WO 2010/121140 A1 | 10/2010 |
| WO | WO 2011/100380 A1 | 8/2011 |

(Continued)

OTHER PUBLICATIONS

Mansfield, J. C., "A randomized, double-blind, placebo-controlled trial of lenalidomide in the treatment of moderately severe active Crohn's disease." Alimentary pharmacology & therapeutics 26.3 (2007): 421-430.*
European Medicines Agency Annex I 2012: 1-98.*
Awan, F.T., "Thalidomide and lenalidomide as new therapeutics for the treatment of chronic lymphocytic leukemia." Leukemia & lymphoma 51.1 (2010): 27-38.*
Verweij, M., 2000 Preventive Medicine Between Obligation and Aspiration 2000, Springer Science and Business Media p. 1-190; Ch. 3; 31 p.*

(Continued)

*Primary Examiner* — John M Mauro
(74) *Attorney, Agent, or Firm* — Leydig, Voit & Mayer, Ltd.

(57) ABSTRACT

The present invention relates to thiophene derivatives represented by the following formula (I):

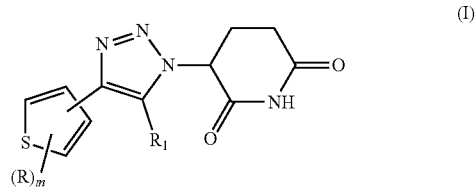

wherein each symbol is as defined in the DESCRIPTION, or a salt thereof, which has TNF-α production suppressive activity and hematologic cancer cell proliferation inhibitory activity, and is useful for the treatment of rheumatoid arthritis, Crohn's disease, ulcerative colitis, and further, hematologic cancer.

25 Claims, No Drawings

(56) References Cited

FOREIGN PATENT DOCUMENTS

| WO | WO 2017/197051 A1 | 11/2017 |
|----|-------------------|---------|
| WO | WO 2018/011093 A1 | 1/2018  |

OTHER PUBLICATIONS

Eitan, E., "Combination therapy with lenalidomide and nanoceria ameliorates CNS autoimmunity." Experimental neurology 273 (2015): 151-160.*

Lopez-Millan, B., "Therapeutic effect of the immunomodulatory drug lenalidomide, but not pomalidomide, in experimental models of rheumatoid arthritis and inflammatory bowel disease." Experimental & molecular medicine 49.2 (2017): e290:1-10.*

Arora et al., "A comprehensive review of lenalidomide in B-cell non-Hodgkin lymphoma," *Ther. Adv. Hematol.*, 7(4): 209-221 (2016).

Chou, "Monoclonal Antibody," *Internal Medicine*, 120(4): 887-892 (2017).

Gemechu et al., "Humanized cereblon mice revealed two distinct therapeutic pathways of immunomodulatory drugs," *Proc. Natl. Acad. Sci. U.S.A.*, 115(46): 11802-11807 and Supplementary Information (2018).

Leitans et al., "Efficient Expression and Crystallization System of Cancer-Associated Carbonic Anhydrase Isoform IX," *J. Med. Chem.*, 58(22): 9004-9009 (2015).

National Comprehensive Cancer Network (NCCN), "Non-Hodgkin's Lymphomas," NCCN Clinical Practice Guidelines in Oncology (NCCN Guidelines), $2^{nd}$ Version (2015).

Ronnebaum et al., "Synthesis of 1,2,3-triazole 'click' analogues of thalidomide," *Tetrahedron*, 72(40): 6136-6141 (2016).

Shibayama, "Proteasome inhibitor," *Internal Medicine*, 120(4): 881-886 (2017).

Suzumiya et al., "Advances in the practice of malignant lymphoma: Recommendations for lymphomatology," *The Journal of the Japanese Society of Internal Medicine*, 105(9): 1761-1767 (2016).

Terui, "Immunomodulator," *Internal Medicine*, 120(4): 875-880 (2017).

Yamazaki, "Secretory mechanism and artificial control of TNF-α," *Clinical Immunology*, 27(10): 1270-1274 (1995).

Japanese Patent Office, International Search Report in International Patent Application No. PCT/JP2019/002596 (dated Feb. 26, 2019).

Chan et al., "Therapeutic antibodies for autoimmunity and inflammation," *Nat. Rev. Immunol.*, 10(5): 301-316 (2010).

Jang et al., "The Role of Tumor Necrosis Factor Alpha (TNF-α) in Autoimmune Disease and Current TNF-αInhibitors in Therapeutics," *Int. J. Mol. Sci.*, 22(5): 2719 (2021).

\* cited by examiner

THIOPHENE DERIVATIVE AND USE THEREOF

CROSS-REFERENCE TO RELATED APPLICATIONS

This patent application is the U.S. national phase of International Patent Application No. PCT/JP2019/002596, filed on Jan. 25, 2019, which claims the benefit of Japanese Patent Application No. 2018-010984 filed on Jan. 25, 2018, and Japanese Patent Application No. 2018-084202 filed on Apr. 25, 2018, which are incorporated by reference in their entireties herein.

TECHNICAL FIELD

The present invention relates to a pharmaceutical field, in particular, novel thiophene derivatives having a TNF-α production suppressive activity and a hematologic cancer cell growth inhibitory activity.

BACKGROUND ART

Tumor necrosis factor-α(TNF-α) is an inflammatory cytokine released by cells of the immune system. It is known that continuous and excessive production of TNF-α causes tissue injury and various diseases (non-patent document 1). Examples of pathological conditions involving TNF-α include many pathological conditions including autoimmune diseases such as rheumatoid arthritis, Crohn's disease, and ulcerative colitis.

Given the above, compounds that suppress production of TNF-α are expected to be effective in the treatment of the above-mentioned diseases, and various studies have been performed.

The therapeutic agents for rheumatoid arthritis, which is a representative autoimmune disease, are roughly classified into the following three.

The first therapeutic agents are anti-inflammatory agents. Anti-inflammatory agents have an action to reduce the pain and swelling in inflammation. Furthermore, the anti-inflammatory agents are classified into non-steroidal anti-inflammatory agents (NSAID) and steroids. Examples of the NSAID include celecoxib, loxoprofen, indomethacin and the like. While these agents immediately relieve swelling and pain due to inflammation, they have a weak suppressive effect on the progression of rheumatism. On the other hand, steroids strongly suppress inflammation and are effective for pain, swelling, and stiffness. However, long-term use of a high dose of steroids may pose a problem of causing opportunistic infection, osteoporosis or arteriosclerosis.

The second therapeutic agents are disease-modifying anti-rheumatic drugs (DMARDs). DMARDs act directly on immune disorders, suppress inflammation, and suppress progression of diseases. On the other hand, problems occur such as the absence of a method for predicting the efficacy, slow onset of action, and high frequency of side effects, even though the efficacy strength varies greatly among individuals.

The third therapeutic agents are biologics. A plurality of biologics are on the market, such as infliximab sold as REMICADE (registered trademark) and etanercept sold as ENBREL (registered trademark). (patent document 1). Biologics show strong efficacy, but are problematically very expensive. In recent years, JAK inhibitors such as tofacitinib sold as XELJANZ (registered trademark), which is a small-molecule-compound have been put on the market and are attracting attention because they show effectiveness comparable to that of biologics. However, there is a problem that the risk of serious infection increases in a dose-dependent manner, and the like. Therefore, the development of a novel anti-rheumatic drug which can be administered orally and has an effect comparable to that of biologics is expected.

Hematologic cancer is a disease caused by the canceration of blood cells, such as red blood cells, white blood cells, and platelets, in the process of differentiation. Among the hematologic cancers, multiple myeloma, malignant lymphoma and leukemia, which have a particularly large number of patients, are called three major hematologic cancers.

Multiple myeloma is a disease caused by canceration of plasma cells that have differentiated and matured from B cells which are white blood cells, one of blood cells. In the drug treatment of multiple myeloma, the introduction of proteasome inhibitors (bortezomib, carfilzomib, ixazomib) and immunomodulators (thalidomide, lenalidomide, pomalidomide) has dramatically improved the prognosis and enabled long-term survival (non-patent documents 2, 3). However, multiple myeloma is not a disease that can be expected to be cured, and its main therapeutic purpose is to extend the survival period while maintaining the QOL of recurrent patients. In addition, it has been clarified that the prognosis is further improved by the two antibody drugs (erotuzumab, daratumumab) developed in recent years; however, exacerbation of the disease state has not been prevented completely (non-patent document 4).

Malignant lymphoma is a disease caused by canceration of lymphocytes which are white blood cells, one of blood cells. Chemotherapy still occupies the core of drug treatment for malignant lymphoma. Even though it is a hematological tumor that can be cured, the cure rate varies greatly depending on the disease type, and some malignant lymphomas are difficult to treat with chemotherapy (non-patent document 5). For cases where a sufficient therapeutic effect cannot be obtained by chemotherapy, a molecular targeting drug alone or combined with a chemotherapeutic agent has been tried. For example, in B-cell non-Hodgkin's lymphoma, which has a CD20-positive rate of 90% or more, the combined use of an anti-CD20 antibody drug rituximab and other drug has become the mainstream. As a concrete example, combined use therapy of rituximab and chemotherapy (e.g., CHOP therapy) is recommended for patients with newly diagnosed of diffuse large B-cell lymphoma, mantle cell lymphoma, or follicular lymphoma, and rituximab is positioned as a superior molecular targeting drug (non-patent document 6).

Other molecular targeting drugs for B-cell non-Hodgkin's lymphoma that are attracting attention include ibrutinib, which is a Bruton's Tyrosine Kinase (BTK) inhibitor, and lenalidomide, which is an immunomodulator. Particularly, lenalidomide improves the prognosis of patients with non-germinal center B cell (GCB) type diffuse large B-cell lymphoma, but is less effective against GCB type diffuse large B-cell lymphoma, moreover, in a combined use test with rituximab targeting recurrent mantle cell lymphoma patients, the overall response rate was 56% with 44% of non-responsive patients. Thus, the development of a new therapeutic agent effective for malignant lymphoma is desired (non-patent document 7).

WO 2017/197051 (patent document 2) describes a compound having a glutarimide group. However, there is no specific disclosure regarding the compound of the present invention having a thiophene ring.

DOCUMENT LIST

Patent Documents patent document 1: National Publication of International Patent Application No. 2012-524071
patent document 2: WO 2017/197051

Non-Patent Document non-patent document 1: Yamazaki, Clinical Immunology, 27, 1270, 1995
non-patent document 2: Terui, Internal Medicine, Vol. 120, No. 4, page 875, 2017
non-patent document 3: Shibayama, Internal Medicine, Vol. 120, No. 4, page 881, 2017
non-patent document 4: Zhang, Internal Medicine, Vol. 120, No. 4, page 887, 2017
non-patent document 5: Suzumiya, The Journal of the Japanese Society of Internal Medicine, Volume 105, No. 9, page 1761, 2016
non-patent document 6: NCCN guideline Japanese version, non-Hodgkin's lymphoma, 2nd edition, 2015
non-patent document 7: Arora. m., Ther Adv Hematol, Vol. 7, No. 4, page 209, 2016

SUMMARY OF INVENTION

Technical Problem

The present invention aims to provide novel thiophene derivatives having a TNF-α production suppressive activity and useful for the treatment of rheumatoid arthritis, Crohn's disease, ulcerative colitis or hematologic cancer, and medicaments containing the same.

Solution to Problem

The present inventors have conducted intensive studies in an attempt to solve the aforementioned problem and found that a compound represented by the following general formula (I) has a superior TNF-α production suppressive activity. They have further conducted various studies on the usefulness thereof as an anticancer drug and completed the present invention. Accordingly, the present invention provides the following.

[1] A compound represented by the following general formula (I):

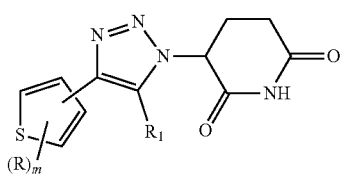

wherein:
$R_1$ is hydrogen or halogen;
R in the number of m are each independently halogen, C1-6 alkyl, C1-6 hydroxyalkyl, C1-6 alkoxy optionally having a substituent, C1-6 alkoxycarbonyl, or C1-6 alkylcarbonyl, or two R on the adjacent ring carbon atom are bonded to each other to form, together with a carbon atom linked thereto, a 5- or 6-membered ring containing 1-2 oxygen atoms; and
m is 0, 1, 2 or 3,
or a salt thereof (hereinafter sometimes to be referred to as "the present compound").

[2] The compound of the above-mentioned [1] or a salt thereof, wherein the compound represented by the general formula (I) is a compound represented by the following general formula (IA) or (IB):

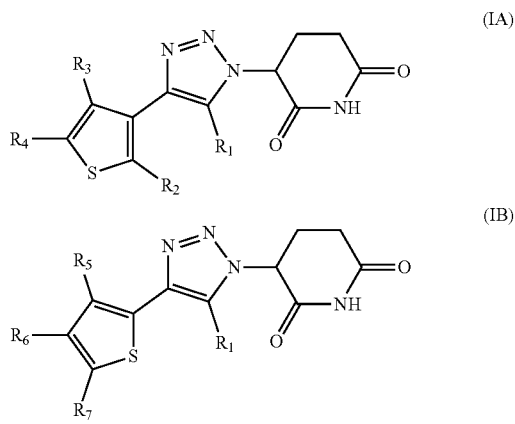

wherein:
$R_1$ is hydrogen or halogen;
$R_2$ is hydrogen, halogen, C1-6 alkyl, C1-6 hydroxyalkyl, C1-6 alkoxy, C1-6 alkoxycarbonyl, or C1-6 alkylcarbonyl;
$R_3$ is hydrogen, halogen, C1-6 alkyl, or C1-6 alkoxy optionally having a substituent;
$R_4$ is hydrogen, halogen, C1-6 alkyl, C1-6 hydroxyalkyl, C1-6 alkoxy, C1-6 alkoxycarbonyl, or C1-6 alkylcarbonyl;
$R_5$ is hydrogen, halogen, C1-6 alkyl, C1-6 hydroxyalkyl, C1-6 alkoxy, C1-6 alkoxycarbonyl, or C1-6 alkylcarbonyl;
$R_6$ is hydrogen, halogen, C1-6 alkyl, C1-6 hydroxyalkyl, C1-6 alkoxy, C1-6 alkoxycarbonyl, or C1-6 alkylcarbonyl, or
$R_5$ and $R_6$ are bonded to each other to form, together with a carbon atom linked thereto, a 5- or 6-membered ring containing 1-2 oxygen atoms; and
$R_7$ is hydrogen, halogen, C1-6 alkyl, C1-6 hydroxyalkyl, C1-6 alkoxy, C1-6 alkoxycarbonyl, or C1-6 alkylcarbonyl.
[3] The compound of the above-mentioned [2] or a salt thereof, wherein $R_1$ is hydrogen or halogen;
$R_2$ is hydrogen, halogen, or C1-6 alkoxy;
$R_3$ is hydrogen, halogen, C1-6 alkyl, or C1-6 alkoxy optionally having a substituent;
$R_4$ is hydrogen, halogen, C1-6 alkyl, C1-6 hydroxyalkyl, C1-6 alkoxy, or C1-6 alkoxycarbonyl;
$R_5$ and $R_6$ are each hydrogen, or
$R_5$ and $R_6$ are bonded to each other to form, together with a carbon atom linked thereto, a 5- or 6-membered ring containing 1-2 oxygen atoms; and
$R_7$ is hydrogen, halogen, C1-6 alkyl, or C1-6 alkylcarbonyl.
[4] The compound of any one of the above-mentioned [1] to [3] or a salt thereof, wherein the C1-6 alkoxy optionally having a substituent for R and $R_3$ is C1-6 chain alkoxy, C3-6 cycloalkoxy, or
alkoxy represented by the formula: —O—X—Y
wherein:
X is a linear or branched chain C1-6 alkylene; and
Y is C3-6 cycloalkyl, or pyridine, naphthalene or benzothiophene, each of which optionally has a substituent, or a substituent represented by the formula general (II):

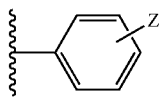

(II)

Z is hydrogen, C1-6 alkoxy, C1-6 alkoxymethyl, halogen, or a substituent represented by the following general formula (III), (IV), (V) or (VI):

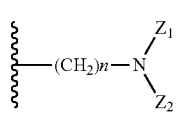

(III)

$Z_1$ and $Z_2$ are each independently hydrogen or C1-6 alkyl, or $Z_1$ and $Z_2$ are bonded to each other to form, together with a nitrogen atom linked thereto, a 5- or 6-membered ring; and n is 1 or 2

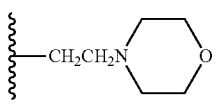

(IV)

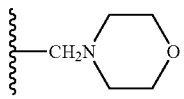

(V)

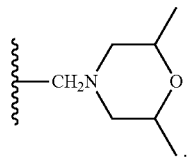

(VI)

[5] The compound of the above-mentioned [4], wherein X is $CH_2$, $CH(CH_3)$ or $CH_2CH_2$, or a salt thereof.

[6] The compound of any one of the above-mentioned [2] to [5], or an acid addition salt thereof, wherein $R_1$ is hydrogen, iodo, bromo or chloro;

$R_2$ is hydrogen, bromo or methoxy;

$R_3$ is hydrogen, bromo, chloro, methyl, methoxy, ethoxy, propoxy, isopropoxy, butoxy, cyclopentyloxy, cyclopropylmethoxy, cyclopentylmethoxy, cyclohexylmethoxy, benzyloxy, 1-phenylethoxy, pyridin-2-ylmethoxy, pyridin-3-ylmethoxy, pyridin-4-ylmethoxy, benzo[b]thiophen-2-ylmethoxy, 4-methoxybenzyloxy, 4-(methoxymethyl)benzyloxy, 4-chlorobenzyloxy, 4-(pyrrolidin-1-ylmethyl)benzyloxy, 4-(piperidin-1-ylmethyl)benzyloxy, 4-[(dimethylamino)methyl]benzyloxy, 4-(2-morpholinoethyl)benzyloxy, 2-(morpholinomethyl)benzyloxy, 3-(morpholinomethyl)benzyloxy, 4-(morpholinomethyl)benzyloxy or 4-{[(2S,6R)-2,6-dimethylmorpholino]methyl}benzyloxy;

$R_4$ is hydrogen, bromo, chloro, methyl, hydroxymethyl, methoxy, ethoxy or methoxycarbonyl;

$R_5$ and $R_6$ are each hydrogen, or $R_5$ and $R_6$ are bonded to each other to form, together with a carbon atom linked thereto, a 6-membered ring containing two oxygen atoms;

$R_7$ is hydrogen, chloro, bromo, methyl or acetyl.

[7] The compound of any one of the above-mentioned [1] to [6], or a salt thereof, wherein the compound or the salt is selected from 3-[4-(4-bromothiophen-3-yl)-1H-1,2,3-triazol-1-yl]piperidine-2,6-dione, 3-[4-(thiophen-3-yl)-1H-1,2,3-triazol-1-yl]piperidine-2,6-dione, 3-[4-(thiophen-2-yl)-1H-1,2,3-triazol-1-yl]piperidine-2,6-dione, 3-[5-chloro-4-(thiophen-3-yl)-1H-1,2,3-triazol-1-yl]piperidine-2,6-dione, 3-[4-(5-methylthiophen-2-yl)-1H-1,2,3-triazol-1-yl]piperidine-2,6-dione, 3-[4-(5-methylthiophen-3-yl)-1H-1,2,3-triazol-1-yl]piperidine-2,6-dione, 3-[4-(4-methylthiophen-3-yl)-1H-1,2,3-triazol-1-yl]piperidine-2,6-dione, 3-[4-(5-acetylthiophen-2-yl)-1H-1,2,3-triazol-1-yl]piperidine-2,6-dione, 3-{4-[5-(hydroxymethyl)thiophen-3-yl]-1H-1,2,3-triazol-1-yl}piperidine-2,6-dione, 3-[4-(2,3-dihydrothieno[3,4-b][1,4]dioxin-5-yl)-1H-1,2,3-triazol-1-yl]piperidine-2,6-dione, 3-[4-(5-chlorothiophen-2-yl)-1H-1,2,3-triazol-1-yl]piperidine-2,6-dione, 3-[4-(5-bromothiophen-2-yl)-1H-1,2,3-triazol-1-yl]piperidine-2,6-dione, 3-[4-(2,5-dibromothiophen-3-yl)-1H-1,2,3-triazol-1-yl]piperidine-2,6-dione, 3-[4-(4-chlorothiophen-3-yl)-1H-1,2,3-triazol-1-yl]piperidine-2,6-dione, 3-[4-(4-methoxy-5-methylthiophen-3-yl)-1H-1,2,3-triazol-1-yl]piperidine-2,6-dione, methyl 4-[1-(2,6-dioxopiperidin-3-yl)-1H-1,2,3-triazol-4-yl]-3-methoxythiophene-2-carboxylate, 3-[4-(4-ethoxythiophen-3-yl)-1H-1,2,3-triazol-1-yl]piperidine-2,6-dione, 3-[4-(2-methoxythiophen-3-yl)-1H-1,2,3-triazol-1-yl]piperidine-2,6-dione, 3-[4-(4-methoxythiophen-3-yl)-1H-1,2,3-triazol-1-yl]piperidine-2,6-dione, 3-[4-(5-methoxythiophen-3-yl)-1H-1,2,3-triazol-1-yl]piperidine-2,6-dione, 3-[4-(4-propoxythiophen-3-yl)-1H-1,2,3-triazol-1-yl]piperidine-2,6-dione, 3-[4-(5-chloro-4-methoxythiophen-3-yl)-1H-1,2,3-triazol-1-yl]piperidine-2,6-dione, 3-[4-(5-bromo-4-methoxythiophen-3-yl)-1H-1,2,3-triazol-1-yl]piperidine-2,6-dione, 3-[4-(5-ethoxythiophen-3-yl)-1H-1,2,3-triazol-1-yl]piperidine-2,6-dione, 3-[4-(4-butoxythiophen-3-yl)-1H-1,2,3-triazol-1-yl]piperidine-2,6-dione, 3-[4-(4-isopropoxythiophen-3-yl)-1H-1,2,3-triazol-1-yl]piperidine-2,6-dione, 3-{4-[4-(cyclopentyloxy)thiophen-3-yl]-1H-1,2,3-triazol-1-yl}piperidine-2,6-dione, 3-{4-[4-(cyclopropylmethoxy)thiophen-3-yl]-1H-1,2,3-triazol-1-yl}piperidine-2,6-dione, 3-{4-[4-(cyclopentylmethoxy)thiophen-3-yl]-1H-1,2,3-triazol-1-yl}piperidine-2,6-dione, 3-{4-[4-(cyclohexylmethoxy)thiophen-3-yl]-1H-1,2,3-triazol-1-yl}piperidine-2,6-dione, 3-{4-[4-(4-methoxybenzyloxy)thiophen-3-yl]-1H-1,2,3-triazol-1-yl}piperidine-2,6-dione, 3-{4-[4-(benzyloxy)thiophen-3-yl]-1H-1,2,3-triazol-1-yl}piperidine-2,6-dione, 3-{4-[4-(pyridin-4-ylmethoxy)thiophen-3-yl]-1H-1,2,3-triazol-1-yl}piperidine-2,6-dione,
3-{4-[4-(pyridin-2-ylmethoxy)thiophen-3-yl]-1H-1,2,3-triazol-1-yl}piperidine-2,6-dione,
3-{4-[4-(pyridin-3-ylmethoxy)thiophen-3-yl]-1H-1,2,3-triazol-1-yl}piperidine-2,6-dione,
3-(4-{4-[4-(morpholinomethyl)benzyloxy]thiophen-3-yl}-1H-1,2,3-triazol-1-yl)piperidine-2,6-dione,
3-(4-{4-[4-(methoxymethyl)benzyloxy]thiophen-3-yl}-1H-1,2,3-triazol-1-yl)piperidine-2,6-dione,
3-{4-[4-(4-{[(2S,6R)-2,6-dimethylmorpholino]methyl}benzyloxy)thiophen-3-yl]-1H-1,2,3-triazol-1-yl}piperidine-2,6-dione,
3-(4-{4-[3-(morpholinomethyl)benzyloxy]thiophen-3-yl}-1H-1,2,3-triazol-1-yl)piperidine-2,6-dione,
3-(4-{4-[2-(morpholinomethyl)benzyloxy]thiophen-3-yl}-1H-1,2,3-triazol-1-yl)piperidine-2,6-dione,
3-(4-{4-[4-(pyrrolidin-1-ylmethyl)benzyloxy]thiophen-3-yl}-1H-1,2,3-triazol-1-yl)piperidine-2,6-dione,
3-(4-{4-[4-(piperidin-1-ylmethyl)benzyloxy]thiophen-3-yl}-1H-1,2,3-triazol-1-yl)piperidine-2,6-dione,
3-{4-[4-(4-chlorobenzyloxy)thiophen-3-yl]-1H-1,2,3-triazol-1-yl}piperidine-2,6-dione,
3-{4-[4-(1-phenylethoxy)thiophen-3-yl]-1H-1,2,3-triazol-1-yl}piperidine-2,6-dione,
3-(4-{4-[4-(2-morpholinoethyl)benzyloxy]thiophen-3-yl}-1H-1,2,3-triazol-1-yl)piperidine-2,6-dione,
3-[4-(4-{4-[(dimethylamino)methyl]benzyloxy}thiophen-3-yl)-1H-1,2,3-triazol-1-yl]piperidine-2,6-dione,
3-{4-[4-(benzo[b]thiophen-2-ylmethoxy)thiophen-3-yl]-1H-1,2,3-triazol-1-yl}piperidine-2,6-dione,
3-[5-bromo-4-(thiophen-3-yl)-1H-1,2,3-triazol-1-yl]piperidine-2,6-dione, and
3-[5-iodo-4-(4-methoxythiophen-3-yl)-1H-1,2,3-triazol-1-yl]piperidine-2,6-dione, and acid addition salts thereof.

[8] The compound of the above-mentioned [2] or a salt thereof, wherein the compound represented by the general formula (I) is a compound represented by the following general formula (IA):

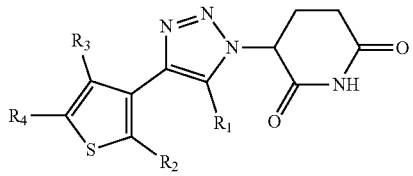

wherein:
$R_1$ is hydrogen;
$R_2$ is hydrogen;
$R_3$ is hydrogen or C1-6 alkoxy optionally having a substituent; and
$R_4$ is hydrogen, C1-6 alkoxy or halogen.

[9] The compound of the above-mentioned [8] or a salt thereof, wherein $R_3$ is hydrogen, C1-6 chain alkoxy, or alkoxy represented by the formula: —O—X—Y
wherein:
X is linear C1-6 alkylene; and
Y is benzothiophene, pyridine or a substituent represented by the general formula (II):

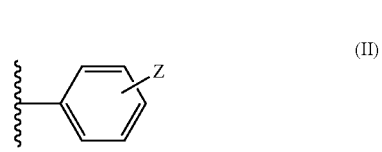

Z is hydrogen, C1-6 chain alkoxymethyl, or a substituent represented by the following general formula (III), (IV), (V) or (VI):

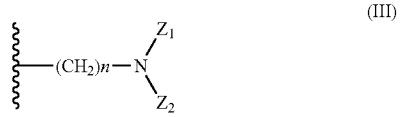

$Z_1$ and $Z_2$ are each C1-6 chain alkyl, or
$Z_1$ and $Z_2$ are bonded to each other to form, together with a nitrogen atom linked thereto, a 5- or 6-membered ring; and
n is 1 or 2;

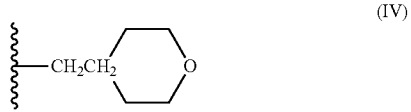

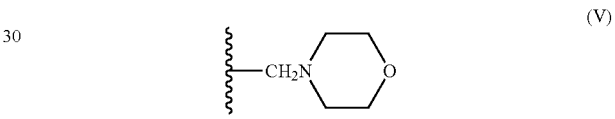

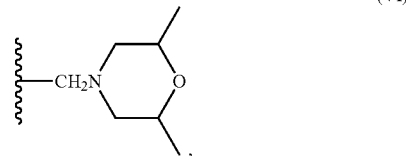

and
$R_4$ is hydrogen, C1-6 alkoxy or halogen.

[10] The compound of any one of the above-mentioned [1] to [9], or a salt thereof, wherein the compound or the salt is selected from
3-[4-(5-methoxythiophen-3-yl)-1H-1,2,3-triazol-1-yl]piperidine-2,6-dione,
3-[4-(5-bromo-4-methoxythiophen-3-yl)-1H-1,2,3-triazol-1-yl]piperidine-2,6-dione,
3-[4-(4-methoxythiophen-3-yl)-1H-1,2,3-triazol-1-yl]piperidine-2,6-dione,
3-{4-[4-(benzyloxy)thiophen-3-yl]-1H-1,2,3-triazol-1-yl}piperidine-2,6-dione,
3-(4-{4-[4-(methoxymethyl)benzyloxy]thiophen-3-yl}-1H-1,2,3-triazol-1-yl)piperidine-2,6-dione,
3-{4-[4-(4-{[(2S,6R)-2,6-dimethylmorpholino]methyl}benzyloxy)thiophen-3-yl]-1H-1,2,3-triazol-1-yl}piperidine-2,6-dione,
3-(4-{4-[4-(pyrrolidin-1-ylmethyl)benzyloxy]thiophen-3-yl}-1H-1,2,3-triazol-1-yl)piperidine-2,6-dione,
3-(4-{4-[4-(piperidin-1-ylmethyl)benzyloxy]thiophen-3-yl}-1H-1,2,3-triazol-1-yl)piperidine-2,6-dione,
3-(4-{4-[4-(2-morpholinoethyl)benzyloxy]thiophen-3-yl}-1H-1,2,3-triazol-1-yl)piperidine-2,6-dione,
3-[4-(4-{4-[(dimethylamino)methyl]benzyloxy}thiophen-3-yl)-1H-1,2,3-triazol-1-yl]piperidine-2,6-dione, and 3-{4-[4-(benzo[b]thiophen-2-ylmethoxy)thiophen-3-yl]-1H-1,2,3-triazol-1-yl}piperidine-2,6-dione and acid addition salts thereof.

[11] The compound of any one of the above-mentioned [1] to [9], or a salt thereof, wherein the compound or the salt is selected from 3-[4-(5-methoxythiophen-3-yl)-1H-1,2,3-triazol-1-yl]piperidine-2,6-dione, 3-[4-(4-methoxythiophen-3-yl)-1H-1,2,3-triazol-1-yl]piperidine-2,6-dione, 3-(4-{4-[4-(methoxymethyl)benzyloxy]thiophen-3-yl}-1H-1,2,3-triazol-1-yl)piperidine-2,6-dione, 3-{4-[4-(4-{[(2S,6R)-2,6-dimethylmorpholino]methyl}benzyloxy)thiophen-3-yl]-1H-1,2,3-triazol-1-yl}piperidine-2,6-dione, 3-(4-{4-[4-(piperidin-1-ylmethyl)benzyloxy]thiophen-3-yl}-1H-1,2,3-triazol-1-yl)piperidine-2,6-dione, and acid addition salts thereof.

[12] A medicament comprising the compound of the above-mentioned [1] or a salt thereof as an active ingredient.

[13] The medicament of the above-mentioned [12], wherein the medicament is a TNF-α production suppressor.

[14] The medicament of the above-mentioned [12], wherein the medicament is a prophylactic or therapeutic agent for an inflammatory disease, an autoimmune disease, or a hematologic cancer.

[15] A pharmaceutical composition comprising the compound of the above-mentioned [1] or a salt thereof as an active ingredient together with a pharmaceutically acceptable carrier.

[16] The pharmaceutical composition of the above-mentioned [15], wherein the composition is a TNF-α production suppressor.

[17] The pharmaceutical composition of the above-mentioned [15], wherein the composition is a prophylactic or therapeutic agent for an inflammatory disease, an autoimmune disease, or a hematologic cancer.

[18] A method for suppressing TNF-α production, comprising administering an effective amount of the compound of the above-mentioned [1] or a salt thereof to a mammal.

[19] A method for preventing or treating an inflammatory disease, an autoimmune disease, or a hematologic cancer, comprising administering a prophylactically or therapeutically effective amount of the compound of the above-mentioned [1] or a salt thereof to a mammal in need of the administration thereof.

[20] The compound of the above-mentioned [1] or a salt thereof for use in the prophylaxis or treatment of an inflammatory disease, an autoimmune disease, or a hematologic cancer.

[21] Use of the compound of the above-mentioned [1] or a salt thereof for the production of a medicament.

[22] Use of the compound of the above-mentioned [1] or a salt thereof for the production of a medicament for the prophylaxis or treatment of an inflammatory disease, an autoimmune disease, or a hematologic cancer.

[23] The medicament of the above-mentioned [14], the pharmaceutical composition of the above-mentioned [17], the method of the above-mentioned [19], the compound or a salt thereof of the above-mentioned [20], or the use of the above-mentioned [22], wherein the autoimmune disease is rheumatoid arthritis, Crohn's disease or ulcerative colitis.

[24] The medicament of the above-mentioned [14], the pharmaceutical composition of the above-mentioned [17], the method of the above-mentioned [19], the compound or a salt thereof of the above-mentioned [20], or the use of the above-mentioned [22], wherein the hematologic cancer is leukemia, malignant lymphoma, or multiple myeloma.

[25] The medicament of the above-mentioned [14], the pharmaceutical composition of the above-mentioned [17], the method of the above-mentioned [19], the compound or a salt thereof of the above-mentioned [20], or the use of the above-mentioned [22], wherein the hematologic cancer is multiple myeloma.

[26] The medicament of the above-mentioned [14], the pharmaceutical composition of the above-mentioned [17], the method of the above-mentioned [19], the compound or a salt thereof of the above-mentioned [20], or the use of the above-mentioned [22], wherein the hematologic cancer is malignant lymphoma.

[27] The medicament of the above-mentioned [14], the pharmaceutical composition of the above-mentioned [17], the method of the above-mentioned [19], the compound or a salt thereof of the above-mentioned [20], or the use of the above-mentioned [22], wherein the hematologic cancer is leukemia.

[28] The medicament of the above-mentioned [26], the pharmaceutical composition of the above-mentioned [26], the method of the above-mentioned [26], the compound or a salt thereof of the above-mentioned [26], or the use of the above-mentioned [26], wherein the malignant lymphoma is non-Hodgkin's lymphoma.

[29] The medicament of the above-mentioned [28], the pharmaceutical composition of the above-mentioned [28], the method of the above-mentioned [28], the compound or a salt thereof of the above-mentioned [28], or the use of the above-mentioned [28], wherein the non-Hodgkin's lymphoma is precursor lymphoid neoplasms or mature B-cell neoplasms.

Advantageous Effects of Invention

According to the present invention, novel thiophene derivatives useful for the prophylaxis or treatment of inflammatory diseases such as rheumatoid arthritis, Crohn's disease, ulcerative colitis and the like, autoimmune disease, and hematologic cancer such as multiple myeloma, malignant lymphoma, leukemia and the like, and the like is provided.

DESCRIPTION OF EMBODIMENTS

[The Present Compound]

The present invention is explained in detail in the following.

The definition of each group used in the present specification is described in detail below. Unless particularly indicated, each group has the following definition.

A salt of the present compound includes acid addition salt, salt with a base, salt with an amino acid and the like. Examples of the acid addition salt include salts with inorganic acids such as hydrochloric acid, sulfuric acid, hydrobromic acid, nitric acid and the like, salts with organic acids such as gluconic acid, tartaric acid, maleic acid, fumaric acid, succinic acid, malic acid, citric acid, mandelic acid, acetic acid, methanesulfonic acid and the like, and the like. Examples of the salts with bases include salts with alkali metals such as sodium, potassium and the like, salts with alkaline earth metals such as calcium and the like, and the like. Examples of the salts with amino acids include salts with amino acids such as glycine, lysine, arginine, ornithine, glutamic acid, aspartic acid and the like, and the like. Concrete examples mentioned above are not limitative. Among these, an acid addition salt is preferable. When the present compound is used as a medicament, a pharmaceutically acceptable salt is particularly preferable.

In the present compound, halogen is fluoro, chloro, bromo, or iodo.

In the present compound, C1-6 alkyl is, for example, a linear or branched chain alkyl group having 1 to 6 carbon atoms (hereinafter sometimes to be referred to as "C1-6 chain alkyl") or a cyclic alkyl group having 3 to 6 carbon atoms (hereinafter sometimes to be referred to as "C3-6 cycloalkyl"), such as methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, cyclopropyl, cyclobutyl, cyclopentyl, cyclohexyl and the like, and optionally has a substituent. It is preferably C1-4 chain alkyl or C3-6 cycloalkyl.

In the present compound, C1-6 hydroxyalkyl is the above-mentioned C1-6 alkyl substituted by one or more hydroxy groups. Generally, it is substituted by 1 to 3 hydroxy groups, preferably substituted by one hydroxy group. For example, it is $CH_2OH$, $CH_2CH_2OH$, $CH_2CH_2CH_2OH$, $CH(OH)CH_2OH$, $CH(CH_3)OH$, $CH(CH_2OH)_2$ or the like, optionally having a substituent. It is preferably C1-4 hydroxy chain alkyl.

In the present compound, C1-6 alkoxy is, for example, a linear or branched chain alkoxy group having 1 to 6 carbon atoms (hereinafter sometimes to be referred to as "C1-6 chain alkoxy") or a cyclic alkoxy group having 3 to 6 carbon atoms (hereinafter sometimes to be referred to as "C3-6 cycloalkoxy"), such as methoxy, ethoxy, propoxy, isopropoxy, butoxy, isobutoxy, sec-butoxy, tert-butoxy, pentyloxy, isopentyloxy, neopentyloxy, hexyloxy, cyclopropoxy, cyclobutoxy, cyclopentyloxy and the like, and optionally has a substituent. It is preferably C1-4 chain alkoxy or C3-6 cycloalkoxy.

In the present compound, C1-6 alkylcarbonyl is a carbonyl group substituted by a C1-6 alkyl group. It is, for example, alkylcarbonyl wherein the alkyl moiety is linear or branched chain alkyl having 1 to 6 carbon atoms, such as methylcarbonyl, ethylcarbonyl, propylcarbonyl, isopropylcarbonyl, butylcarbonyl, isobutylcarbonyl, sec-butylcarbonyl, tert-butylcarbonyl, pentylcarbonyl, isopentylcarbonyl, neopentylcarbonyl, hexylcarbonyl and the like, and optionally has a substituent. It is preferably C1-4 alkylcarbonyl.

In the present compound, C1-6 alkoxycarbonyl is a carbonyl group substituted by a C1-6 alkoxy group. It is, for example, alkoxycarbonyl group wherein the alkoxy moiety is linear or branched chain alkoxy having 1 to 6 carbon atoms, such as methoxycarbonyl, ethoxycarbonyl, propoxycarbonyl, isopropoxycarbonyl, butoxycarbonyl, tert-butoxycarbonyl, pentyloxycarbonyl, isopentyloxycarbonyl, neopentyloxycarbonyl, hexyloxycarbonyl and the like, and optionally has a substituent. It is preferably C1-4 alkoxycarbonyl.

In the present compound, C3-6 cycloalkyl is, for example, a cyclic alkyl group having 3 to 6 carbon atoms, such as cyclopropyl, cyclobutyl, cyclopentyl, cyclohexyl and the like, and optionally has a substituent.

In the present compound, C3-6 cycloalkoxy is, for example, a cyclic alkoxy group having 3 to 6 carbon atoms, such as cyclopropoxy, cyclobutoxy, cyclopentyloxy, cyclohexyloxy and the like, and optionally has a substituent.

In the present compound, C1-6 alkylene is, for example, a divalent group that can be formed by removing one hydrogen atom from the groups recited as examples of the aforementioned C1-6 alkyl, and optionally has a substituent.

It is preferably linear or branched chain C1-6 alkylene, more preferably linear or branched chain C1-4 alkylene.

The "optionally has a substituent" means that a substituent may be absent or one or more substituents may be present. An example of the presence of a substituent is when $R_3$ in the above-mentioned general formula (IA) is C1-6 alkoxy substituted by at least one (preferably 1-3) substituent of the above-mentioned general formula (II) at substitutable position(s). Other substituents can be appropriately selected from halogen, hydroxy and the like by those of ordinary skill in the art.

Each symbol in the compound represented by the general formula (I) is explained below.

$R_1$ is hydrogen or halogen (preferably, chloro, bromo, iodo). R in the number of m are each independently halogen, C1-6 alkyl, C1-6 hydroxyalkyl, C1-6 alkoxy optionally having a substituent, C1-6 alkoxycarbonyl, or C1-6 alkylcarbonyl, or two R on the adjacent ring carbon atom are bonded to each other to form, together with a carbon atom linked thereto, a 5- or 6-membered ring containing 1-2 oxygen atoms, and m is 0, 1, 2 or 3.

Preferably, R in the number of m are each independently halogen (e.g., chloro, bromo);
C1-6 chain alkyl, more preferably C1-4 chain alkyl (e.g., methyl);
C1-6 hydroxy chain alkyl, more preferably C1-4 hydroxy chain alkyl (e.g., hydroxymethyl);
C1-6 chain alkoxy, more preferably C1-4 chain alkoxy (e.g., methoxy, ethoxy, propoxy, isopropoxy, butoxy);
C3-6 cycloalkoxy (e.g., cyclopentyloxy);
alkoxy represented by the formula: —O—X—Y
wherein:
X is linear or branched chain C1-6 alkylene, more preferably linear or branched chain C1-4 alkylene (e.g., methylene, methylmethylene); and
Y is C3-6 cycloalkyl (e.g., cyclopropyl, cyclopentyl, cyclohexyl),
or pyridine, naphthalene or benzothiophene, each of which optionally has a substituent, preferably, pyridine, naphthalene or benzothiophene, more preferably pyridine or benzothiophene, or a substituent represented by the general formula (II):

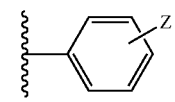

(II)

Z is hydrogen, C1-6 alkoxy, preferably C1-4 chain alkoxy (e.g., methoxy), C1-6 alkoxymethyl, preferably C1-4 chain alkoxymethyl (e.g., methoxymethyl), halogen (e.g., chloro), or a substituent represented by the following general formula (III), (IV), (V) or (VI):

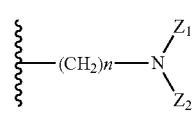

(III)

$Z_1$ and $Z_2$ are each independently hydrogen or C1-6 alkyl, preferably, hydrogen or C1-6 chain alkyl, more preferably C1-4 chain alkyl (e.g., methyl); or $Z_1$ and $Z_2$ are bonded to each other to form, together with a nitrogen atom linked thereto, a 5- or 6-membered ring (preferably, saturated 5- or 6-membered ring (e.g., pyrrolidine ring, piperidine ring); and n is 1 or 2, preferably 1

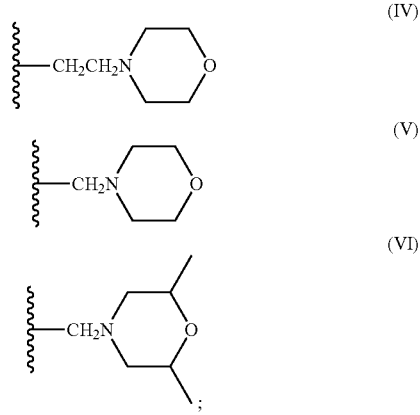

C1-6 chain alkoxycarbonyl, more preferably C1-4 chain alkoxycarbonyl (e.g., methoxycarbonyl);

C1-6 chain alkylcarbonyl, more preferably C1-4 chain alkylcarbonyl (e.g., acetyl); or two R on the adjacent ring carbon atom are bonded to each other to form, together with a carbon atom linked thereto, a saturated 6-membered ring containing 2 oxygen atoms, more preferably 6-membered ring containing $OCH_2CH_2O$ (e.g., 1,4-dioxane ring).

Each symbol in the compound represented by the general formula (IA) or (IB) is explained below.

$R_1$ is hydrogen or halogen;

$R_2$ is hydrogen, halogen, C1-6 alkyl, C1-6 hydroxyalkyl, C1-6 alkoxy, C1-6 alkoxycarbonyl, or C1-6 alkylcarbonyl;

$R_3$ is hydrogen, halogen, C1-6 alkyl, or C1-6 alkoxy optionally having a substituent;

$R_4$ is hydrogen, halogen, C1-6 alkyl, C1-6 hydroxyalkyl, C1-6 alkoxy, C1-6 alkoxycarbonyl, or C1-6 alkylcarbonyl;

$R_5$ is hydrogen, halogen, C1-6 alkyl, C1-6 hydroxyalkyl, C1-6 alkoxy, C1-6 alkoxycarbonyl, or C1-6 alkylcarbonyl;

$R_6$ is hydrogen, halogen, C1-6 alkyl, C1-6 hydroxyalkyl, C1-6 alkoxy, C1-6 alkoxycarbonyl, or C1-6 alkylcarbonyl, or $R_5$ and $R_6$ are bonded to each other to form, together with a carbon atom linked thereto, a 5- or 6-membered ring containing 1-2 oxygen atoms; and $R_7$ is hydrogen, halogen, C1-6 alkyl, C1-6 hydroxyalkyl, C1-6 alkoxy, C1-6 alkoxycarbonyl, or C1-6 alkylcarbonyl.

In the above-mentioned each symbol, halogen, C1-6 alkyl, C1-6 hydroxyalkyl, C1-6 alkoxy, C1-6 alkoxy optionally having a substituent, C1-6 alkoxycarbonyl, C1-6 alkylcarbonyl, and a 5- or 6-membered ring containing 1-2 oxygen atoms formed by $R_5$ and $R_6$ bonded to each other together with a carbon atom linked thereto may be those explained for the above-mentioned compound represented by the general formula (I).

Preferred embodiments of each of the above-mentioned symbols are explained below.

$R_1$ is preferably hydrogen, chloro, bromo, or iodo.

$R_2$ is preferably hydrogen, halogen, or C1-6 chain alkoxy. More preferably, it is hydrogen, halogen, or C1-4 chain alkoxy, further preferably hydrogen, bromo, or methoxy.

$R_3$ is preferably hydrogen, halogen, C1-6 chain alkyl, or C1-6 alkoxy optionally having a substituent. As the halogen, bromo or chloro is preferable. As the C1-6 chain alkyl, C1-4 chain alkyl is preferable, and methyl is more preferable. The C1-6 alkoxy optionally having a substituent is preferably C1-6 chain alkoxy, C3-6 cycloalkoxy, or alkoxy represented by the formula: —O—X—Y.

As the "C1-6 chain alkoxy" for $R_3$, C1-4 chain alkoxy is preferable, and methoxy, ethoxy, propoxy, isopropoxy, or butoxy is more preferable.

As the "C3-6 cycloalkoxy" for $R_3$, cyclopentyloxy is preferable.

In "alkoxy represented by the formula: —O—X—Y" for $R_3$, X is a linear or branched chain C1-6 alkylene. Y is C3-6 cycloalkyl, or pyridine, naphthalene or benzothiophene, each of which optionally has a substituent, or a substituent represented by the following formula (II):

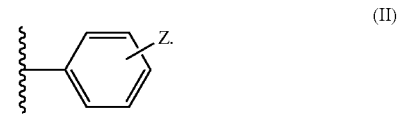

The "linear or branched chain C1-6 alkylene" for X is preferably linear or branched chain C1-4 alkylene, more preferably methylene(—$CH_2$—) or methylmethylene(—CH($CH_3$)—), further preferably methylene(—$CH_2$—).

The "C3-6 cycloalkyl" for Y is preferably cyclopropyl, cyclopentyl, or cyclohexyl.

The "pyridine, naphthalene or benzothiophene, each of which optionally has a substituent" for Y is preferably pyridine, naphthalene, or benzothiophene, more preferably pyridine or benzothiophene.

In the "substituent represented by the general formula (II)" for Y, Z is hydrogen, C1-6 alkoxy, C1-6 alkoxymethyl, halogen, or a substituent represented by the following general formula (III), (IV), (V) or (VI):

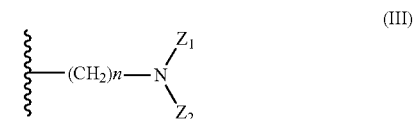

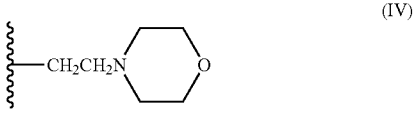

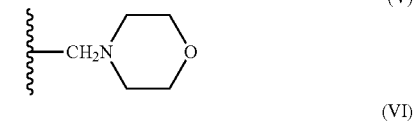

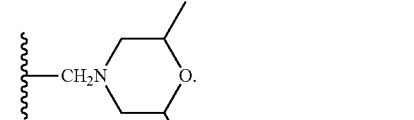

The C1-6 alkoxy for Z is preferably C1-6 chain alkoxy, more preferably C1-4 chain alkoxy, most preferably methoxy.

The C1-6 alkoxymethyl for Z is preferably C1-6 chain alkoxymethyl, more preferably C1-4 chain alkoxymethyl, most preferably methoxymethyl.

The halogen for Z is preferably chloro, bromo, iodo, more preferably chloro.

In the substituent represented by the general formula (III), $Z_1$ and $Z_2$ are each independently hydrogen or C1-6 alkyl, preferably hydrogen or C1-6 chain alkyl, more preferably C1-4 chain alkyl, most preferably methyl; or $Z_1$ and $Z_2$ are bonded to each other to form, together with a nitrogen atom linked thereto, a 5- or 6-membered ring, preferably saturated 5- or 6-membered ring, more preferably pyrrolidine ring or piperidine ring; and n is 1 or 2, more preferably 1.

The most preferable "alkoxy represented by the formula: —O—X—Y" is, for example, cyclopropylmethoxy, cyclopentylmethoxy, cyclohexylmethoxy, benzyloxy, phenylethoxy (particularly preferably 1-phenylethoxy), methoxybenzyloxy (particularly preferably 4-methoxybenzyloxy), methoxymethylbenzyloxy (particularly preferably 4-(methoxymethyl)benzyloxy), chlorobenzyloxy (particularly preferably 4-chlorobenzyloxy), (pyrrolidin-1-ylmethyl)benzyloxy (particularly preferably 4-(pyrrolidin-1-ylmethyl)benzyloxy), (piperidin-1-ylmethyl)benzyloxy (particularly preferably 4-(piperidin-1-ylmethyl)benzyloxy), [(dimethylamino)methyl]benzyloxy (particularly preferably 4-[(dimethylamino)methyl]benzyloxy), morpholinoethylbenzyloxy (particularly preferably 4-(2-morpholinoethyl)benzyloxy), morpholinomethylbenzyloxy (particularly preferably 2-(morpholinomethyl)benzyloxy, 3-(morpholinomethyl)benzyloxy, 4-(morpholinomethyl)benzyloxy), or 2,6-dimethylmorpholinomethylbenzyloxy (particularly preferably 4-{[(2S,6R)-2,6-dimethylmorpholino]methyl}benzyloxy).

$R_4$ is preferably hydrogen, halogen, C1-6 chain alkyl, C1-6 hydroxy chain alkyl, C1-6 chain alkoxy, or C1-6 chain alkoxycarbonyl.

The halogen for $R_4$ is more preferably bromo or chloro.

The C1-6 chain alkyl for $R_4$ is more preferably C1-4 chain alkyl, most preferably methyl.

The C1-6 hydroxy chain alkyl for $R_4$ is more preferably C1-4 hydroxy chain alkyl, most preferably hydroxymethyl.

The C1-6 chain alkoxy for $R_4$ is more preferably C1-4 chain alkoxy, most preferably methoxy or ethoxy.

The C1-6 chain alkoxycarbonyl for $R_4$ is more preferably C1-4 chain alkoxycarbonyl, most preferably methoxycarbonyl.

$R_5$ and $R_6$ are preferably each independently hydrogen, or $R_5$ and $R_6$ are bonded to each other to form, together with a carbon atom linked thereto, a 5- or 6-membered ring containing 1-2 oxygen atoms. The 5- or 6-membered ring containing 1-2 oxygen atoms is preferably a saturated 6-membered ring containing two oxygen atoms, more preferably a 6-membered ring containing $OCH_2CH_2O$, most preferably a 1,4-dioxane ring.

$R_7$ is preferably hydrogen, halogen, C1-6 chain alkyl, or C1-6 chain alkylcarbonyl, more preferably, hydrogen, halogen, C1-4 chain alkyl, or C1-4 chain alkylcarbonyl, most preferably hydrogen, bromo, chloro, methyl or acetyl.

Specific preferable examples of the compound represented by the following general formula (I) include the following compounds.

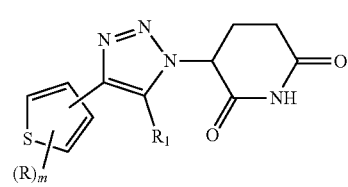

(I)

[Compound I-1]

Compound (I) wherein $R_1$ is hydrogen or halogen;

R in the number of m are each independently halogen, C1-6 chain alkyl, C1-6 hydroxy chain alkyl,
C1-6 chain alkoxy, C3-6 cycloalkoxy,
alkoxy represented by the formula: —O—X—Y
wherein:
X is a linear or branched chain C1-6 alkylene; and
Y is C3-6 cycloalkyl, pyridine, naphthalene or benzothiophene, or a substituent represented by the general formula (II):

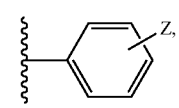

(II)

Z is hydrogen, C1-6 chain alkoxy, C1-6 chain alkoxymethyl, halogen, or a substituent represented by the following general formula (III), (IV), (V) or (VI):

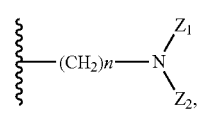

(III)

$Z_1$ and $Z_2$ are each independently hydrogen or C1-6 chain alkyl;
or
$Z_1$ and $Z_2$ are bonded to each other to form, together with a nitrogen atom linked thereto, a saturated 5- or 6-membered ring; and
n is 1 or 2,

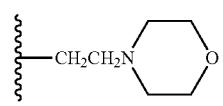

(IV)

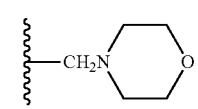

(V)

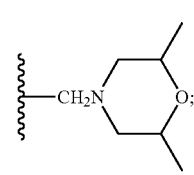

(VI)

C1-6 chain alkoxycarbonyl, or C1-6 chain alkylcarbonyl, or two R on the adjacent ring carbon atom are bonded to each other to form, together with a carbon atom linked thereto, a saturated 6-membered ring containing 2 oxygen atoms; and m is 0, 1, 2 or 3.

[Compound I-2]

Compound (I) wherein $R_1$ is hydrogen;

R in the number of m are each independently halogen, C1-6 chain alkoxy, alkoxy represented by the formula: —O—X—Y wherein:

X is linear C1-6 alkylene; and

Y is benzothiophene, pyridine or a substituent represented by the general formula (II):

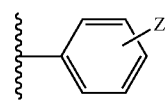

(II)

Z is hydrogen, C1-6 chain alkoxymethyl, or a substituent represented by the following formula (III), (IV), (V) or (VI):

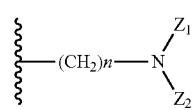

(III)

$Z_1$ and $Z_2$ are each C1-6 chain alkyl; or $Z_1$ and $Z_2$ are bonded to each other to form, together with a nitrogen atom linked thereto, a 5- or 6-membered ring; and n is 1 or 2

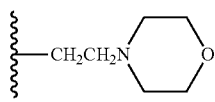

(IV)

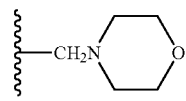

(V)

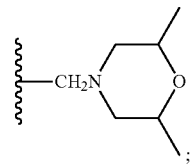

(VI)

and m is 0, 1 or 2.

In another embodiment, specific preferable examples of compound (I) include compound (IA) and compound (IB) represented by the following formulas:

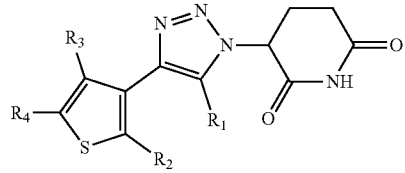

(IA)

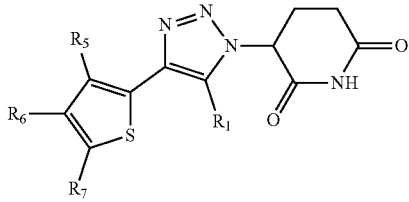

(IB)

wherein $R_1$ is hydrogen or halogen;

$R_2$ is hydrogen, halogen, C1-6 alkyl, C1-6 hydroxyalkyl, C1-6 alkoxy, C1-6 alkoxycarbonyl, or C1-6 alkylcarbonyl;

$R_3$ is hydrogen, halogen, C1-6 alkyl, or C1-6 alkoxy optionally having a substituent;

$R_4$ is hydrogen, halogen, C1-6 alkyl, C1-6 hydroxyalkyl, C1-6 alkoxy, C1-6 alkoxycarbonyl, or C1-6 alkylcarbonyl;

$R_5$ is hydrogen, halogen, C1-6 alkyl, C1-6 hydroxyalkyl, C1-6 alkoxy, C1-6 alkoxycarbonyl, or C1-6 alkylcarbonyl;

$R_6$ is hydrogen, halogen, C1-6 alkyl, C1-6 hydroxyalkyl, C1-6 alkoxy, C1-6 alkoxycarbonyl, or C1-6 alkylcarbonyl, or $R_5$ and $R_6$ are bonded to each other to form, together with a carbon atom linked thereto, a 5- or 6-membered ring containing 1-2 oxygen atoms; and $R_7$ is hydrogen, halogen, C1-6 alkyl, C1-6 hydroxyalkyl, C1-6 alkoxy, C1-6 alkoxycarbonyl, or C1-6 alkylcarbonyl.

Specific preferable examples of compounds (IA) and (IB) include the following compounds.

[Compound (IA)-1] and [Compound (IB)-1]

Compound (IA) and compound (IB), wherein $R_3$ is hydrogen, halogen, C1-6 alkyl, C1-6 alkoxy, or alkoxy represented by the formula: —O—X—Y wherein:

X is a linear or branched chain C1-6 alkylene; and

Y is C3-6 cycloalkyl, or pyridine, naphthalene or benzothiophene, each of which optionally has a substituent (more preferably pyridine, naphthalene or benzothiophene), or a substituent represented by the general formula (II):

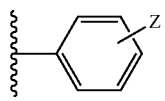

(II)

Z is hydrogen, C1-6 alkoxy, C1-6 alkoxymethyl, halogen, or a substituent represented by the following general formula (III), (IV), (V) or (VI):

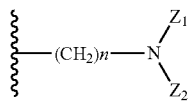

(III)

$Z_1$ and $Z_2$ are each independently hydrogen or C1-6 alkyl, or
$Z_1$ and $Z_2$ are bonded to each other to form, together with a nitrogen atom linked thereto, a 5- or 6-membered ring; and
n is 1 or 2

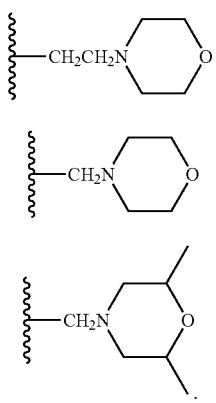

[Compound (IA)-2] and [Compound (IB)-2]

Compound (IA) and compound (IB), wherein $R_1$ is hydrogen or halogen;
$R_2$ is hydrogen, halogen, or C1-6 alkoxy;
$R_3$ is hydrogen, halogen, C1-6 alkyl, or C1-6 alkoxy optionally having a substituent;
$R_4$ is hydrogen, halogen, C1-6 alkyl, C1-6 hydroxyalkyl, C1-6 alkoxy, or C1-6 alkoxycarbonyl;
$R_5$ and $R_6$ are each hydrogen, or
$R_5$ and $R_6$ are bonded to each other to form, together with a carbon atom linked thereto, a 5- or 6-membered ring containing 1-2 oxygen atoms; and
$R_7$ is hydrogen, halogen, C1-6 alkyl, or C1-6 alkylcarbonyl.

[Compound (IA)-3] and [Compound (IB)-3]

Compound (IA) and compound (IB), wherein $R_1$ is hydrogen or halogen;
$R_2$ is hydrogen, halogen, or C1-6 chain alkoxy;
$R_3$ is hydrogen, halogen, C1-6 chain alkyl, C1-6 chain alkoxy, C3-6 cycloalkoxy, or
alkoxy represented by the formula: —O—X—Y
wherein:
X is a linear or branched chain C1-6 alkylene; and
Y is C3-6 cycloalkyl, pyridine, benzothiophene, or a substituent represented by the general formula (II):

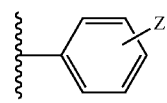

Z is hydrogen, C1-6 chain alkoxy, C1-6 chain alkoxymethyl, halogen, or a substituent represented by the following general formula (III), (IV), (V) or (VI):

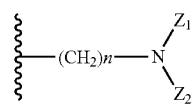

$Z_1$ and $Z_2$ are each independently C1-6 chain alkyl; or
$Z_1$ and $Z_2$ are bonded to each other to form, together with a nitrogen atom linked thereto, a 5- or 6-membered ring; and
n is 1 or 2

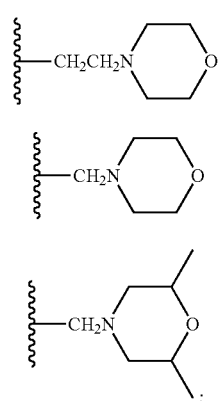

$R_4$ is hydrogen, halogen, C1-6 chain alkyl, C1-6 hydroxy chain alkyl, C1-6 chain alkoxy, or C1-6 chain alkoxycarbonyl;
$R_5$ and $R_6$ are each hydrogen, or
$R_5$ and $R_6$ are bonded to each other to form, together with a carbon atom linked thereto, a 5- or 6-membered ring containing 1-2 oxygen atoms; and
$R_7$ is hydrogen, halogen, C1-6 chain alkyl, or C1-6 chain alkylcarbonyl.

[Compound (IA)-4]

Compound (IA), wherein $R_1$ is hydrogen;
$R_2$ is hydrogen;
$R_3$ is hydrogen, C1-6 chain alkoxy, or
alkoxy represented by the formula: —O—X—Y
wherein:
X is linear C1-6 alkylene; and
Y is benzothiophene, pyridine or a substituent represented by the general formula (II):

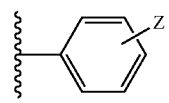

Z is hydrogen, C1-6 chain alkoxymethyl, or a substituent represented by the following general formula (III), (IV), (V) or (VI)

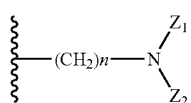

$Z_1$ and $Z_2$ are each independently C1-6 chain alkyl, or
$Z_1$ and $Z_2$ are bonded to each other to form, together with a nitrogen atom linked thereto, a 5- or 6-membered ring; and
n is 1 or 2

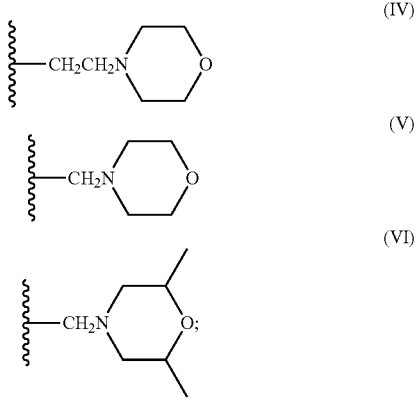

and
R$_4$ is hydrogen, C1-6 alkoxy or halogen.

[Production Method of the Present Compound]

The production method of the present compound is explained below.

The starting materials and reagents used in the following production methods, and the obtained compounds may each form a salt. Examples of such salt include those similar to the salt of the aforementioned compound of the present invention.

When the present compound obtained is a free compound, it can be converted to a desired salt by a method known per se. Conversely, when the present compound obtained in each step is a salt, it can be converted to a free form or other kind of desired salt by a method known per se.

While the production method of the present compound is not particularly limited, for example, the compound can be produced by subjecting the following compounds (VII) and (VIII) to an addition cyclization reaction to form a triazole ring.

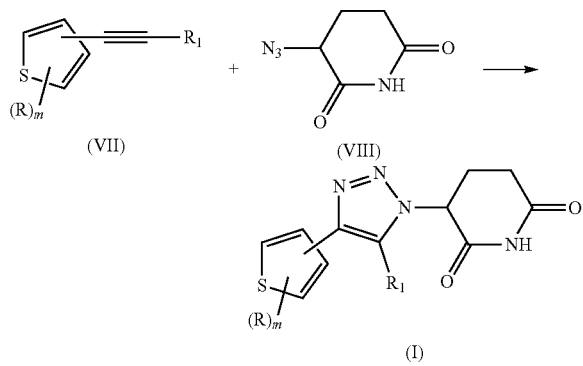

wherein R, R$_1$ and m are as defined above.

The reaction can be performed by reacting compound (VII) and compound (VIII) under stirring in a solution state or suspension state using a suitable solvent that does not adversely influence the reaction. Examples of such suitable solvent include ether (e.g., tetrahydrofuran etc.), acetonitrile, alcohol (e.g., tert-butyl alcohol etc.), water and the like.

The reaction can also be performed in the presence of a suitable catalyst. Examples of such catalyst include copper compounds (e.g., copper(I) iodide, copper(II) acetate, copper(II) sulfate), ruthenium compounds (e.g., chloro(pentamethylcyclopentadienyl)(cyclooctadiene)ruthenium (II)) and the like.

While the reaction temperature is not particularly limited, for example, the reaction can be performed at room temperature to under heating.

Those skilled in the art can appropriately determine various conditions of the above-mentioned reaction.

When compound (VII) or compound (VIII) used as the starting compound in the present production method is commercially available, the commercially available product can be used, or can be appropriately obtained by producing from a known compound by a method known per se, a method disclosed in the section of Examples below, or a method analogous thereto.

The present compound may be a crystal. The crystal of the present compound can be produced by crystallizing the present compound by applying a crystallization method known per se. Examples of the crystallization method include a crystallization method from a solution, a crystallization method from a vapor, a crystallization method from a molten form and the like. Furthermore, the present compound may be a pharmaceutically acceptable cocrystal or cocrystal salt. Here, the cocrystal or cocrystal salt means a crystalline substance composed of two or more unique solids at room temperature, each having different physical properties (e.g., structure, melting point, melting heat, hygroscopicity, solubility, stability etc.). The cocrystal or cocrystal salt can be produced according to a cocrystallization method known per se.

The present compound may be any of hydrate, non-hydrate, solvate, and non-solvate.

[Use of the Present Compound]

The present compound has superior TNF-α production suppressive activity and hematologic cancer cell growth inhibitory activity, and is thus useful, for example, as a safe medicament based on these activities. The medicament of the present invention containing the present compound is expected to show low toxicity (e.g., acute toxicity, chronic toxicity, genetic toxicity, cardiotoxicity, carcinogenicity, etc.), and can be used as a prophylactic or therapeutic agent for, for example, inflammatory disease, autoimmune disease, hematologic cancer and the like in mammals (e.g., mouse, rat, hamster, rabbit, cat, dog, bovine, sheep, monkey, human etc.).

Examples of the "inflammatory disease, autoimmune disease" include rheumatoid arthritis, Crohn's disease, multiple sclerosis, ulcerative colitis, systemic lupus erythematosus, erythema nodosum leprosum, osteoarthritis, gouty arthritis, rheumatoid spondylitis, autoimmune diabetes and the like.

Examples of the "hematologic cancer" include leukemia, malignant lymphoma, multiple myeloma and the like. Leukemia is classified into, but not limited to, acute leukemia and chronic leukemia. Acute leukemia includes, but not limited to, acute myeloid leukemia, acute lymphocytic leukemia/lymphoblastic lymphoma, and acute promyelocytic leukemia. Chronic leukemia includes, but is not limited to, chronic myeloid leukemia, chronic lymphocytic leukemia/small lymphocytic lymphoma. Malignant lymphoma is classified into Hodgkin's lymphoma and non-Hodgkin's lymphoma. Hodgkin's lymphoma is further classified into classical Hodgkin's lymphoma and nodular lymphocyte-predominant Hodgkin's lymphoma. Non-Hodgkin's lymphoma is further classified into precursor lymphoid neoplasms, mature B-cell neoplasm and mature T/NK-cell neoplasm. Precursor lymphoid neoplasm is classified into B-cell lymphoblastic leukemia/lymphoma, T-cell lymphoblastic leukemia/lymphoma. Mature B-cell neoplasm includes, but is not limited to, chronic lymphocytic leukemia/small lymphocytic lymphoma, follicular lymphoma, MALT lymphoma, lymphoplasmacytic lymphoma, mantle cell lymphoma, diffuse large B-cell lymphoma, Burkitt lymphoma and the like. Mature T/NK-cell neoplasm includes, but is not limited to, peripheral T-cell lymphoma, adult T-cell leukemia/lymphoma, extranodal NK/T-cell lymphoma, extranodal nose type NK/T-cell lymphoma, fungoid mycosis, Sezary syndrome and the like.

As used herein, the "prevention" includes prevention of the onset of a disease (all or one or more pathological conditions) and delay of the onset of the disease. The "prophylactically effective amount" refers to a dose of the present compound that is sufficient to achieve the purpose. The "treatment" includes healing of a disease (all or one or more pathological conditions), improvement of the disease, and suppression of progression of the disease severity. The "therapeutically effective amount" means a dose of the present compound sufficient to achieve the purpose.

When the present compound is used as a medicament, the present compound can be used alone or as a pharmaceutical composition of the present compound in combination with a pharmaceutically acceptable carrier widely used in the pharmaceutical field according to a method known per se as a method for producing a pharmaceutical preparation (e.g., the method described in the Japanese Pharmacopoeia, etc.). The pharmaceutical composition is mixed with a carrier, and an excipient, a diluent, a solubilizing agent, etc., which are generally used in the pharmaceutical field, within a range where the desired effect of the present invention is not impaired, and can be administered orally or parenterally in the form of a tablet, powder, granule, capsule, syrup, solution, injection, or the like. The dosage form can be appropriately determined by those skilled in the art according to the intended use of the present compound. The dose varies depending on the patient's symptoms, age, body weight, and the like. Generally, 0.01-500 mg, preferably 0.05-300 mg, more preferably 0.1-150 mg, further preferably 0.5-100 mg, can be administered per day to an adult in one to several portions.

EXAMPLE

The present compound is specifically explained in the following; however, it goes without saying that the present invention is not limited thereto.

Example 1 (Compound 1)

3-[4-(4-bromothiophen-3-yl)-1H-1,2,3-triazol-1-yl]piperidine-2,6-dione (1-1) To an acetone/water (2:1) mixture (120 mL) were added 3-bromopiperidine-2,6-dione (9.74 g, 50.73 mmol) and sodium azide (16.51 g, 253.96 mmol) and the mixture was stirred under an argon atmosphere at room temperature for 24 hr. Acetone was evaporated, and the remaining solution was extracted with ethyl acetate. The organic layer was washed with water and saturated brine, dried over anhydrous magnesium sulfate, treated with activated carbon and concentrated. The concentrated residue was recrystallized from ethyl acetate to give 3-azidopiperidine-2,6-dione (6.26 g, 80%) as a gray solid.

$^1$H-NMR (DMSO-$d_6$) δ 11.06 (1H, brs), 4.57 (1H, dd, J=5.4, 11.9 Hz), 2.45-2.66 (2H, m), 1.99-2.10 (1H, m), 1.78-1.93 (1H, m).

(1-2) To a solution of 3-bromo-4-ethynylthiophene (0.23 g, 1.23 mmol) in acetonitrile (6 mL) were added 3-azidopiperidine-2,6-dione (synthesized by the method of Example 1 (1-1)) (0.19 g, 1.23 mmol) and copper(I) iodide (23.4 mg, 0.12 mmol) and the mixture was stirred under an argon atmosphere at room temperature for 48 hr. The reaction mixture was concentrated, and the concentrated residue was purified by column chromatography (dichloromethane/methanol) to give 3-[4-(4-bromothiophen-3-yl)-1H-1,2,3-triazol-1-yl]piperidine-2,6-dione (0.15 g, 36%) as a white solid.

$^1$H-NMR (DMSO-$d_6$) δ 11.17-11.31 (1H, br), 8.66 (1H, s), 8.05 (1H, d, J=3.5 Hz), 7.87 (1H, d, J=3.5 Hz), 5.90 (1H, dd, J=5.2, 12.6 Hz), 2.65-2.96 (3H, m), 2.29-2.39 (1H, m).

Example 2 (Compound 2)

3-[4-(thiophen-3-yl)-1H-1,2,3-triazol-1-yl]piperidine-2,6-dione

By a method similar to that in Example 1 (1-2), 3-[4-(thiophen-3-yl)-1H-1,2,3-triazol-1-yl]piperidine-2,6-dione (99 mg, 58%) was obtained as a white solid from 3-ethynylthiophene (70 mg, 0.65 mmol).

$^1$H-NMR (DMSO-$d_6$) δ 11.27 (1H, s), 8.54 (1H, s), 7.87 (1H, dd, J=1.2, 2.9 Hz), 7.67 (1H, dd, J=3.0, 5.0 Hz), 7.52 (1H, dd, J=1.2, 5.0 Hz), 5.85 (1H, dd, J=5.2, 12.8 Hz), 2.84-2.95 (1H, m), 2.61-2.75 (2H, m), 2.32-2.41 (1H, m).

Example 3 (Compound 3)

3-[4-(thiophen-2-yl)-1H-1,2,3-triazol-1-yl]piperidine-2,6-dione

To a solution of trimethyl(thiophen-2-ylethynyl)silane (560 mg, 3.11 mmol) in methanol (6 mL) was added potassium carbonate (858 mg, 6.21 mmol) and the mixture was stirred at room temperature for 1 hr. Water was added to the reaction mixture and the mixture was extracted with diethyl ether. The organic layer was washed with saturated brine, dried over anhydrous sodium sulfate and concentrated to give a colorless oil (350 mg). To a solution of the obtained colorless oil (350 mg) in acetonitrile (3 mL) were added 3-azidopiperidine-2,6-dione (synthesized by the method of Example 1 (1-1)) (479 mg, 3.11 mmol) and copper(I) iodide (59.1 mg, 0.31 mmol) and the mixture was stirred at room temperature for 20 hr. The precipitate was collected by filtration and washed with methanol to give 3-[4-(thiophen-2-yl)-1H-1,2,3-triazol-1-yl]piperidine-2,6-dione (429 mg, 53%) as a gray solid.

$^1$H-NMR (DMSO-$d_6$) δ 11.28 (1H, brs), 8.60 (1H, s), 7.56 (1H, dd, J=0.8, 5.0 Hz), 7.44 (1H, d, J=2.9 Hz), 7.15 (1H, dd, J=3.6, 5.0 Hz), 5.86 (1H, d, J=8.2 Hz), 2.80-2.98 (1H, m), 2.60-2.80 (2H, m), 2.30-2.45 (1H, m).

Example 4 (Compound 4)

3-[5-chloro-4-(thiophen-3-yl)-1H-1,2,3-triazol-1-yl]piperidine-2,6-dione

To a solution of 3-ethynylthiophene (0.80 mL, 8.04 mmol) in tetrahydrofuran (12 mL) was added dropwise 1.64 M n-butyl lithium/hexane solution (5.60 mL, 9.18 mmol) at −78° C., and the mixture was stirred at −78° C. for 1 hr. To the reaction mixture was added dropwise a suspension of N-chlorosuccinimide (2.37 g, 17.75 mmol) in tetrahydrofuran (30 mL), and the mixture was stirred at −78° C. to room temperature for 19.5 hr. To the reaction mixture was added hexane, and the mixture was washed with saturated brine and 1.0 M aqueous sodium thiosulfate, dried over anhydrous magnesium sulfate and concentrated. The concentrated residue was purified by column chromatography (hexane/dichloromethane) to give 3-(chloroethynyl)thiophene mixture (723.3 mg) as a pale-yellow oil.

To a solution of the obtained mixture (723.3 mg) in acetonitrile (8 mL) were added 3-azidopiperidine-2,6-dione (624.7 mg, 4.05 mmol) and chloro(pentamethylcyclopentadienyl)(cyclooctadiene)ruthenium (II) (78.7 mg, 0.21 mmol), and the mixture was stirred at 70° C. for 20 days. The reaction mixture was concentrated, and the concentrated residue was purified by column chromatography (hexane/ethyl acetate) to give a crude product (137.6 mg). The obtained crude product was washed with ethyl acetate and chloroform to give 3-[5-chloro-4-(thiophen-3-yl)-1H-1,2,3-triazol-1-yl]piperidine-2,6-dione (44.6 mg, 2%) as a gray solid.

$^1$H-NMR (DMSO-d$_6$) δ 11.34 (1H, brs), 8.03 (1H, dd, J=1.3, 2.9 Hz), 7.76 (1H, dd, J=2.9, 5.0 Hz), 7.64 (1H, dd, J=1.3, 5.0 Hz), 5.88 (1H, dd, J=5.1, 12.5 Hz), 2.69-3.01 (3H, m), 2.38-2.47 (1H, m).

Example 5 (Compound 5)

3-[4-(5-methylthiophen-2-yl)-1H-1,2,3-triazol-1-yl]piperidine-2,6-dione (5-1) To a solution of 2-bromo-5-methylthiophene (500 mg, 2.82 mmol) in triethylamine (3 mL) were added trimethylsilylacetylene (333 mg, 3.39 mmol), copper(I) iodide (53.8 mg, 0.28 mmol) and bis(triphenylphosphine)palladium(II) dichloride (99.1 mg, 0.14 mmol) and the mixture was stirred using a microwave reactor at 80° C. for 1 hr. The reaction mixture was purified by column chromatography to give trimethyl[(5-methylthiophen-2-yl)ethynyl]silane (539 mg, 98%) as an orange oil.

$^1$H-NMR (CDCl$_3$) δ 7.23 (1H, d, J=1.4 Hz), 6.76-6.78 (1H, m), 2.43 (3H, d, J=1.0 Hz), 0.22 (9H, s).

(5-2) By a method similar to that in Example 3, 3-[4-(5-methylthiophen-2-yl)-1H-1,2,3-triazol-1-yl]piperidine-2,6-dione (291 mg, 38%) was obtained as a gray solid from trimethyl[(5-methylthiophen-2-yl)ethynyl]silane (539 mg, 2.77 mmol).

$^1$H-NMR (DMSO-d$_6$) δ 11.26 (1H, s), 8.47 (1H, s), 7.58 (1H, d, J=1.3 Hz), 7.19-7.23 (1H, m), 5.83 (1H, dd, J=5.0, 12.4 Hz), 2.89 (1H, ddd, J=4.0, 12.8, 17.6 Hz), 2.58-2.77 (2H, m), 2.49 (3H, d, J=0.9 Hz), 2.29-2.41 (1H, m).

Example 6 (Compound 6)

3-[4-(5-methylthiophen-3-yl)-1H-1,2,3-triazol-1-yl]piperidine-2,6-dione

By a method similar to that in Example 5, 3-[4-(5-methylthiophen-3-yl)-1H-1,2,3-triazol-1-yl]piperidine-2,6-dione was obtained as a pale-blue solid (16% yield) from 4-bromo-2-methylthiophene.

trimethyl[(5-methylthiophen-3-yl)ethynyl]silane $^1$H-NMR (CDCl$_3$) δ 7.23 (1H, d, J=1.3 Hz), 6.75-6.80 (1H, m), 2.43 (3H, d, J=1.0 Hz), 0.23 (9H, s).

3-[4-(5-methylthiophen-3-yl)-1H-1,2,3-triazol-1-yl]piperidine-2,6-dione $^1$H-NMR (DMSO-d$_6$) δ 11.26 (1H, s), 8.47 (1H, s), 7.58 (1H, d, J=1.4 Hz), 7.21 (1H, brt, J=1.2 Hz), 5.83 (1H, dd, J=5.1, 12.5 Hz), 2.84-2.94 (1H, m), 2.60-2.74 (2H, m), 2.30-2.40 (1H, m), 2.09 (3H, s).

Example 7 (Compound 7)

3-[4-(4-methylthiophen-3-yl)-1H-1,2,3-triazol-1-yl]piperidine-2,6-dione (7-1) By a method similar to that in Example 5 (5-1), trimethyl[(4-methylthiophen-3-yl)ethynyl]silane (293 mg, 54%) was obtained as a yellow oil from 3-bromo-4-methylthiophene (500 mg, 2.82 mmol).

$^1$H-NMR (CDCl$_3$) δ 7.41 (1H, d, J=3.1 Hz), 6.84-6.89 (1H, m), 2.27 (3H, d, J=1.0 Hz), 0.24 (9H, s).

(7-2) To a solution of trimethyl[(4-methylthiophen-3-yl)ethynyl]silane (423 mg, 2.18 mmol) in methanol (6 mL) was added potassium carbonate (601.6 mg, 4.35 mmol) and the mixture was stirred at room temperature for 23 hr. The reaction mixture was filtered, and the filtrate was concentrated. The concentrated residue was purified by column chromatography (hexane) to give a yellow oil (180 mg). By a method similar to that in Example 1 (1-2), 3-[4-(4-methylthiophen-3-yl)-1H-1,2,3-triazol-1-yl]piperidine-2,6-dione (117 mg, 19%) was obtained as a white amorphous-like substance from the obtained oil (180 mg).

$^1$H-NMR (DMSO-d$_6$) δ 11.26 (1H, s), 8.47 (1H, s), 7.80 (1H, d, J=3.3 Hz), 7.27-7.31 (1H, m), 5.86 (1H, dd, J=5.0, 12.5 Hz), 2.84-2.97 (1H, m), 2.65-2.79 (2H, m), 2.31-2.40 (4H, m).

Example 8 (Compound 8)

3-[4-(5-acetylthiophen-2-yl)-1H-1,2,3-triazol-1-yl]piperidine-2,6-dione (8-1) To a solution of 2-acetyl-5-bromothiophene (0.50 g, 2.44 mmol) in tetrahydrofuran (5 mL) were added diisopropylamine (0.51 ml, 3.63 mmol), trimethylsilylacetylene (0.37 mL, 2.67 mmol), bis(triphenylphosphine)palladium (II) dichloride (86 mg, 0.12 mmol) and copper(I) iodide (12 mg, 0.06 mmol), and the mixture was sealed under an argon atmosphere and stirred at room temperature for 17 hr. To the reaction mixture was added water and the mixture was extracted with dichloromethane. The organic layer was washed with water and saturated brine, dried over anhydrous magnesium sulfate and concentrated to give 1-{5-[(trimethylsilyl)ethynyl]thiophen-2-yl}ethanone mixture (0.64 g) as a brown solid. The obtained mixture was used for the next reaction without purification.

$^1$H-NMR (CDCl$_3$) δ 7.53 (1H, d, J=4.0 Hz), 7.19 (1H, d, J=4.0 Hz), 2.54 (3H, s), 0.26 (9H, s).

(8-2) To a solution of 1-{5-[(trimethylsilyl)ethynyl]thiophen-2-yl}ethanone mixture (0.64 g) in methanol (6 mL) was added potassium carbonate (0.80 g, 5.80 mmol) and the mixture was stirred under an argon atmosphere at room temperature for 1 hr. The reaction mixture was filtered through celite, and the filtrate was concentrated. Water was added to the concentrated residue and extracted with diethyl ether. The organic layer was washed with water and saturated brine, dried over anhydrous magnesium sulfate and concentrated to give 1-(5-ethynylthiophen-2-yl)ethanone (0.19 g, 2 steps 52%) as a brown solid.

$^1$H-NMR (CDCl$_3$) δ 7.54 (1H, d, J=4.0 Hz), 7.25 (1H, d, J=4.0 Hz), 3.51 (1H, s), 2.55 (3H, s).

(8-3) By a method similar to that in Example 1 (1-2), 3-[4-(5-acetylthiophen-2-yl)-1H-1,2,3-triazol-1-yl]piperidine-2,6-dione (70.6 mg, 18%) was obtained as a pale-brown solid from 1-(5-ethynylthiophen-2-yl)ethanone (0.19 g, 1.26 mmol).

$^1$H-NMR (DMSO-d$_6$) δ 11.31 (1H, s), 8.81 (1H, s), 7.96 (1H, d, J=4.0 Hz), 7.56 (1H, d, J=3.9 Hz), 5.90 (1H, dd, J=5.2, 12.8 Hz), 2.83-2.96 (1H, m), 2.58-2.77 (2H, m), 2.55 (3H, s), 2.34-2.43 (1H, m).

Example 9 (Compound 9)

3-{4-[5-(hydroxymethyl)thiophen-3-yl]-1H-1,2,3-triazol-1-yl}piperidine-2,6-dione By a method similar to that in Example 1 (1-2), 3-{4-[5-(hydroxymethyl)thiophen-3-yl]-1H-1,2,3-triazol-1-yl}piperidine-2,6-dione (0.33 g, 29%) was obtained as a pale-purple solid from (4-ethynylthiophen-2-yl)methanol (0.53 g, 3.84 mmol).

$^1$H-NMR (DMSO-d$_6$) δ 11.26 (1H, s), 8.50 (1H, s), 7.72 (1H, d, J=1.4 Hz), 7.32-7.38 (1H, m), 5.84 (1H, dd, J=5.2, 12.6 Hz), 5.55 (1H, t, J=5.8 Hz), 4.66 (2H, dd, J=0.7, 5.8 Hz), 2.82-2.96 (1H, m), 2.60-2.77 (2H, m), 2.30-2.41 (1H, m).

Example 10 (Compound 10)

3-[4-(2,3-dihydrothieno[3,4-b][1,4]dioxin-5-yl)-1H-1,2,3-triazol-1-yl]piperidine-2,6-dione By a method similar to that in Example 1 (1-2), 3-[4-(2,3-dihydrothieno[3,4-b][1,4]dioxin-5-yl)-1H-1,2,3-triazol-1-yl]piperidine-2,6-dione (0.87 g, 33%) was obtained as a gray solid from 5-ethynyl-2,3-dihydrothieno[3,4-b][1,4]dioxin (1.36 g, 8.18 mmol).

$^1$H-NMR (DMSO-d$_6$) δ 11.23 (1H, s), 8.33 (1H, s), 6.62 (1H, s), 5.87 (1H, dd, J=5.1, 12.4 Hz), 4.20-4.40 (4H, m), 2.62-2.95 (3H, m), 2.23-2.36 (1H, m).

Example 11 (Compound 11)

3-[4-(5-chlorothiophen-2-yl)-1H-1,2,3-triazol-1-yl]piperidine-2,6-dione (11-1) To a solution of 2-bromo-5-chlorothiophene (0.50 g, 2.53 mmol) in THF (5 ml) were added diisopropylamine (0.53 ml, 3.77 mmol), bis(triphenylphosphine)palladium(II) dichloride (88.9 mg, 0.13 mmol), copper(I) iodide (12.1 mg, 0.06 mmol), and trimethylsilylacetylene (0.37 ml, 2.67 mmol), and the mixture was sealed under an argon atmosphere and stirred at 80° C. for 5 hr. To the reaction mixture was added saturated aqueous ammonium chloride and the mixture was extracted with diethyl ether. The organic layer was washed with saturated brine, dried over anhydrous magnesium sulfate and concentrated. The concentrated residue was purified by column chromatography (hexane) to give [(5-chlorothiophen-2-yl)ethynyl]trimethylsilane (0.51 g, 94%) as a pale-yellow oil.

$^1$H-NMR (CDCl$_3$) δ 6.99 (1H, d, J=3.9 Hz), 6.76 (1H, d, J=3.9 Hz), 0.24 (9H, s).

(11-2) By a method similar to that in Example 8 (8-2, 8-3), 3-[4-(5-chlorothiophen-2-yl)-1H-1,2,3-triazol-1-yl]piperidine-2,6-dione as a gray solid (23% yield) from [(5-chlorothiophen-2-yl)ethynyl]trimethylsilane.

2-chloro-5-ethynylthiophene $^1$H-NMR (CDCl$_3$) δ 7.05 (1H, d, J=3.8 Hz), 6.79 (1H, d, J=3.9 Hz), 3.32 (1H, s).

3-[4-(5-chlorothiophen-2-yl)-1H-1,2,3-triazol-1-yl]piperidine-2,6-dione $^1$H-NMR (DMSO-d$_6$) δ 11.28 (1H, s), 8.64 (1H, s), 7.32 (1H, d, J=3.9 Hz), 7.17 (1H, d, J=3.9 Hz), 5.87 (1H, dd, J=5.1, 12.6 Hz), 2.82-2.95 (1H, m), 2.60-2.75 (2H, m), 2.31-2.41 (1H, m).

Example 12 (Compound 12)

3-[4-(5-bromothiophen-2-yl)-1H-1,2,3-triazol-1-yl]piperidine-2,6-dione

By a method similar to that in Example 1 (1-2), 3-[4-(5-bromothiophen-2-yl)-1H-1,2,3-triazol-1-yl]piperidine-2,6-dione (101.7 mg, 43%) was obtained as a gray solid from 2-bromo-5-ethynylthiophene (0.13 g, 0.69 mmol).

$^1$H-NMR (DMSO-d$_6$) δ 11.28 (1H, s), 8.64 (1H, s), 7.29 (1H, d, J=3.9 Hz), 7.27 (1H, d, J=3.8 Hz), 5.87 (1H, dd, J=5.2, 12.6 Hz), 2.82-2.95 (1H, m), 2.60-2.76 (2H, m), 2.31-2.42 (1H, m).

Example 13 (Compound 13)

3-[4-(2,5-dibromothiophen-3-yl)-1H-1,2,3-triazol-1-yl]piperidine-2,6-dione (13-1) To a solution of 2,5-dibromothiophene-3-carboxyaldehyde (0.34 g, 1.26 mmol) and dimethyl (1-diazo-2-oxopropyl)phosphonate (0.32 g, 1.67 mmol) in methanol (13 mL) was added potassium carbonate (0.35 g, 2.53 mmol) and the mixture was stirred under an argon atmosphere at room temperature for 20 hr. The reaction mixture was concentrated, and the concentrated residue was purified by column chromatography (hexane/ethyl acetate) to give 2,5-dibromo-3-ethynylthiophene (0.30 g, 90%) as a pale-brown solid.

$^1$H-NMR (CDCl$_3$) δ 6.97 (1H, s), 3.30 (1H, s).

(13-2) By a method similar to that in Example 1 (1-2), 3-[4-(2,5-dibromothiophen-3-yl)-1H-1,2,3-triazol-1-yl]piperidine-2,6-dione (241.4 mg, 51%) was obtained as a pale-brown solid from 2,5-dibromo-3-ethynylthiophene (297.5 mg, 1.12 mmol).

$^1$H-NMR (DMSO-d$_6$) δ 11.28 (1H, s), 8.79 (1H, s), 7.64 (1H, s), 5.92 (1H, dd, J=5.4, 12.8 Hz), 2.83-2.96 (1H, m), 2.64-2.83 (2H, m), 2.30-2.40 (1H, m).

Example 14 (Compound 14)

3-[4-(4-chlorothiophen-3-yl)-1H-1,2,3-triazol-1-yl]piperidine-2,6-dione

By a method similar to that in Example 1 (1-2), 3-[4-(4-chlorothiophen-3-yl)-1H-1,2,3-triazol-1-yl]piperidine-2,6-dione (67.8 mg, 51%) was obtained as a white solid from 3-chloro-4-ethynylthiophene (64.1 mg, 0.45 mmol).

$^1$H-NMR (DMSO-d$_6$) δ 11.26 (1H, s) 8.65 (1H, s), 8.10 (1H, d, J=3.6 Hz), 7.77 (1H, d, J=3.6 Hz), 5.90 (1H, dd, J=5.1, 12.5 Hz), 2.65-2.95 (3H, m), 2.30-2.40 (1H, m).

Example 15 (Compound 15)

3-[4-(4-methoxy-5-methylthiophen-3-yl)-1H-1,2,3-triazol-1-yl]piperidine-2,6-dione (15-1) Under an argon atmosphere, to a suspension of lithium aluminum hydride (0.36 g, 9.49 mmol) in diethyl ether (80 mL) was added dropwise a solution of methyl 4-bromo-3-methoxythiophene-2-carboxylate (2.01 g, 8.00 mmol) in diethyl ether (14 mL) at not more than 5° C., and the mixture was stirred at 0° C. for 2 hr. To the reaction mixture was added water and the mixture was filtered through celite. Water was added to the filtrate and the mixture was extracted with diethyl ether. The organic layer was washed with saturated brine, dried over anhydrous magnesium sulfate and concentrated. The concentrated residue was purified by column chromatography (dichloromethane/methanol) to give (4-bromo-3-methoxythiophen-2-yl)methanol (1.29 g, 72%) as a brown oil.

$^1$H-NMR (CDCl$_3$) δ 7.15 (1H, s), 4.77 (2H, d, J=5.8 Hz), 3.90 (3H, s), 1.92 (1H, t, J=5.9 Hz).

(15-2) To a solution of (4-bromo-3-methoxythiophen-2-yl)methanol (1.29 g, 5.78 mmol) in dichloromethane (12 mL) was added thionyl chloride (0.50 mL, 6.89 mmol) at 0° C. and the mixture was stirred under an argon atmosphere at room temperature for 4.5 hr. After 2 hr and 3 hr, thionyl chloride (0.25 mL, 3.45 mmol) was added at 0° C. To the reaction mixture was added water at 0° C. and the mixture was extracted with dichloromethane. The organic layer was washed with saturated brine, dried over anhydrous magnesium sulfate, treated with activated carbon and concentrated to give 4-bromo-2-(chloromethyl)-3-methoxythiophene (1.32 g, 95%) as a yellow oil. The obtained 4-bromo-2-(chloromethyl)-3-methoxythiophene was used for the next reaction without purification.

$^1$H-NMR (CDCl$_3$) δ 7.20 (1H, s), 4.74 (2H, s), 3.94 (3H, s).

(15-3) Under an argon atmosphere, to a suspension of lithium aluminum hydride (0.24 g, 6.32 mmol) in tetrahydrofuran (55 mL) was added dropwise a solution of 4-bromo-2-(chloromethyl)-3-methoxythiophene (1.32 g, 5.47 mmol) in tetrahydrofuran (10 mL) at not more than 5° C., and the mixture was stirred at 0° C. for 5 hr. To the reaction mixture was added water and the mixture was filtered through celite. Water was added to the filtrate and the mixture was extracted with ethyl acetate. The organic layer was washed with saturated brine, dried over anhydrous magnesium sulfate and concentrated. The concentrated residue was purified by column chromatography (hexane/dichloromethane) to give 4-bromo-3-methoxy-2-methylthiophene (0.72 g, 64%) as a colorless oil.

$^1$H-NMR (CDCl$_3$) δ 6.95 (1H, s), 3.81 (3H, s), 2.37 (3H, s).

(15-4) By a method similar to that in Example 11, 3-[4-(4-methoxy-5-methylthiophen-3-yl)-1H-1,2,3-triazol-1-yl]piperidine-2,6-dione was obtained as a gray solid (34% yield) from 4-bromo-3-methoxy-2-methylthiophene. [(4-methoxy-5-methylthiophen-3-yl)ethynyl]trimethylsilane $^1$H-NMR (CDCl$_3$) δ 7.13 (1H, s), 3.90 (3H, s), 2.28 (3H, s), 0.24 (9H, s).

4-ethynyl-3-methoxy-2-methylthiophene $^1$H-NMR (CDCl$_3$) δ 7.18 (1H, s), 3.90 (3H, s), 3.16 (1H, s), 2.31 (3H, s).

3-[4-(4-methoxy-5-methylthiophen-3-yl)-1H-1,2,3-triazol-1-yl]piperidine-2,6-dione $^1$H-NMR (DMSO-d$_6$) δ 11.23 (1H, brs), 8.35 (1H, s), 7.60 (1H, s), 5.86 (1H, dd, J=5.1, 12.4 Hz), 3.73 (3H, s), 2.63-2.96 (3H, m), 2.25-2.41 (4H, m).

Example 16 (Compound 16)

methyl 4-[1-(2,6-dioxopiperidin-3-yl)-1H-1,2,3-triazol-4-yl]-3-methoxythiophene-2-carboxylate By a method similar to that in Example 11, methyl 4-[1-(2,6-dioxopiperidin-3-yl)-1H-1,2,3-triazol-4-yl]-3-methoxythiophene-2-carboxylate was obtained as a gray solid (36% yield) from methyl 4-bromo-3-methoxythiophene-2-carboxylate.

methyl 3-methoxy-4-[(trimethylsilyl)ethynyl]thiophene-2-carboxylate $^1$H-NMR (CDCl$_3$) δ 7.50 (1H, s), 4.13 (3H, s), 3.86 (3H, s), 0.24 (9H, s).

methyl 4-ethynyl-3-methoxythiophene-2-carboxylate $^1$H-NMR (CDCl$_3$) δ 7.56 (1H, s), 4.13 (3H, s), 3.87 (3H, s), 3.21 (1H, s).

methyl 4-[1-(2,6-dioxopiperidin-3-yl)-1H-1,2,3-triazol-4-yl]-3-methoxythiophene-2-carboxylate $^1$H-NMR (DMSO-d$_6$) δ 11.26 (1H, s), 8.48 (1H, s), 8.23 (1H, s), 5.89 (1H, dd, J=5.0, 12.4 Hz), 3.98 (3H, s), 3.83 (3H, s), 2.64-2.97 (3H, m), 2.27-2.38 (1H, m).

Example 17 (Compound 17)

3-[4-(4-ethoxythiophen-3-yl)-1H-1,2,3-triazol-1-yl]piperidine-2,6-dione

By a method similar to that in Example 11, 3-[4-(4-ethoxythiophen-3-yl)-1H-1,2,3-triazol-1-yl]piperidine-2,6-dione was obtained as a pale-brown solid (30% yield) from 3-bromo-4-ethoxythiophene.

[(4-ethoxythiophen-3-yl)ethynyl]trimethylsilane $^1$H-NMR (CDCl$_3$) δ 7.36 (1H, d, J=3.3 Hz), 6.15 (1H, d, J=3.3 Hz), 4.04 (2H, q, J=7.0 Hz), 1.45 (3H, t, J=7.0 Hz), 0.25 (9H, s).

3-ethoxy-4-ethynylthiophene $^1$H-NMR (CDCl$_3$) δ 7.41 (1H, d, J=3.3 Hz), 6.18 (1H, d, J=3.3 Hz), 4.07 (2H, q, J=7.0 Hz), 3.17 (1H, s), 1.46 (3H, t, J=7.0 Hz).

3-[4-(4-ethoxythiophen-3-yl)-1H-1,2,3-triazol-1-yl]piperidine-2,6-dione $^1$H-NMR (DMSO-d$_6$) δ 11.23 (1H, s), 8.27 (1H, s), 7.88 (1H, d, J=3.4 Hz), 6.73 (1H, d, J=3.4 Hz), 5.88 (1H, dd, J=5.0, 12.3 Hz), 4.11 (2H, q, J=7.0 Hz), 2.64-2.92 (3H, m), 2.26-2.36 (1H, m), 1.42 (3H, t, J=7.0 Hz).

Example 18 (Compound 18)

3-[4-(2-methoxythiophen-3-yl)-1H-1,2,3-triazol-1-yl]piperidine-2,6-dione

By a method similar to that in Example 13, 3-[4-(2-methoxythiophen-3-yl)-1H-1,2,3-triazol-1-yl]piperidine-2, 6-dione was obtained as a gray solid (25% yield) from 2-methoxythiophene-3-carboxyaldehyde.

3-ethynyl-2-methoxythiophene $^1$H-NMR (CDCl$_3$) δ 6.82 (1H, d, J=5.8 Hz), 6.50 (1H, d, J=5.8 Hz), 4.02 (3H, s), 3.21 (1H, s).

3-[4-(2-methoxythiophen-3-yl)-1H-1,2,3-triazol-1-yl]piperidine-2,6-dione $^1$H-NMR (DMSO-d$_6$) δ 11.23 (1H, s), 8.33 (1H, s), 7.35 (1H, d, J=5.8 Hz), 6.94 (1H, d, J=5.8 Hz), 5.85 (1H, dd, J=5.1, 12.5 Hz), 4.00 (3H, s), 2.63-2.94 (3H, m), 2.25-2.35 (1H, m).

Example 19 (Compound 19)

3-[4-(4-methoxythiophen-3-yl)-1H-1,2,3-triazol-1-yl]piperidine-2,6-dione

By a method similar to that in Example 13, 3-[4-(4-methoxythiophen-3-yl)-1H-1,2,3-triazol-1-yl]piperidine-2,6-dione was obtained as a gray solid (64% yield) from 4-methoxythiophene-3-carboxyaldehyde.

3-ethynyl-4-methoxythiophene $^1$H-NMR (CDCl$_3$) δ 7.42 (1H, d, J=3.3 Hz), 6.21 (1H, d, J=3.3 Hz), 3.88 (3H, s), 3.19 (1H, s).

3-[4-(4-methoxythiophen-3-yl)-1H-1,2,3-triazol-1-yl]piperidine-2,6-dione $^1$H-NMR (DMSO-d$_6$) δ 11.23 (1H, s), 8.35 (1H, s), 7.88 (1H, d, J=3.4 Hz), 6.75 (1H, d, J=3.4 Hz), 5.86 (1H, dd, J=5.1, 12.5 Hz), 3.88 (3H, s), 2.63-2.94 (3H, m), 2.27-2.35 (1H, m).

Example 20 (Compound 20)

3-[4-(5-methoxythiophen-3-yl)-1H-1,2,3-triazol-1-yl]piperidine-2,6-dione

By a method similar to that in Example 1 (1-2), 3-[4-(5-methoxythiophen-3-yl)-1H-1,2,3-triazol-1-yl]piperidine-2,6-dione (0.80 g, 59%) was obtained as a pale-brown solid from 4-ethynyl-2-methoxythiophene (0.64 g, 4.63 mmol).

$^1$H-NMR (DMSO-d$_6$) δ 11.26 (1H, s), 8.47 (1H, s), 7.07 (1H, d, J=1.7 Hz), 6.71 (1H, d, J=1.7 Hz), 5.83 (1H, dd, J=5.2, 12.7 Hz), 3.91 (3H, s), 2.82-2.95 (1H, m), 2.59-2.75 (2H, m), 2.30-2.40 (1H, m).

Example 21 (Compound 21)

3-[4-(4-propoxythiophen-3-yl)-1H-1,2,3-triazol-1-yl]piperidine-2,6-dione

By a method similar to that in Example 13, 3-[4-(4-propoxythiophen-3-yl)-1H-1,2,3-triazol-1-yl]piperidine-2,6-dione was obtained as a pale-brown solid (50% yield) from 4-propoxythiophene-3-carboxyaldehyde.

3-ethynyl-4-propoxythiophene $^1$H-NMR (CDCl$_3$) δ 7.40 (1H, d, J=3.3 Hz), 6.17 (1H, d, J=3.3 Hz), 3.95 (2H, t, J=6.6 Hz), 3.16 (1H, s), 1.80-1.91 (2H, m), 1.04 (3H, t, J=7.4 Hz).

3-[4-(4-propoxythiophen-3-yl)-1H-1,2,3-triazol-1-yl]piperidine-2,6-dione $^1$H-NMR (DMSO-d$_6$) δ 11.23 (1H, s), 8.22 (1H, s), 7.88 (1H, d, J=3.3 Hz), 6.73 (1H, d, J=3.4 Hz), 5.88 (1H, dd, J=5.0, 12.4 Hz), 3.97-4.06 (2H, m), 2.65-2.93 (3H, m), 2.28-2.38 (1H, m), 1.77-1.89 (2H, m), 1.01 (3H, t, J=7.4 Hz).

Example 22 (Compound 22)

3-[4-(5-chloro-4-methoxythiophen-3-yl)-1H-1,2,3-triazol-1-yl]piperidine-2,6-dione (22-1) To a solution of 4-methoxythiophene-3-carboxyaldehyde (200 mg, 1.41 mmol) in chloroform (1.4 mL) was added 2-chloro-1,3-bis(methoxycarbonyl)guanidine (354.3 mg, 1.69 mmol) and the mixture was stirred under an argon atmosphere at room temperature for 30 hr. The reaction mixture was concentrated, and the concentrated residue was purified by column chromatography (hexane/ethyl acetate) to give 5-chloro-4-methoxythiophene-3-carboxyaldehyde (151 mg, 60%) as a yellow oil.

$^1$H NMR (CDCl$_3$) δ 9.80 (1H, s), 7.83 (1H, s), 4.03 (3H, s).

(22-2) By a method similar to that in Example 13, 3-[4-(5-chloro-4-methoxythiophen-3-yl)-1H-1,2,3-triazol-1-yl]piperidine-2,6-dione was obtained as a white solid (49% yield) from 5-chloro-4-methoxythiophene-3-carboxyaldehyde.

2-chloro-4-ethynyl-3-methoxythiophene $^1$H NMR (CDCl$_3$) δ 7.21 (1H, s), 4.01 (3H, s), 3.19 (1H, s).

3-[4-(5-chloro-4-methoxythiophen-3-yl)-1H-1,2,3-triazol-1-yl]piperidine-2,6-dione $^1$H-NMR (DMSO-d$_6$) δ 11.25 (1H, s), 8.44 (1H, s), 7.81 (1H, s), 5.88 (1H, dd, J=5.1, 12.5 Hz), 3.90 (3H, s), 2.65-2.95 (3H, m), 2.27-2.37 (1H, m).

Example 23 (Compound 23)

3-[4-(5-bromo-4-methoxythiophen-3-yl)-1H-1,2,3-triazol-1-yl]piperidine-2,6-dione (23-1) To a solution of 4-methoxythiophene-3-carboxyaldehyde (0.10 g, 0.70 mmol) in dichloromethane (1 mL) was added N-bromosuccinimide (131.6 mg, 0.74 mmol) by small portions at 0° C., and the mixture was stirred at 0° C. for 1 hr. The reaction mixture was concentrated, and the concentrated residue was purified by column chromatography (hexane/ethyl acetate) to give 5-bromo-4-methoxythiophene-3-carboxyaldehyde (0.16 g) as a pale-brown oil. The obtained 5-bromo-4-methoxythiophene-3-carboxyaldehyde was used for the next reaction without purification.

¹H-NMR (CDCl₃) δ 9.81 (1H, s), 8.00 (1H, s), 4.01 (3H, s).
(23-2) By a method similar to that in Example 13, 3-[4-(5-bromo-4-methoxythiophen-3-yl)-1H-1,2,3-triazol-1-yl]piperidine-2,6-dione was obtained as a white solid (46% yield) from 5-bromo-4-methoxythiophene-3-carboxyaldehyde.

2-bromo-4-ethynyl-3-methoxythiophene

¹H-NMR (CDCl₃) δ 7.39 (1H, s), 4.00 (3H, s), 3.20 (1H, s).
3-[4-(5-bromo-4-methoxythiophen-3-yl)-1H-1,2,3-triazol-1-yl]piperidine-2,6-dione
¹H-NMR (DMSO-d₆) δ 11.24 (1H, s), 8.44 (1H, s), 7.96 (1H, s), 5.88 (1H, dd, J=5.1, 12.5 Hz), 3.86 (3H, s), 2.65-2.96 (3H, m), 2.27-2.38 (1H, m).

Example 24 (Compound 24)

3-[4-(5-ethoxythiophen-3-yl)-1H-1,2,3-triazol-1-yl]piperidine-2,6-dione (24-1) To a solution of 5-bromothiophene-3-carboxyaldehyde (9.96 g, 52.13 mmol) in methanol (78 ml) were added methyl orthoformate (8.56 ml, 78.24 mmol) and ammonium chloride (0.39 g, 7.29 mmol) and the mixture was stirred under an argon atmosphere at 60° C. for 3.5 hr. The reaction mixture was concentrated, diethyl ether was added to the concentrated residue and the mixture was filtered. The filtrate was concentrated, and the concentrated residue was purified by column chromatography (hexane/ethyl acetate) to give 2-bromo-4-(dimethoxymethyl)thiophene (11.80 g, 95%) as a yellow oil.
¹H-NMR (CDCl₃) δ 7.23 (1H, dd, J=1.0, 1.5 Hz), 7.05 (1H, d, J=1.5 Hz), 5.37 (1H, d, J=0.7 Hz), 3.31 (6H, s).
(24-2) To a suspension of sodium hydride (60%) (0.38 g, 9.50 mmol) in N,N-dimethylformamide (1.27 ml) was slowly added ethanol (2.53 ml) and the mixture was stirred at room temperature until foaming ceased. To this solution were added 2-bromo-4-(dimethoxymethyl)thiophene (0.50 g, 2.11 mmol) and copper(I) bromide (15.1 mg, 0.11 mmol) and the mixture was reacted under an argon atmosphere using a microwave reactor at 160° C. for 15 min. The reaction mixture was filtered through celite, and the filtrate was concentrated. The concentrated residue was purified by column chromatography (hexane/ethyl acetate) to give 4-(dimethoxymethyl)-2-ethoxythiophene (0.19 g, 48%) as a yellow oil.
¹H-NMR (CDCl₃) δ 6.56 (1H, dd, J=1.0, 1.6 Hz), 6.19 (1H, d, J=1.6 Hz), 5.28 (1H, d, J=0.7 Hz), 4.08 (2H, q, J=7.0 Hz), 3.32 (6H, s), 1.40 (3H, t, J=7.0 Hz).
(24-3) To a solution of 4-(dimethoxymethyl)-2-ethoxythiophene (0.58 g, 3.11 mmol) in methanol (10 ml) was added 4.0 M hydrochloric acid (10 ml), and the mixture was stirred at room temperature for 20 min. To the reaction mixture was added saturated brine and the mixture was extracted with diethyl ether. The organic layer was washed with saturated brine, dried over anhydrous magnesium sulfate and concentrated. The concentrated residue was purified by column chromatography (hexane/ethyl acetate) to give 5-ethoxythiophene-3-carboxyaldehyde (0.32 g, 66%) as a yellow oil.
¹H-NMR (CDCl₃) δ 9.67 (1H, s), 7.39 (1H, d, J=1.6 Hz), 6.57 (1H, d, J=1.6 Hz), 4.13 (2H, q, J=7.0 Hz), 1.43 (3H, t, J=7.0 Hz).
(24-4) By a method similar to that in Example 13, 3-[4-(5-ethoxythiophen-3-yl)-1H-1,2,3-triazol-1-yl]piperidine-2,6-dione was obtained as a pale-brown solid (46% yield) from 5-ethoxythiophene-3-carboxyaldehyde.

2-ethoxy-4-ethynylthiophene

¹H-NMR (CDCl₃) δ 6.77 (1H, d, J=1.6 Hz), 6.22 (1H, d, J=1.6 Hz), 4.08 (2H, q, J=7.0 Hz), 2.96 (1H, s), 1.41 (3H, t, J=7.0 Hz).

3-[4-(5-ethoxythiophen-3-yl)-1H-1,2,3-triazol-1-yl]piperidine-2,6-dione

¹H-NMR (DMSO-d₆) δ 11.26 (1H, s), 8.46 (1H, s), 7.07 (1H, d, J=1.6 Hz), 6.70 (1H, d, J=1.6 Hz), 5.83 (1H, dd, J=5.0, 12.7 Hz), 4.15 (2H, q, J=7.0 Hz), 2.89 (1H, ddd, J=5.0, 13.1, 18.1 Hz), 2.58-2.75 (2H, m), 2.30-2.40 (1H, m), 1.36 (3H, t, J=7.0 Hz).

Example 25 (Compound 25)

3-[4-(4-butoxythiophen-3-yl)-1H-1,2,3-triazol-1-yl]piperidine-2,6-dione (25-1) To a solution of 3-bromo-4-(diethoxymethyl)thiophene (0.66 g, 2.49 mmol) in 1-methyl-2-pyrrolidone (0.62 ml) were added copper(I) bromide (0.36 g, 2.51 mmol) and sodium 1-butoxide (22.4 w/w % in 1-BuOH) (3.74 g, 8.72 mmol) and the mixture was reacted under an argon atmosphere using a microwave reactor at 160° C. for 15 min. The same reaction was performed for 2 lots, and the reaction mixtures of the both lots were combined and filtered through celite. Saturated brine was added to the filtrate, and the mixture was extracted with diethyl ether. The organic layer was washed with saturated brine, dried over anhydrous magnesium sulfate and concentrated. The concentrated residue was purified by column chromatography (hexane/ethyl acetate) to give 3-butoxy-4-(diethoxymethyl)thiophene (0.95 g, 74%) as a pale-yellow oil.
¹H-NMR (CDCl₃) δ 7.32 (1H, dd, J=0.6, 3.4 Hz), 6.17 (1H, d, J=3.4 Hz), 5.48 (1H, d, J=0.6 Hz), 3.96 (2H, t, J=6.4 Hz), 3.51-3.69 (4H, m), 1.71-1.81 (2H, m), 1.42-1.54 (2H, m), 1.22 (6H, t, J=7.1 Hz), 0.96 (3H, t, J=7.4 Hz).
(25-2) By a method similar to that in Example 24 (24-3, 24-4), 3-[4-(4-butoxythiophen-3-yl)-1H-1,2,3-triazol-1-yl]piperidine-2,6-dione was obtained as a pale-brown solid (54% yield) from 3-butoxy-4-(diethoxymethyl)thiophene.

4-butoxythiophene-3-carboxyaldehyde

¹H-NMR (CDCl₃) δ 9.91 (1H, s), 8.01 (1H, d, J=3.4 Hz), 6.27 (1H, d, J=3.4 Hz), 4.03 (2H, t, J=6.4 Hz), 1.77-1.87 (2H, m), 1.45-1.57 (2H, m), 0.99 (3H, t, J=7.4 Hz).

3-butoxy-4-ethynylthiophene

¹H-NMR (CDCl₃) δ 7.40 (1H, d, J=3.4 Hz), 6.17 (1H, d, J=3.3 Hz), 3.99 (2H, t, J=6.6 Hz), 3.15 (1H, s), 1.76-1.86 (2H, m), 1.44-1.57 (2H, m), 0.98 (3H, t, J=7.4 Hz).

3-[4-(4-butoxythiophen-3-yl)-1H-1,2,3-triazol-1-yl]piperidine-2,6-dione

¹H-NMR (DMSO-d₅) δ 11.23 (1H, s), 8.21 (1H, s), 7.88 (1H, d, J=3.4 Hz), 6.73 (1H, d, J=3.4 Hz), 5.88 (1H, dd, J=5.3, 12.6 Hz), 4.01-4.11 (2H, m), 2.64-2.93 (3H, m), 2.27-2.38 (1H, m), 1.75-1.85 (2H, m), 1.40-1.51 (2H, m), 0.95 (3H, t, J=7.4 Hz).

Example 26 (Compound 26)

3-[4-(4-isopropoxythiophen-3-yl)-1H-1,2,3-triazol-1-yl]piperidine-2,6-dione (26-1) To a suspension of sodium hydride (60%) (0.38 g, 9.50 mmol) in N,N-dimethylformamide (1.27 ml) was slowly added 2-propanol (2.53 ml) and the mixture was stirred at room temperature until foaming ceased. To this solution were added 3-bromo-4-(dimethoxymethyl)thiophene (0.50 g, 2.11 mmol) and copper(I) bromide (0.30 g, 2.09 mmol) and the mixture was reacted under an argon atmosphere using a microwave reactor at 160° C. for 15 min. To the reaction mixture was added diethyl ether (2 ml) and the mixture was filtered through celite. The same reaction was performed for 2 lots, and the filtrates of the both lots were combined. Saturated brine was added to the solution, and the mixture was extracted with diethyl ether. The organic layer was washed with saturated brine, dried over anhydrous magnesium sulfate, treated with activated carbon and concentrated to give a yellow-brown oil (1.49 g). To a solution of the obtained yellow-brown oil (1.49 g) in methanol (10 ml) was added 4.0 M hydrochloric acid (10 ml) and the mixture was stirred under an argon atmosphere at room temperature for 20 min. To the reaction mixture was added saturated brine and the mixture was extracted with diethyl ether. The organic layer was washed with saturated brine, dried over anhydrous magnesium sulfate and concentrated. The concentrated residue was purified by column chromatography (hexane/ethyl acetate) to give 4-isopropoxythiophene-3-carboxyaldehyde mixture (0.65 g) as a yellow oil. The obtained 4-isopropoxythiophene-3-carboxyaldehyde mixture was used for the next reaction without purification.

$^1$H-NMR (CDCl$_3$) δ 9.88 (1H, s), 8.00 (1H, d, J=3.3 Hz), 6.26 (1H, d, J=3.3 Hz), 4.47 (1H, sep, J=6.1 Hz), 1.40 (6H, d, J=6.1 Hz).

(26-2) By a method similar to that in Example 13, 3-[4-(4-isopropoxythiophen-3-yl)-1H-1,2,3-triazol-1-yl]piperidine-2,6-dione was obtained as a gray solid from 4-isopropoxythiophene-3-carboxyaldehyde mixture. (from 3-bromo-4-(dimethoxymethyl)thiophene, 4 steps 16%)

3-ethynyl-4-isopropoxythiophene $^1$H-NMR (CDCl$_3$) δ 7.39 (1H, d, J=3.3 Hz), 6.20 (1H, d, J=3.3 Hz), 4.42 (1H, sep, J=6.1 Hz), 3.15 (1H, s), 1.38 (6H, d, J=6.1 Hz). 3-[4-(4-isopropoxythiophen-3-yl)-1H-1,2,3-triazol-1-yl]piperidine-2,6-dione $^1$H-NMR (DMSO-d$_6$) δ 11.23 (1H, s), 8.24 (1H, s), 7.86 (1H, d, J=3.3 Hz), 6.74 (1H, d, J=3.3 Hz), 5.87 (1H, dd, J=4.9, 12.2 Hz), 4.56 (1H, sep, J=6.0 Hz), 2.65-2.93 (3H, m), 2.28-2.36 (1H, m), 1.36 (6H, d, J=6.0 Hz).

Example 27 (Compound 27)

3-{4-[4-(cyclopentyloxy)thiophen-3-yl]-1H-1,2,3-triazol-1-yl}piperidine-2,6-dione (27-1) To a solution of methyl 4-bromo-3-hydroxythiophene-2-carboxylate (1.00 g, 4.22 mmol) in N,N-dimethylformamide (14 mL) were added cyclopentyl bromide (1.13 mL, 10.54 mmol) and cesium carbonate (3.44 g, 10.56 mmol) and the mixture was stirred under an argon atmosphere at 100-110° C. for 48 hr. To the reaction mixture was added water and the mixture was extracted with diethyl ether. The organic layer was washed with saturated brine, dried over anhydrous magnesium sulfate and concentrated. The concentrated residue was purified by column chromatography (hexane/ethyl acetate) to give methyl 4-bromo-3-(cyclopentyloxy)thiophene-2-carboxylate (1.20 g, 93%) as a colorless oil.

$^1$H-NMR (CDCl$_3$) δ 7.38 (1H, s), 5.10-5.17 (1H, m), 3.87 (3H, s), 1.85-2.04 (4H, m), 1.69-1.82 (2H, m), 1.55-1.69 (2H, m).

(27-2) To a solution of methyl 4-bromo-3-(cyclopentyloxy)thiophene-2-carboxylate (1.20 g, 3.93 mmol) in methanol (6.7 mL) were added water (2.8 mL) and potassium hydroxide (85%) (0.31 g, 4.70 mmol), and the mixture was refluxed for 3 hr. The reaction mixture was concentrated, water was added to the concentrated residue and the mixture was washed with diethyl ether. To the aqueous layer was added 2.0 M hydrochloric acid (2.5 mL) and the mixture was extracted with diethyl ether. The organic layer was washed with saturated brine, dried over anhydrous magnesium sulfate and concentrated to give 4-bromo-3-(cyclopentyloxy)thiophene-2-carboxylic acid (1.05 g, 92%) as a white solid. The obtained 4-bromo-3-(cyclopentyloxy)thiophene-2-carboxylic acid was used for the next reaction without purification.

$^1$H-NMR (CDCl$_3$) δ 7.51 (1H, s), 5.30-5.36 (1H, m), 1.78-2.05 (6H, m), 1.63-1.73 (2H, m).

(27-3) To a solution of 4-bromo-3-(cyclopentyloxy)thiophene-2-carboxylic acid (1.05 g, 3.61 mmol) in quinoline (15 mL) was added copper powder (0.26 g, 4.09 mmol) and the mixture was stirred under an argon atmosphere at 150° C. for 15 min. To the reaction mixture was added 2.0 M hydrochloric acid (65 mL), and the mixture was filtered through celite, and the filtrate was extracted with diethyl ether. The organic layer was washed with saturated brine, dried over anhydrous magnesium sulfate and concentrated. The concentrated residue was purified by column chromatography (hexane/ethyl acetate) to give 3-bromo-4-(cyclopentyloxy)thiophene (0.81 g, 91%) as a colorless oil.

$^1$H-NMR (CDCl$_3$) δ 7.16 (1H, d, J=3.5 Hz), 6.18 (1H, d, J=3.5 Hz), 4.64-4.70 (1H, m), 1.76-1.98 (6H, m), 1.56-1.68 (2H, m).

(27-4) By a method similar to that in Example 11, 3-{4-[4-(cyclopentyloxy)thiophen-3-yl]-1H-1,2,3-triazol-1-yl}piperidine-2,6-dione was obtained as a pale-blue solid (8% yield) from 3-bromo-4-(cyclopentyloxy)thiophene.

{[4-(cyclopentyloxy)thiophen-3-yl]ethynyl}trimethylsilane $^1$H-NMR (CDCl$_3$) δ 7.33 (1H, d, J=3.3 Hz), 6.14 (1H, d, J=3.3 Hz), 4.67 (1H, sep, J=2.7 Hz), 1.76-2.06 (6H, m), 1.56-1.70 (2H, m), 0.24 (9H, s).

3-(cyclopentyloxy)-4-ethynylthiophene $^1$H-NMR (CDCl$_3$) δ 7.38 (1H, d, J=3.3 Hz), 6.14 (1H, d, J=3.4 Hz), 4.63-4.70 (1H, m), 3.12 (1H, s), 1.75-1.98 (6H, m), 1.54-1.69 (2H, m).

3-{4-[4-(cyclopentyloxy)thiophen-3-yl]-1H-1,2,3-triazol-1-yl}piperidine-2,6-dione $^1$H-NMR (DMSO-d$_6$) δ 11.22 (1H, s), 8.17 (1H, s), 7.87 (1H, d, J=3.3 Hz), 6.68 (1H, d, J=3.3 Hz), 5.88 (1H, dd, J=5.2, 12.5 Hz), 4.76-4.84 (1H, m), 2.65-2.92 (3H, m), 2.27-2.37 (1H, m), 1.91-2.02 (2H, m), 1.80-1.91 (2H, m), 1.67-1.80 (2H, m), 1.53-1.67 (2H, m).

Example 28 (Compound 28)

3-{4-[4-(cyclopropylmethoxy)thiophen-3-yl]-1H-1,2,3-triazol-1-yl}piperidine-2,6-dione By a method similar to that in Example 27, 3-{4-[4-(cyclopropylmethoxy)thiophen-3-yl]-1H-1,2,3-triazol-1-yl}piperidine-2,6-dione was obtained as a gray solid (14% yield) from methyl 4-bromo-3-hydroxythiophene-2-carboxylate and (bromomethyl)cyclopropane.

methyl 4-bromo-3-(cyclopropylmethoxy)thiophene-2-carboxylate $^1$H-NMR (CDCl$_3$) δ 7.38 (1H, s), 4.02 (2H, d, J=7.2 Hz), 3.87 (3H, s), 1.29-1.41 (1H, m), 0.58-0.65 (2H, m), 0.31-0.38 (2H, m).

4-bromo-3-(cyclopropylmethoxy)thiophene-2-carboxylic acid $^1$H-NMR (CDCl$_3$) δ 7.51 (1H, s), 4.16 (2H, d, J=7.4 Hz), 1.27-1.39 (1H, m), 0.64-0.71 (2H, m), 0.33-0.40 (2H, m).

3-bromo-4-(cyclopropylmethoxy)thiophene $^1$H-NMR (CDCl$_3$) δ 7.18 (1H, d, J=3.5 Hz), 6.21 (1H, d, J=3.5 Hz), 3.83 (2H, d, J=6.8 Hz), 1.25-1.38 (1H, m), 0.61-0.69 (2H, m), 0.34-0.41 (2H, m).

{[4-(cyclopropylmethoxy)thiophen-3-yl]ethynyl}trimethylsilane $^1$H-NMR (CDCl$_3$) δ 7.35 (1H, d, J=3.3 Hz), 6.15 (1H, d, J=3.4 Hz), 3.84 (2H, d, J=6.7 Hz), 1.23-1.37 (1H, m), 0.56-0.73 (2H, m), 0.35-0.42 (2H, m), 0.25 (9H, s).

3-(cyclopropylmethoxy)-4-ethynylthiophene $^1$H-NMR (CDCl$_3$) δ 7.41 (1H, d, J=3.4 Hz), 6.17 (1H, d, J=3.4 Hz), 3.83 (2H, d, J=6.9 Hz), 3.18 (1H, s), 1.20-1.47 (1H, m), 0.56-0.74 (2H, m), 0.34-0.41 (2H, m).

3-{4-[4-(cyclopropylmethoxy)thiophen-3-yl]-1H-1,2,3-triazol-1-yl}piperidine-2,6-dione $^1$H-NMR (DMSO-d$_6$) δ 11.23 (1H, s), 8.24 (1H, s), 7.87 (1H, d, J=3.3 Hz), 6.72 (1H, d, J=3.4 Hz), 5.89 (1H, dd, J=5.3, 12.6 Hz), 3.87-3.97 (2H, m), 2.65-2.94 (3H, m), 2.30-2.40 (1H, m), 1.28-1.40 (1H, m), 0.59 (2H, ddd, J=4.2, 6.0, 8.0 Hz), 0.34-0.41 (2H, m).

Example 29 (Compound 29)

3-{4-[4-(cyclopentylmethoxy)thiophen-3-yl]-1H-1,2,3-triazol-1-yl}piperidine-2,6-dione By a method similar to that in Example 27, 3-{4-[4-(cyclopentylmethoxy)thiophen-3-yl]-1H-1,2,3-triazol-1-yl}piperidine-2,6-dione was obtained as a white solid (17% yield) from methyl 4-bromo-3-hydroxythiophene-2-carboxylate and (iodomethyl)cyclopentane.

methyl 4-bromo-3-(cyclopentylmethoxy)thiophene-2-carboxylate $^1$H-NMR (CDCl$_3$) δ 7.38 (1H, s), 4.05 (2H, d, J=6.9 Hz), 3.87 (3H, s), 2.43 (1H, sep, J=7.4 Hz), 1.80-1.91 (2H, m), 1.53-1.71 (4H, m), 1.41-1.51 (2H, m).

4-bromo-3-(cyclopentylmethoxy)thiophene-2-carboxylic acid $^1$H-NMR (CDCl$_3$) δ 7.49 (1H, s), 4.14 (2H, d, J=7.0 Hz), 2.44 (1H, sep, J=7.5 Hz), 1.79-1.94 (2H, m), 1.53-1.73 (4H, m), 1.36-1.51 (2H, m).

3-bromo-4-(cyclopentylmethoxy)thiophene $^1$H-NMR (CDCl$_3$) δ 7.17 (1H, d, J=3.5 Hz), 6.20 (1H, d, J=3.5 Hz), 3.86 (2H, d, J=6.8 Hz), 2.41 (1H, sep, J=7.5 Hz), 1.78-1.90 (2H, m), 1.53-1.72 (4H, m), 1.33-1.44 (2H, m).

{[4-(cyclopentylmethoxy)thiophen-3-yl]ethynyl}trimethylsilane $^1$H-NMR (CDCl$_3$) δ 7.34 (1H, d, J=3.3 Hz), 6.14 (1H, d, J=3.3 Hz), 3.85 (2H, d, J=6.6 Hz), 2.40 (1H, sep, J=7.3 Hz), 1.77-1.88 (2H, m), 1.52-1.73 (4H, m), 1.37-1.48 (2H, m), 0.24 (9H, s).

3-(cyclopentylmethoxy)-4-ethynylthiophene $^1$H-NMR (CDCl$_3$) δ 7.39 (1H, d, J=3.4 Hz), 6.17 (1H, d, J=3.4 Hz), 3.85 (2H, d, J=6.9 Hz), 3.14 (1H, s), 2.42 (1H, sep, J=7.4 Hz), 1.79-1.89 (2H, m), 1.52-1.71 (4H, m), 1.32-1.43 (2H, m).

3-{4-[4-(cyclopentylmethoxy)thiophen-3-yl]-1H-1,2,3-triazol-1-yl}piperidine-2,6-dione $^1$H-NMR (DMSO-d$_6$) δ 11.23 (1H, s), 8.16 (1H, s), 7.88 (1H, J=3.4 Hz), 6.73 (1H, d, J=3.4 Hz), 5.89 (1H, dd, J=5.2, 12.6 Hz), 3.89-3.99 (2H, m), 2.65-2.93 (3H, m), 2.29-2.48 (2H, m), 1.78-1.90 (2H, m), 1.49-1.69 (4H, m), 1.27-1.40 (2H, m).

Example 30 (Compound 30)

3-{4-[4-(cyclohexylmethoxy)thiophen-3-yl]-1H-1,2,3-triazol-1-yl}piperidine-2,6-dione By a method similar to that in Example 27, 3-{4-[4-(cyclohexylmethoxy)thiophen-3-yl]-1H-1,2,3-triazol-1-yl}piperidine-2,6-dione was obtained as a red-brown solid (15% yield) from methyl 4-bromo-3-hydroxythiophene-2-carboxylate and (bromomethyl)cyclohexane.

methyl 4-bromo-3-(cyclohexylmethoxy)thiophene-2-carboxylate $^1$H-NMR (CDCl$_3$) δ 7.37 (1H, s), 3.96 (2H, d, J=6.2 Hz), 3.87 (3H, s), 1.65-1.98 (6H, m), 1.06-1.38 (5H, m).

4-bromo-3-(cyclohexylmethoxy)thiophene-2-carboxylic acid

¹H-NMR (CDCl₃) δ 7.49 (1H, s), 4.05 (2H, d, J=6.0 Hz), 1.66-1.97 (6H, m), 1.06-1.39 (5H, m).

3-bromo-4-(cyclohexylmethoxy)thiophene

¹H-NMR (CDCl₃) δ 7.17 (1H, d, J=3.5 Hz), 6.19 (1H, d, J=3.4 Hz), 3.77 (2H, d, J=6.1 Hz), 1.65-1.93 (6H, m), 1.14-1.38 (3H, m), 0.99-1.14 (2H, m).

{[4-(cyclohexylmethoxy)thiophen-3-yl]ethynyl}trimethylsilane

¹H-NMR (CDCl₃) δ 7.33 (1H, d, J=3.3 Hz), 6.13 (1H, d, J=3.3 Hz), 3.76 (2H, d, J=6.0 Hz), 1.65-1.92 (6H, m), 1.03-1.37 (5H, m), 0.24 (9H, s).

3-(cyclohexylmethoxy)-4-ethynylthiophene

¹H-NMR (CDCl₃) δ 7.39 (1H, d, J=3.4 Hz), 6.15 (1H, d, J=3.3 Hz), 3.77 (2H, d, J=6.1 Hz), 3.14 (1H, s), 1.80-1.93 (3H, m), 1.65-1.80 (3H, m), 1.13-1.36 (3H, m), 0.99-1.13 (2H, m).

3-{4-[4-(cyclohexylmethoxy)thiophen-3-yl]-1H-1,2,3-triazol-1-yl}piperidine-2,6-dione ¹H-NMR (DMSO-d₆) δ 11.23 (1H, s), 8.17 (1H, s), 7.87 (1H, d, J=3.4 Hz), 6.72 (1H, d, J=3.4 Hz), 5.88 (1H, dd, J=5.1, 12.4 Hz), 3.83-3.93 (2H, m), 2.65-2.93 (3H, m), 2.31-2.40 (1H, m), 1.61-1.92 (6H, m), 1.01-1.35 (5H, m).

Example 31 (Compound 31)

3-{4-[4-(4-methoxybenzyloxy)thiophen-3-yl]-1H-1,2,3-triazol-1-yl}piperidine-2,6-dione By a method similar to that in Example 27, 3-{4-[4-(4-methoxybenzyloxy)thiophen-3-yl]-1H-1,2,3-triazol-1-yl}piperidine-2,6-dione was obtained as a white solid (4% yield) from methyl 4-bromo-3-hydroxythiophene-2-carboxylate and 4-methoxybenzyl chloride.

methyl 4-bromo-3-(4-methoxybenzyloxy)thiophene-2-carboxylate

¹H-NMR (CDCl₃) δ 7.42-7.50 (2H, m), 7.39 (1H, s), 6.87-6.94 (2H, m), 5.14 (2H, s), 3.88 (3H, s), 3.82 (3H, s).

4-bromo-3-(4-methoxybenzyloxy)thiophene-2-carboxylic acid

¹H-NMR (DMSO-d₆) δ 13.10-13.64 (1H, br), 7.97 (1H, s), 7.36-7.43 (2H, m), 6.91-6.98 (2H, m), 5.10 (2H, s), 3.76 (3H, s).

3-bromo-4-(4-methoxybenzyloxy)thiophene

¹H-NMR (CDCl₃) δ 7.32-7.42 (2H, m), 7.18 (1H, d, J=3.5 Hz), 6.88-6.97 (2H, m), 6.28 (1H, d, J=3.5 Hz), 5.02 (2H, s), 3.82 (3H, s).

{[4-(4-methoxybenzyloxy)thiophen-3-yl]ethynyl}trimethylsilane

¹H-NMR (CDCl₃) δ 7.35-7.41 (3H, m), 6.87-6.95 (2H, m), 6.22 (1H, d, J=3.3 Hz), 5.02 (2H, s), 3.82 (3H, s), 0.24 (9H, s).

3-ethynyl-4-(4-methoxybenzyloxy)thiophene

¹H-NMR (CDCl₃) δ 7.41 (1H, d, J=3.4 Hz), 7.34-7.40 (2H, m), 6.88-6.94 (2H, m), 6.22 (1H, d, J=3.3 Hz), 5.03 (2H, s), 3.81 (3H, s), 3.16 (1H, s).

3-{4-[4-(4-methoxybenzyloxy)thiophen-3-yl]-1H-1,2,3-triazol-1-yl}piperidine-2,6-dione ¹H-NMR (DMSO-d₆) δ 11.22 (1H, s), 8.21 (1H, s), 7.87 (1H, d, J=3.4 Hz), 7.40-7.47 (2H, m), 6.92-6.99 (2H, m), 6.82 (1H, d, J=3.4 Hz), 5.84 (1H, dd, J=5.0, 12.4 Hz), 5.12 (2H, s), 3.75 (3H, s), 2.63-2.92 (3H, m), 2.28-2.38 (1H, m).

Example 32 (Compound 32)

3-{4-[4-(benzyloxy)thiophen-3-yl]-1H-1,2,3-triazol-1-yl}piperidine-2,6-dione

By a method similar to that in Example 27 (27-3, 27-4), 3-{4-[4-(benzyloxy)thiophen-3-yl]-1H-1,2,3-triazol-1-yl}piperidine-2,6-dione was obtained as a gray solid (29% yield) from 3-(benzyloxy)-4-bromothiophene-2-carboxylic acid.

3-(benzyloxy)-4-bromothiophene

¹H-NMR (CDCl₃) δ 7.42-7.48 (2H, m), 7.36-7.42 (2H, m), 7.30-7.36 (1H, m), 7.19 (1H, d, J=3.5 Hz), 6.27 (1H, d, J=3.5 Hz), 5.09 (2H, s).

{[4-(benzyloxy)thiophen-3-yl]ethynyl}trimethylsilane

¹H-NMR (CDCl₃) δ 7.28-7.49 (6H, m), 6.22 (1H, d, J=3.3 Hz), 5.09 (2H, s), 0.25 (9H, s).

3-(benzyloxy)-4-ethynylthiophene

¹H-NMR (CDCl₃) δ 7.29-7.47 (6H, m), 6.22 (1H, d, J=3.3 Hz), 5.11 (2H, s), 3.18 (1H, s).

3-{4-[4-(benzyloxy)thiophen-3-yl]-1H-1,2,3-triazol-1-yl}piperidine-2,6-dione

¹H-NMR (DMSO-d₆) δ 11.23 (1H, s), 8.28 (1H, s), 7.89 (1H, d, J=3.4 Hz), 7.47-7.53 (2H, m), 7.37-7.44 (2H, m), 7.30-7.37 (1H, m), 6.82 (1H, d, J=3.4 Hz), 5.86 (1H, dd, J=5.1, 12.4 Hz), 5.22 (2H, s), 2.64-2.93 (3H, m), 2.29-2.39 (1H, m).

Example 33 (Compound 33)

3-{4-[4-(pyridin-4-ylmethoxy)thiophen-3-yl]-1H-1,2,3-triazol-1-yl}piperidine-2,6-dione (33-1) To a solution of methyl 4-bromo-3-hydroxythiophene-2-carboxylate (0.75 g, 3.16 mmol) in N,N-dimethylformamide (11 mL) were added 4-(bromomethyl)pyridine hydrobromide (2.00 g, 7.91 mmol), triethylamine (1.10 mL, 7.89 mmol) and cesium carbonate (2.58 g, 7.92 mmol) and the mixture was stirred under an argon atmosphere at 50° C. for 20 hr. The reaction mixture was filtered, water was added to the filtrate, and the mixture was extracted with ethyl acetate. The organic layer was washed with water and saturated brine, dried over anhydrous magnesium sulfate and concentrated. The concentrated residue was purified by column chromatography (dichloromethane/methanol) to give methyl 4-bromo-3-(pyridin-4-ylmethoxy)thiophene-2-carboxylate (0.27 g, 26%) as a brown solid.

$^1$H-NMR (CDCl$_3$) δ 8.55-8.75 (2H, m), 7.46-7.50 (2H, m), 7.44 (1H, s), 5.24 (2H, s), 3.87 (3H, s).

(33-2) To a solution of methyl 4-bromo-3-(pyridin-4-ylmethoxy)thiophene-2-carboxylate (0.95 g, 2.89 mmol) in methanol (4.9 mL) were added potassium hydroxide (85%) (0.23 g, 3.48 mmol) and water (2.0 mL), and the mixture was refluxed for 15 hr. The reaction mixture was concentrated, water (6 mL) and 1.0 M hydrochloric acid (3.52 mL) were added to the concentrated residue and the mixture was stirred at room temperature for 10 min. The precipitate was collected by filtration and washed with water to give 4-bromo-3-(pyridin-4-ylmethoxy)thiophene-2-carboxylic acid (0.89 g, 98%) as a pale-brown solid. The obtained 4-bromo-3-(pyridin-4-ylmethoxy)thiophene-2-carboxylic acid was used for the next reaction without purification.

$^1$H-NMR (DMSO-d$_6$) δ 12.75-14.10 (1H, br), 8.52-8.69 (2H, br), 8.03 (1H, s), 7.51 (2H, d, J=5.1 Hz), 5.24 (2H, s).

(33-3) To a solution of 4-bromo-3-(pyridin-4-ylmethoxy)thiophene-2-carboxylic acid (0.89 g, 2.83 mmol) in quinoline (11 mL) was added copper powder (0.21 g, 3.30 mmol), and the mixture was stirred under an argon atmosphere at 150° C. for 15 min. The reaction mixture was filtered through celite, and the filtrate was concentrated. The concentrated residue was purified by column chromatography (hexane/ethyl acetate) to give 4-[(4-bromothiophen-3-yloxy)methyl]pyridine (0.69 g, 90%) as a brown solid.

$^1$H-NMR (CDCl$_3$) δ 8.50-8.75 (2H, br), 7.39 (2H, brd, J=5.0 Hz), 7.24 (1H, d, J=3.4 Hz), 6.27 (1H, d, J=3.5 Hz), 5.11 (2H, s).

(33-4) By a method similar to that in Example 11, 3-{4-[4-(pyridin-4-ylmethoxy)thiophen-3-yl]-1H-1,2,3-triazol-1-yl}piperidine-2,6-dione was obtained as a gray solid (10% yield) from 4-[(4-bromothiophen-3-yloxy)methyl]pyridine.

4-({4-[(trimethylsilyl)ethynyl]thiophen-3-yloxy}methyl)pyridine $^1$H-NMR (CDCl$_3$) δ 8.50-8.75 (2H, br), 7.37-7.43 (2H, br), 7.40 (1H, d, J=3.3 Hz), 6.22 (1H, d, J=3.3 Hz), 5.10 (2H, s), 0.27 (9H, s).

4-[(4-ethynylthiophen-3-yloxy)methyl]pyridine $^1$H-NMR (CDCl$_3$) δ 8.58-8.68 (2H, m), 7.45 (1H, d, J=3.4 Hz), 7.35-7.40 (2H, m), 6.21 (1H, d, J=3.3 Hz), 5.12 (2H, s), 3.21 (1H, s).

3-{4-[4-(pyridin-4-ylmethoxy)thiophen-3-yl]-1H-1,2,3-triazol-1-yl}piperidine-2,6-dione $^1$H-NMR (DMSO-d$_6$) δ 11.24 (1H, s), 8.20-9.55 (2H, br), 8.36 (1H, s), 7.90 (1H, d, J=3.4 Hz), 7.23-7.86 (2H, br), 6.81 (1H, d, J=3.4 Hz), 5.88 (1H, dd, J=5.3, 12.6 Hz), 5.25 (2H, brs), 2.65-2.94 (3H, m), 2.29-2.40 (1H, m).

Example 34 (Compound 34)

3-{4-[4-(pyridin-2-ylmethoxy)thiophen-3-yl]-1H-1,2,3-triazol-1-yl}piperidine-2,6-dione By a method similar to that in Example 33, 3-{4-[4-(pyridin-2-ylmethoxy)thiophen-3-yl]-1H-1,2,3-triazol-1-yl}piperidine-2,6-dione was obtained as a gray solid (23% yield) from methyl 4-bromo-3-hydroxythiophene-2-carboxylate and 2-(bromomethyl)pyridine hydrobromide.

methyl 4-bromo-3-(pyridin-2-ylmethoxy)thiophene-2-carboxylate $^1$H-NMR (CDCl$_3$) δ 8.55-8.63 (1H, m), 7.74-7.87 (2H, m), 7.43 (1H, s), 7.22-7.28 (1H, m), 5.33 (2H, s), 3.85 (3H, s).

4-bromo-3-(pyridin-2-ylmethoxy)thiophene-2-carboxylic acid $^1$H-NMR (DMSO-d$_6$) δ 12.96-13.89 (1H, br), 8.51-8.57 (1H, m), 8.01 (1H, s), 7.88 (1H, dt, J=1.8, 7.7 Hz), 7.69-7.74 (1H, m), 7.34-7.40 (1H, m), 5.27 (2H, s).

2-[(4-bromothiophen-3-yloxy)methyl]pyridine $^1$H-NMR (CDCl$_3$) δ 8.55-8.62 (1H, m), 7.75 (1H, dt, J=1.7, 7.7 Hz), 7.58-7.64 (1H, m), 7.20-7.27 (2H, m), 6.32 (1H, d, J=3.5 Hz), 5.23 (2H, s).

2-({4-[(trimethylsilyl)ethynyl]thiophen-3-yloxy}methyl)pyridine $^1$H-NMR (CDCl$_3$) δ 8.54-8.62 (1H, m), 7.73 (1H, dt, J=1.7, 7.7 Hz), 7.63-7.68 (1H, m), 7.39 (1H, d, J=3.3 Hz), 7.20-7.25 (1H, m), 6.26 (1H, d, J=3.3 Hz), 5.21 (2H, s), 0.27 (9H, s).

2-[(4-ethynylthiophen-3-yloxy)methyl]pyridine $^1$H-NMR (CDCl$_3$) δ 8.54-8.64 (1H, m), 7.73 (1H, dt, J=1.7, 7.7 Hz), 7.56-7.64 (1H, m), 7.43 (1H, d, J=3.4 Hz), 7.20-7.25 (1H, m), 6.26 (1H, d, J=3.4 Hz), 5.24 (2H, s), 3.22 (1H, s).

3-{4-[4-(pyridin-2-ylmethoxy)thiophen-3-yl]-1H-1,2,3-triazol-1-yl}piperidine-2,6-dione $^1$H-NMR (DMSO-d$_6$) δ 11.24 (1H, brs), 8.60 (1H, d, J=4.4 Hz), 8.41 (1H, s), 7.90 (1H, d, J=3.4 Hz), 7.84 (1H, dt, J=1.7, 7.7 Hz), 7.54 (1H, d, J=7.8 Hz), 7.36 (1H, dd, J=5.0, 6.8 Hz), 6.82 (1H, d, J=3.4 Hz), 5.88 (1H, dd, J=5.2, 12.5 Hz), 5.29 (2H, s), 2.81-2.94 (1H, m), 2.64-2.81 (2H, m), 2.30-2.40 (1H, m).

Example 35 (Compound 35)

3-{4-[4-(pyridin-3-ylmethoxy)thiophen-3-yl]-1H-1,2,3-triazol-1-yl}piperidine-2,6-dione By a method similar to that in Example 33, 3-{4-[4-(pyridin-3-ylmethoxy)thiophen-3-yl]-1H-1,2,3-triazol-1-yl}piperidine-2,6-dione was obtained as a gray solid (5% yield) from methyl 4-bromo-3-hydroxythiophene-2-carboxylate and 3-(bromomethyl)pyridine hydrobromide.

methyl 4-bromo-3-(pyridin-3-ylmethoxy)thiophene-2-carboxylate $^1$H-NMR (CDCl$_3$) δ 8.70-8.78 (1H, br), 8.57-8.64 (1H, m), 7.91-7.97 (1H, m), 7.42 (1H, s), 7.31-7.38 (1H, m), 5.24 (2H, s), 3.89 (3H, s).

4-bromo-3-(pyridin-3-ylmethoxy)thiophene-2-carboxylic acid $^1$H-NMR (DMSO-d$_6$) δ 13.15-13.76 (1H, br), 8.67 (1H, brs), 8.53-8.61 (1H, m), 8.00 (1H, s), 7.87-7.93 (1H, m), 7.44 (1H, ddd, J=0.4, 4.8, 7.8 Hz), 5.23 (2H, s).

3-[(4-bromothiophen-3-yloxy)methyl]pyridine $^1$H-NMR (CDCl$_3$) δ 8.66-8.75 (1H, m), 8.56-8.64 (1H, m), 7.79-7.87 (1H, m), 7.35 (1H, ddd, J=0.4, 4.9, 7.8 Hz), 7.22 (1H, d, J=3.4 Hz), 6.33 (1H, d, J=3.5 Hz), 5.11 (2H, s).

3-({4-[(trimethylsilyl)ethynyl]thiophen-3-yloxy}methyl)pyridine $^1$H-NMR (CDCl$_3$) δ 8.66-8.74 (1H, br), 8.54-8.63 (1H, m), 7.80-7.87 (1H, m), 7.39 (1H, d, J=3.3 Hz), 7.33 (1H, dd, J=4.9, 7.7 Hz), 6.28 (1H, d, J=3.3 Hz), 5.11 (2H, s), 0.24 (9H, s).

3-[(4-ethynylthiophen-3-yloxy)methyl]pyridine $^1$H-NMR (CDCl$_3$) δ 8.67-8.73 (1H, m), 8.59 (1H, dd, J=1.6, 4.8 Hz), 7.78-7.83 (1H, m), 7.44 (1H, d, J=3.3 Hz), 7.33 (1H, ddd, J=0.6, 4.8, 7.8 Hz), 6.28 (1H, d, J=3.3 Hz), 5.12 (2H, s), 3.17 (1H, s).

3-{4-[4-(pyridin-3-ylmethoxy)thiophen-3-yl]-1H-1,2,3-triazol-1-yl}piperidine-2,6-dione $^1$H-NMR (DMSO-d$_6$) δ 11.23 (1H, s,), 8.73 (1H, d, J=1.7 Hz), 8.55 (1H, dd, J=1.6, 4.8 Hz), 8.27 (1H, s), 7.90-7.94 (1H, m), 7.89 (1H, d, J=3.4 Hz), 7.43 (1H, ddd, J=0.7, 4.8, 7.8 Hz), 6.89 (1H, d, J=3.4 Hz), 5.85 (1H, dd, J=5.2, 12.5 Hz), 5.26 (2H, s), 2.79-2.92 (1H, m), 2.63-2.79 (2H, m), 2.26-2.39 (1H, m).

Example 36 (Compound 36)

3-(4-{4-[4-(morpholinomethyl)benzyloxy]thiophen-3-yl}-1H-1,2,3-triazol-1-yl)piperidine-2,6-dione (36-1) To a solution of methyl 4-bromo-3-hydroxythiophene-2-carboxylate (1.00 g, 4.22 mmol) in acetonitrile (50 mL) were added α,α'-dibromo-p-xylene (3.34 g, 12.65 mmol) and potassium carbonate (0.58 g, 4.20 mmol), and the mixture was stirred under an argon atmosphere at 50° C. for 15 hr. The reaction mixture was concentrated, saturated brine was added to the concentrated residue, and the mixture was extracted with diethyl ether. The organic layer was washed with saturated brine, dried over anhydrous magnesium sulfate and concentrated. The concentrated residue was purified by column chromatography (hexane/ethyl acetate) to give methyl 4-bromo-3-[4-(bromomethyl)benzyloxy]thiophene-2-carboxylate (1.30 g, 73%) as a pale-brown solid.

$^1$H-NMR (CDCl$_3$) δ 7.50-7.56 (2H, m), 7.39-7.45 (3H, m), 5.20 (2H, s), 4.51 (2H, s), 3.87 (3H, s).

(36-2) To a solution of methyl 4-bromo-3-[4-(bromomethyl)benzyloxy]thiophene-2-carboxylate (1.95 g, 4.64 mmol) in dichloromethane (46 mL) was added morpholine (0.89 mL, 10.17 mmol), and the mixture was stirred under an argon atmosphere at room temperature for 20 hr. The reaction mixture was filtered, and the filtrate was concentrated. The concentrated residue was dissolved in ethyl acetate, washed with water, dried over anhydrous magnesium sulfate and concentrated. The concentrated residue was purified by column chromatography (hexane/ethyl acetate) to give methyl 4-bromo-3-[4-(morpholinomethyl)benzyloxy]thiophene-2-carboxylate mixture (2.15 g) as a pale-yellow oil. The obtained methyl 4-bromo-3-[4-(morpholinomethyl)benzyloxy]thiophene-2-carboxylate mixture was used for the next reaction without further purification.

$^1$H-NMR (CDCl$_3$) δ 7.50 (2H, d, J=8.0 Hz), 7.40 (1H, s), 7.35 (2H, d, J=8.0 Hz), 5.18 (2H, s), 3.88 (3H, s), 3.66-3.78 (4H, m), 3.51 (2H, s), 2.41-2.48 (4H, m).

(36-3) By a method similar to that in Example 33 (33-2, 33-3), 4-{4-[(4-bromothiophen-3-yloxy)methyl]benzyl}morpholine was obtained as a red-brown oil (89% yield) from methyl 4-bromo-3-[4-(morpholinomethyl)benzyloxy]thiophene-2-carboxylate mixture.

4-bromo-3-[4-(morpholinomethyl)benzyloxy]thiophene-2-carboxylic acid $^1$H-NMR (DMSO-d$_6$) δ 7.97 (1H, s), 7.44 (2H, d, J=8.0 Hz), 7.33 (2H, d, J=8.0 Hz), 5.15 (2H, s), 3.54-3.62 (4H, m), 3.50 (2H, s), 2.34-2.42 (4H, m).

4-{4-[(4-bromothiophen-3-yloxy)methyl]benzyl}morpholine $^1$H-NMR (CDCl$_3$) δ 7.40 (2H, d, J=8.2 Hz), 7.35 (2H, d, J=8.2 Hz), 7.20 (1H, d, J=3.5 Hz), 6.28 (1H, d, J=3.5 Hz), 5.07 (2H, s), 3.68-3.73 (4H, m), 3.50 (2H, s), 2.42-2.48 (4H, m).

(36-4) To a solution of 4-{4-[(4-bromothiophen-3-yloxy)methyl]benzyl}morpholine (1.56 g, 4.24 mmol) in acetonitrile (8.5 mL) were added triethylamine (0.89 mL, 6.39 mmol), tetrakis(triphenylphosphine)palladium (0) (0.24 g, 0.21 mmol), copper(I) iodide (0.12 g, 0.63 mmol) and trimethylsilylacetylene (0.64 mL, 4.63 mmol), and the mixture was sealed in a tube under an argon atmosphere and stirred at 60° C. for 4 days. To the reaction mixture was added water and the mixture was extracted with dichloromethane. The organic layer was washed with saturated brine, dried over anhydrous magnesium sulfate and concentrated. The concentrated residue was purified by column chromatography (hexane/ethyl acetate) to give 4-{4-([4-[(trimethylsilyl)ethynyl]thiophen-3-yloxy}methyl)benzyl]morpholine (0.63 g, 38%) as a brown oil.

$^1$H-NMR (CDCl$_3$) δ 7.41 (2H, d, J=8.1 Hz), 7.37 (1H, d, J=3.3 Hz), 7.33 (2H, d, J=8.1 Hz), 6.23 (1H, d, J=3.3 Hz), 5.07 (2H, s), 3.68-3.74 (4H, m), 3.51 (2H, s), 2.41-2.48 (4H, m), 0.24 (9H, s).

(36-5) By a method similar to that in Example 8 (8-2, 8-3), 3-(4-{4-[4-(morpholinomethyl)benzyloxy]thiophen-3-yl}-1H-1,2,3-triazol-1-yl)piperidine-2,6-dione was obtained as a brown solid (50% yield) from 4-{4-([4-[(trimethylsilyl)ethynyl]thiophen-3-yloxy}methyl)benzyl]morpholine.

4-{4-[(4-ethynylthiophen-3-yloxy)methyl]benzyl}morpholine $^1$H-NMR (CDCl$_3$) δ 7.42 (1H, d, J=3.4 Hz), 7.40 (2H, d, J=8.3 Hz), 7.34 (2H, d, J=8.2 Hz), 6.22 (1H, d, J=3.3 Hz), 5.09 (2H, s), 3.71 (4H, brt, J=4.7 Hz), 3.50 (2H, s), 3.17 (1H, s), 2.45 (4H, brt, J=4.5 Hz).

3-(4-{4-[4-(morpholinomethyl)benzyloxy]thiophen-3-yl}-1H-1,2,3-triazol-1-yl)piperidine-2,6-dione $^1$H-NMR (DMSO-d$_6$) δ 11.23 (1H, s), 8.27 (1H, s), 7.88 (1H, d, J=3.4 Hz), 7.45 (2H, d, J=8.0 Hz), 7.33 (2H, d, J=8.1 Hz), 6.82 (1H, d, J=3.4 Hz), 5.86 (1H, dd, J=5.0, 12.3 Hz), 5.20 (2H, s), 3.56 (4H, brt, J=4.6 Hz), 3.45 (2H, s), 2.65-2.92 (3H, m), 2.29-2.39 (5H, m).

(36-6) To a suspension of 3-(4-{4-[4-(morpholinomethyl)benzyloxy]thiophen-3-yl}-1H-1,2,3-triazol-1-yl)piperidine-2,6-dione (0.10 g, 0.21 mmol) in acetone (5 ml) was added methanesulfonic acid (13.9 µl, 0.21 mmol), and the mixture was stirred at room temperature for 15.5 hr. The precipitate was collected by filtration, and washed with acetone to give 3-(4-{4-[4-(morpholinomethyl)benzyloxy]thiophen-3-yl}-1H-1,2,3-triazol-1-yl)piperidine-2,6-dione methanesulfonate (0.10 g, 86%) as a pale-brown solid.

$^1$H-NMR (DMSO-d$_6$) δ 11.25 (1H, s), 9.70-9.86 (1H, br), 8.34 (1H, s), 7.89 (1H, d, J=3.4 Hz), 7.61 (2H, d, J=7.8 Hz), 7.52 (2H, d, J=7.8 Hz), 6.82 (1H, d, J=3.4 Hz), 5.87 (1H, dd, J=5.2, 12.6 Hz), 5.27 (2H, brs), 4.36 (2H, brd, J=4.8 Hz), 3.96 (2H, brd, J=11.9 Hz), 3.61 (2H, brt, J=12.0 Hz), 3.26 (2H, brd, J=11.6 Hz), 3.05-3.18 (2H, m), 2.81-2.94 (1H, m), 2.65-2.81 (2H, m), 2.28-2.39 (4H, m).

Example 37 (Compound 37)

3-(4-{4-[4-(methoxymethyl)benzyloxy]thiophen-3-yl}-1H-1,2,3-triazol-1-yl)piperidine-2,6-dione (37-1) To a solution of methyl 4-bromo-3-[4-(bromomethyl)benzyloxy]thiophene-2-carboxylate (synthesized by the method of Example 36 (36-1)) (2.71 g, 6.45 mmol) in methanol (11 mL) were added potassium hydroxide (85%) (0.52 g, 7.88 mmol) and water (4.5 mL), and the mixture was refluxed. After 2 hr, potassium hydroxide (85%) (0.74 g, 11.21 mmol) was added and the mixture was further refluxed for 1 hr. The reaction mixture was concentrated, water (20 mL) and 2.0 M hydrochloric acid (10.0 mL) were added to the concentrated residue, and the mixture was extracted with ethyl acetate. The organic layer was washed with saturated brine, dried over anhydrous magnesium sulfate and concentrated to give a 4-bromo-3-[4-(methoxymethyl)benzyloxy]thiophene-2-carboxylic acid mixture (2.26 g) as a yellow-brown solid. The obtained 4-bromo-3-[4-(methoxymethyl)benzyloxy]thiophene-2-carboxylic acid mixture was used for the next reaction without purification.

$^1$H-NMR (CDCl$_3$) δ 7.52 (1H, s), 7.49 (2H, d, J=7.9 Hz), 7.37 (2H, d, J=8.1 Hz), 5.27 (2H, s), 4.48 (2H, s), 3.39 (3H, s).

(37-2) To a solution of 4-bromo-3-[4-(methoxymethyl)benzyloxy]thiophene-2-carboxylic acid mixture (2.26 g) in dimethylsulfoxide (13 mL) were added silver carbonate (0.17 g, 0.62 mmol) and acetic acid (0.38 mL, 6.64 mmol), and the mixture was stirred under an argon atmosphere at 120° C. for 30 min. To the reaction mixture was added ethyl acetate and the mixture was filtered. Water was added to the filtrate and the mixture was extracted with ethyl acetate. The organic layer was washed with water and saturated brine, dried over anhydrous magnesium sulfate and concentrated. The concentrated residue was purified by column chromatography (hexane/ethyl acetate) to give 3-bromo-4-[4-(methoxymethyl)benzyloxy]thiophene (1.39 g, 2 steps 69%) as a pale-brown solid.

$^1$H-NMR (CDCl$_3$) δ 7.43 (2H, d, J=8.2 Hz), 7.36 (2H, d, J=8.2 Hz), 7.19 (1H, d, J=3.5 Hz), 6.26 (1H, d, J=3.5 Hz), 5.08 (2H, s), 4.47 (2H, s), 3.40 (3H, s).

(37-3) By a method similar to that in Example 11, 3-(4-{4-[4-(methoxymethyl)benzyloxy]thiophen-3-yl}-1H-1,2,3-triazol-1-yl)piperidine-2,6-dione was obtained as a white solid (47% yield) from 3-bromo-4-[4-(methoxymethyl)benzyloxy]thiophene.

({4-[4-(methoxymethyl)benzyloxy]thiophen-3-yl}ethynyl)trimethylsilane $^1$H-NMR (CDCl$_3$) δ 7.45 (2H, d, J=8.2 Hz), 7.37 (1H, d, J=3.3 Hz), 7.34 (2H, d, J=8.2 Hz), 6.21 (1H, d, J=3.3 Hz), 5.09 (2H, s), 4.47 (2H, s), 3.39 (3H, s), 0.25 (9H, s).

3-ethynyl-4-[4-(methoxymethyl)benzyloxy]thiophene $^1$H-NMR (CDCl$_3$) δ 7.43 (2H, d, J=8.3 Hz), 7.41 (1H, d, J=3.4 Hz), 7.35 (2H, d, J=8.2 Hz), 6.21 (1H, d, J=3.3 Hz), 5.10 (2H, s), 4.46 (2H, s), 3.39 (3H, s), 3.17 (1H, s).

3-(4-{4-[4-(methoxymethyl)benzyloxy]thiophen-3-yl}-1H-1,2,3-triazol-1-yl)piperidine-2,6-dione $^1$H-NMR (DMSO-d$_6$) δ 11.23 (1H, brs), 8.27 (1H, s), 7.88 (1H, d, J=3.4 Hz), 7.48 (2H, d, J=8.1 Hz), 7.34 (2H, d, J=8.1 Hz), 6.81 (1H, d, J=3.4 Hz), 5.86 (1H, dd, J=5.1, 12.5 Hz), 5.21 (2H, s), 4.41 (2H, s), 3.29 (3H, s), 2.63-2.93 (3H, m), 2.29-2.39 (1H, m).

Example 38 (Compound 38)

3-{4-[4-(4-{[(2S,6R)-2,6-dimethylmorpholino]methyl}benzyloxy)thiophen-3-yl]-1H-1,2,3-triazol-1-yl}piperidine-2,6-dione (38-1) By a method similar to that in Example 36 (36-1, 36-2) and Example 33 (33-2), 4-bromo-3-(4-{[(2S,6R)-2,6-dimethylmorpholino]methyl}benzyloxy)thiophene-2-carboxylic acid was obtained as a pale-yellow solid (71% yield) from methyl 4-bromo-3-hydroxythiophene-2-carboxylate, α,α'-dibromo-p-xylene and cis-2,6-dimethylmorpholine.

methyl 4-bromo-3-(4-{[(2S,6R)-2,6-dimethylmorpholino]methyl}benzyloxy)thiophene-2-carboxylate $^1$H-NMR (CDCl$_3$) δ 7.51 (2H, d, J=8.0 Hz), 7.41 (1H, s), 7.34 (2H, d, J=8.0 Hz), 5.18 (2H, s), 3.88 (3H, s), 3.64-3.73 (2H, m), 3.48 (2H, s), 2.66-2.74 (2H, m), 1.74 (2H, brt, J=10.8 Hz), 1.14 (6H, d, J=6.3 Hz).

4-bromo-3-(4-{[(2S,6R)-2,6-dimethylmorpholino]methyl}benzyloxy)thiophene-2-carboxylic acid $^1$H-NMR (CDCl$_3$) δ 7.46 (2H, d, J=8.1 Hz), 7.41 (2H, d, J=8.1 Hz), 7.29 (1H, s), 5.31 (2H, s), 3.95-4.03 (2H, m), 3.93 (2H, s), 3.18 (2H, d, J=11.1 Hz), 2.13 (2H, brt, J=11.3 Hz), 1.16 (6H, d, J=6.3 Hz).

(38-2) To a solution of 4-bromo-3-(4-{[(2S,6R)-2,6-dimethylmorpholino]methyl}benzyloxy)thiophene-2-carboxylic acid (1.44 g, 3.27 mmol) in dimethyl sulfoxide (7.5 mL) were added silver carbonate (186 mg, 0.67 mmol) and acetic acid (0.22 mL, 3.84 mmol), and the mixture was stirred at 120° C. for 1.5 hr. To the reaction mixture was added 1.0 M hydrochloric acid, and the mixture was neutralized with saturated aqueous sodium bicarbonate. The mixture was extracted with ethyl acetate and washed with saturated brine. The organic layer was dried over anhydrous magnesium sulfate and concentrated to give (2S,6R)-4-{4-[(4-bromothiophen-3-yloxy)methyl]benzyl}-2,6-dimethylmorpholine (1.29 g, 99%) as a brown oil. The obtained (2S,6R)-4-{4-[(4-bromothiophen-3-yloxy)methyl]benzyl}-2,6-dimethylmorpholine was used for the next reaction without purification.

$^1$H-NMR (CDCl$_3$) δ 7.40 (2H, d, J=8.1 Hz), 7.34 (2H, d, J=8.1 Hz), 7.19 (1H, d, J=3.5 Hz), 6.28 (1H, d, J=3.5 Hz), 5.07 (2H, s), 3.64-3.74 (2H, m), 3.47 (2H, s), 2.66-2.74 (2H, m), 1.75 (2H, dd, J=10.3, 11.2 Hz), 1.13 (6H, d, J=6.3 Hz).

(38-3) By a method similar to that in Example 36 (36-4, 36-5), 3-{4-[4-(4-{[(2S,6R)-2,6-dimethylmorpholino]methyl}benzyloxy)thiophen-3-yl]-1H-1,2,3-triazol-1-yl}piperidine-2,6-dione was obtained as a white solid (53% yield) from (2S,6R)-4-{4-[(4-bromothiophen-3-yloxy)methyl]benzyl}-2,6-dimethylmorpholine.

(2S,6R)-2,6-dimethyl-4-[4-({4-[(trimethylsilyl)ethynyl]thiophen-3-yloxy}methyl)benzyl]morpholine $^1$H-NMR (CDCl$_3$) δ 7.41 (2H, d, J=8.1 Hz), 7.37 (1H, d, J=3.3 Hz), 7.33 (2H, d, J=8.1 Hz), 6.23 (1H, d, J=3.3 Hz), 5.07 (2H, s), 3.64-3.74 (2H, m), 3.49 (2H, s), 2.70 (2H, brd, J=10.6 Hz), 1.75 (2H, t, J=10.7 Hz), 1.13 (6H, d, J=6.3 Hz), 0.24 (9H, s).

(2S,6R)-4-{4-[(4-ethynylthiophen-3-yloxy)methyl]benzyl}-2,6-dimethylmorpholine $^1$H-NMR (CDCl$_3$) δ 7.30-7.42 (5H, m), 6.23 (1H, d, J=3.3 Hz), 5.08 (2H, s), 3.64-3.73 (2H, m), 3.47 (2H, s), 3.17 (1H, s), 2.66-2.73 (2H, m), 1.74 (2H, dd, J=10.5, 11.1 Hz), 1.13 (6H, d, J=6.3 Hz).

3-{4-[4-(4-{[(2S,6R)-2,6-dimethylmorpholino]methyl}benzyloxy)thiophen-3-yl]-1H-1,2,3-triazol-1-yl}piperidine-2,6-dione $^1$H-NMR (CDCl$_3$) δ 8.84-9.26 (1H, br), 7.94 (1H, s), 7.91 (1H, d, J=3.4 Hz), 7.40 (2H, d, J=8.1 Hz), 7.34 (2H, d, J=8.1 Hz), 6.41 (1H, d, J=3.4 Hz), 5.31 (1H, dd, J=5.2, 10.2 Hz), 5.09 and 5.13 (2H, ABq, J=11.1 Hz), 3.62-3.74 (2H, m), 3.46 and 3.57 (2H, ABq, J=13.0 Hz), 2.89-3.01 (1H, m), 2.54-2.84 (5H, m), 1.85 (1H, t, J=10.8 Hz), 1.77 (1H, t, J=10.8 Hz), 1.15 (3H, d, J=6.4 Hz), 1.14 (3H, d, J=6.4 Hz).

Example 39 (Compound 39)

3-(4-{4-[3-(morpholinomethyl)benzyloxy]thiophen-3-yl}-1H-1,2,3-triazol-1-yl)piperidine-2,6-dione By a method similar to that in Example 38, 3-(4-{4-[3-(morpholinomethyl)benzyloxy]thiophen-3-yl}-1H-1,2,3-triazol-1-yl)piperidine-2,6-dione was obtained as a blue-white solid (10% yield) from methyl 4-bromo-3-hydroxythiophene-2-carboxylate, α,α'-dibromo-m-xylene and morpholine.

methyl 4-bromo-3-[3-(bromomethyl)benzyloxy]thiophene-2-carboxylate $^1$H-NMR (CDCl$_3$) δ 7.56-7.59 (1H, brs), 7.45-7.50 (1H, m), 7.41 (1H, s), 7.36-7.40 (2H, m), 5.20 (2H, s), 4.52 (2H, s), 3.88 (3H, s).

methyl 4-bromo-3-[3-(morpholinomethyl)benzyloxy]thiophene-2-carboxylate $^1$H-NMR (CDCl$_3$) δ 7.42-7.48 (2H, m), 7.39 (1H, s), 7.29-7.37 (2H, m), 5.21 (2H, s), 3.88 (3H, s), 3.71 (4H, brt, J=4.7 Hz), 3.52 (2H, s), 2.44 (4H, brt, J=4.5 Hz).

4-bromo-3-[3-(morpholinomethyl)benzyloxy]thiophene-2-carboxylic acid $^1$H-NMR (CDCl$_3$) δ 11.07-11.47 (1H, brs), 7.54-7.62 (1H, brs), 7.50 (1H, brd, J=6.8 Hz), 7.22-7.35 (3H, m), 5.22 (2H, s), 3.92 (2H, s), 3.82 (4H, brt, J=4.6 Hz), 2.71-2.95 (4H, br).

4-{3-[(4-bromothiophen-3-yloxy)methyl]benzyl}morpholine $^1$H-NMR (CDCl$_3$) δ 7.39-7.42 (1H, brs), 7.26-7.37 (3H, m), 7.19 (1H, d, J=3.5 Hz), 6.27 (1H, d, J=3.5 Hz), 5.08 (2H, s), 3.70 (4H, brt, J=4.7 Hz), 3.51 (2H, s), 2.44 (4H, brt, J=4.5 Hz).

4-[3-({4-[(trimethylsilyl)ethynyl]thiophen-3-yloxy}methyl)benzyl]morpholine $^1$H-NMR (CDCl$_3$) δ 7.39-7.42 (1H, br), 7.27-7.39 (4H, m), 6.22 (1H, d, J=3.3 Hz), 5.08 (2H, s), 3.70 (4H, brt, J=4.6 Hz), 3.51 (2H, s), 2.43 (4H, brt, J=4.5 Hz), 0.25 (9H, s).

4-{3-[(4-ethynylthiophen-3-yloxy)methyl]benzyl}morpholine $^1$H-NMR (CDCl$_3$) δ 7.39-7.43 (2H, m), 7.27-7.37 (3H, m), 6.21 (1H, d, J=3.3 Hz), 5.10 (2H, s), 3.70 (4H, brt, J=4.6 Hz), 3.51 (2H, s), 3.17 (1H, s), 2.43 (4H, brt, J=4.5 Hz).

3-(4-{4-[3-(morpholinomethyl)benzyloxy]thiophen-3-yl}-1H-1,2,3-triazol-1-yl)piperidine-2,6-dione $^1$H-NMR (DMSO-d$_6$) δ 11.16-11.30 (1H, br), 8.27 (1H, s), 7.88 (1H, d, J=3.4 Hz), 7.31-7.43 (3H, m), 7.26 (1H, brd, J=7.2 Hz), 6.80 (1H, d, J=3.4 Hz), 5.85 (1H, dd, J=5.1, 12.4 Hz), 5.22 (2H, s), 3.53 (4H, brt, J=4.5 Hz), 3.46 (2H, s), 2.63-2.94 (3H, m), 2.21-2.41 (5H, m).

Example 40 (Compound 40)

3-(4-{4-[2-(morpholinomethyl)benzyloxy]thiophen-3-yl}-1H-1,2,3-triazol-1-yl)piperidine-2,6-dione (40-1) By a method similar to that in Example 38 (38-1, 38-2), 4-{2-[(4-bromothiophen-3-yloxy)methyl]benzyl}morpholine was obtained as a brown oil (64% yield)

from methyl 4-bromo-3-hydroxythiophene-2-carboxylate, α,α'-dibromo-o-xylene and morpholine.

methyl 4-bromo-3-[2-(bromomethyl)benzyloxy]thiophene-2-carboxylate $^1$H-NMR (CDCl$_3$) δ 7.56-7.62 (1H, m), 7.41-7.46 (2H, m), 7.34-7.39 (2H, m), 5.32 (2H, s), 4.86 (2H, s), 3.90 (3H, s).

methyl 4-bromo-3-[2-(morpholinomethyl)benzyloxy]thiophene-2-carboxylate $^1$H-NMR (CDCl$_3$) δ 7.63-7.69 (1H, m), 7.41 (1H, s), 7.24-7.35 (3H, m), 5.42 (2H, s), 3.86 (3H, s), 3.66 (2H, s), 3.64 (4H, brt, J=4.6 Hz), 2.43 (4H, brt, J=4.4 Hz).

4-{2-[(4-bromothiophen-3-yloxy)methyl]benzyl}morpholine $^1$H-NMR (CDCl$_3$) δ 7.50 (1H, brd, J=6.6 Hz), 7.22-7.34 (3H, m), 7.18 (1H, d, J=3.5 Hz), 6.35 (1H, d, J=3.5 Hz), 5.29 (2H, s), 3.64 (4H, brt, J=4.6 Hz), 3.57 (2H, s), 2.41 (4H, brt, J=4.4 Hz).

(40-2) To a solution of 4-{2-[(4-bromothiophen-3-yloxy)methyl]benzyl}morpholine (680.2 mg, 1.85 mmol) in N,N-dimethylformamide (3.5 mL) were added bis(triphenylphosphine)palladium(II) dichloride (128.6 mg, 0.18 mmol), triethylamine (1.52 mL, 10.91 mmol) and trimethylsilylacetylene (1.25 mL, 9.04 mmol), and the mixture was stirred under an argon atmosphere at 70° C. for 6.5 hr. The reaction mixture was diluted with ethyl acetate, saturated aqueous ammonium chloride was added, and the mixture was extracted with ethyl acetate. The organic layer was washed with saturated brine, dried over anhydrous magnesium sulfate and concentrated. The concentrated residue was purified by column chromatography (hexane/ethyl acetate) to give 4-[2-({4-[(trimethylsilyl)ethynyl]thiophen-3-yloxy}methyl)benzyl]morpholine (602.8 mg, 84%) as a red-brown oil.

$^1$H-NMR (CDCl$_3$) δ 7.57 (1H, brd, J=7.1 Hz), 7.37 (1H, d, J=3.3 Hz), 7.22-7.34 (3H, m), 6.26 (1H, d, J=3.3 Hz), 5.29 (2H, s), 3.61-3.68 (4H, m), 3.59 (2H, s), 2.36-2.47 (4H, m), 0.23 (9H, s).

(40-3) By a method similar to that in Example 8 (8-2, 8-3), 3-(4-{4-[2-(morpholinomethyl)benzyloxy]thiophen-3-yl}-1H-1,2,3-triazol-1-yl)piperidine-2,6-dione was obtained as a blue-white solid (40% yield) from 4-[2-({4-[(trimethylsilyl)ethynyl]thiophen-3-yloxy}methyl)benzyl]morpholine.

4-{2-[(4-ethynylthiophen-3-yloxy)methyl]benzyl}morpholine $^1$H-NMR (CDCl$_3$) δ 7.48-7.53 (1H, m), 7.42 (1H, d, J=3.3 Hz), 7.23-7.33 (3H, m), 6.31 (1H, d, J=3.3 Hz), 5.31 (2H, s), 3.65 (4H, brt, J=4.6 Hz), 3.58 (2H, s), 3.16 (1H, s), 2.42 (4H, brt, J=4.4 Hz).

3-(4-{4-[2-(morpholinomethyl)benzyloxy]thiophen-3-yl}-1H-1,2,3-triazol-1-yl)piperidine-2,6-dione $^1$H-NMR (DMSO-d$_6$) δ 11.18-11.26 (1H, br), 8.25 (1H, s), 7.89 (1H, d, J=3.4 Hz), 7.45-7.52 (1H, m), 7.25-7.36 (3H, m), 6.83 (1H, d, J=3.4 Hz), 5.85 (1H, dd, J=5.0, 12.4 Hz), 5.38 (2H, s), 3.55 (2H, s), 3.51 (4H, brt, J=4.3 Hz), 2.63-2.91 (3H, m), 2.24-2.41 (5H, m).

Example 41 (Compound 41)

3-(4-{4-[4-(pyrrolidin-1-ylmethyl)benzyloxy]thiophen-3-yl}-1H-1,2,3-triazol-1-yl)piperidine-2,6-dione hydrochloride By a method similar to that in Example 38 (38-1, 38-2) and Example 11, 3-(4-{4-[4-(pyrrolidin-1-ylmethyl)benzyloxy]thiophen-3-yl}-1H-1,2,3-triazol-1-yl)piperidine-2,6-dione was obtained as a red-brown oil (18% yield) from methyl 4-bromo-3-hydroxythiophene-2-carboxylate, α,α'-dibromo-p-xylene and pyrrolidine.

To a solution of the obtained 3-(4-{4-[4-(pyrrolidin-1-ylmethyl)benzyloxy]thiophen-3-yl}-1H-1,2,3-triazol-1-yl)piperidine-2,6-dione (316.9 mg, 0.70 mmol) in ethyl acetate (2 mL) was added 4.0 M hydrochloric acid/ethyl acetate solution (193.0 μL) at 0° C. and the mixture was stirred at 0° C. for 1 hr. The precipitate was collected by filtration, and the residue was recrystallized from acetone-methanol to give 3-(4-{4-[4-(pyrrolidin-1-ylmethyl)benzyloxy]thiophen-3-yl}-1H-1,2,3-triazol-1-yl)piperidine-2,6-dione hydrochloride (159.1 mg, 47%) as a pale-brown solid.

methyl 4-bromo-3-[4-(pyrrolidin-1-ylmethyl)benzyloxy]thiophene-2-carboxylate $^1$H-NMR (CDCl$_3$) δ 7.46-7.58 (4H, m), 7.41 (1H, s), 5.20 (2H, s), 3.88 (5H, s), 2.69-3.00 (4H, br), 1.85-2.09 (4H, br).

4-bromo-3-[4-(pyrrolidin-1-ylmethyl)benzyloxy]thiophene-2-carboxylic acid

MS m/z 398[M+1]$^+$, 396[M+1]$^+$

1-{4-[(4-bromothiophen-3-yloxy)methyl]benzyl}pyrrolidine $^1$H-NMR (CDCl$_3$) δ 7.32-7.45 (4H, m), 7.19 (1H, d, J=3.5 Hz), 6.27 (1H, d, J=3.5 Hz), 5.07 (2H, s), 3.62 (2H, s), 2.47-2.56 (4H, m), 1.75-1.84 (4H, m).

1-[4-({4-[(trimethylsilyl)ethynyl]thiophen-3-yloxy}methyl)benzyl]pyrrolidine $^1$H-NMR (CDCl$_3$) δ 7.31-7.42 (5H, m), 6.22 (1H, d, J=3.3 Hz), 5.07 (2H, s), 3.62 (2H, s), 2.47-2.54 (4H, m), 1.74-1.84 (4H, m), 0.24 (9H, s).

1-{4-[(4-ethynylthiophen-3-yloxy)methyl]benzyl}pyrrolidine $^1$H-NMR (CDCl$_3$) δ 7.30-7.44 (5H, m), 6.22 (1H, d, J=3.4 Hz), 5.09 (2H, s), 3.61 (2H, s), 3.17 (1H, s), 2.45-2.56 (4H, m), 1.73-1.84 (4H, m).

3-(4-{4-[4-(pyrrolidin-1-ylmethyl)benzyloxy]thiophen-3-yl}-1H-1,2,3-triazol-1-yl)piperidine-2,6-dione hydrochloride $^1$H-NMR (DMSO-d$_6$) δ 11.22 (1H, s), 10.82-10.99 (1H, br), 8.31 (1H, s), 7.88 (1H, d, J=3.4 Hz), 7.53-7.66 (4H, m), 6.83 (1H, d, J=3.4 Hz), 5.89 (1H, dd, J=5.0, 12.4 Hz), 5.25 (2H, s), 4.32 (2H, d, J=5.8 Hz), 3.26-3.39 (2H, m), 2.96-3.10 (2H, m), 2.81-2.95 (1H, m), 2.65-2.81 (2H, m), 2.29-2.39 (1H, m), 1.94-2.07 (2H, m), 1.79-1.94 (2H, m).

Example 42 (Compound 42)

3-(4-{4-[4-(piperidin-1-ylmethyl)benzyloxy]thiophen-3-yl}-1H-1,2,3-triazol-1-yl)piperidine-2,6-dione hydrochloride (42-1) To a suspension of methyl 4-bromo-3-[4-(bromomethyl)benzyloxy]thiophene-2-carboxylate (synthesized by the method of Example 36 (36-1)) (1.17 g, 2.78 mmol) in water (7 mL) were added potassium hydroxide (85%) (0.53 g, 8.03 mmol) and acetone (5 mL) and the mixture was refluxed for 3 hr. The reaction mixture was concentrated, water was added to the concentrated residue and the mixture was washed with diethyl ether. To the aqueous layer was added 2.0 M hydrochloric acid (5.0 mL), and the mixture was extracted with ethyl acetate. The organic layer was washed with saturated brine, dried over anhydrous magnesium sulfate and concentrated to give 4-bromo-3-[4-(hydroxymethyl)benzyloxy]thiophene-2-carboxylic acid (0.94 g, 99%) as a white solid.

$^1$H-NMR (CD$_3$OD) δ 7.66 (1H, s), 7.46-7.52 (2H, m), 7.32-7.37 (2H, m), 5.20 (2H, s), 4.61 (2H, s).

(42-2) By a method similar to that in Example 37 (37-2), {4-[(4-bromothiophen-3-yloxy)methyl]phenyl}methanol (0.67 g, 82%) was obtained as a brown solid from 4-bromo-3-[4-(hydroxymethyl)benzyloxy]thiophene-2-carboxylic acid (0.94 g, 2.74 mmol).

$^1$H-NMR (CDCl$_3$) δ 7.37-7.47 (4H, m), 7.20 (1H, d, J=3.5 Hz), 6.27 (1H, d, J=3.5 Hz), 5.09 (2H, s), 4.72 (2H, d, J=5.8 Hz), 1.65 (1H, t, J=5.9 Hz).

(42-3) To a solution of {4-[(4-bromothiophen-3-yloxy)methyl]phenyl}methanol (0.67 g, 2.24 mmol) and triethylamine (0.62 mL, 4.45 mmol) in dichloromethane (9 mL) was added dropwise methanesulfonyl chloride (0.26 mL, 3.36 mmol) under an argon atmosphere at −20° C., and the mixture was stirred at −20° C. for 1 hr. The reaction mixture was diluted with dichloromethane, and washed with water, 2.0 M hydrochloric acid and saturated brine. The organic layer was dried over anhydrous magnesium sulfate and concentrated to give 4-[(4-bromothiophen-3-yloxy)methyl]benzyl methanesulfonate mixture (0.94 g) as a pale-yellow oil. The obtained 4-[(4-bromothiophen-3-yloxy)methyl]benzyl methanesulfonate mixture was used for the next reaction without purification.

$^1$H-NMR (CDCl$_3$) δ 7.41-7.53 (4H, m), 7.21 (1H, d, J=3.4 Hz), 6.28 (1H, d, J=3.5H), 5.25 (2H, s), 5.11 (2H, s), 2.94 (3H, s).

(42-4) Under an argon atmosphere at 0° C., to a suspension of sodium hydride (60%) (0.11 g, 2.75 mmol) in N,N-dimethylformamide (7.5 mL) was added dropwise piperidine (0.27 mL, 2.73 mmol), and the mixture was stirred at 0° C. for 20 min. To the suspension was added dropwise a solution of a 4-[(4-bromothiophen-3-yloxy)methyl]benzyl methanesulfonate mixture (0.94 g) in N,N-dimethylformamide (4 mL) at 0° C., and the mixture was stirred at 0° C. to room temperature for 18 hr. To the reaction mixture was added saturated aqueous ammonium chloride and the mixture was extracted with ethyl acetate. The organic layer was washed with saturated brine, dried over anhydrous magnesium sulfate and concentrated. The concentrated residue was purified by column chromatography (dichloromethane/methanol) to give 1-{4-[(4-bromothiophen-3-yloxy)methyl]benzyl}piperidine (0.82 g, 2 step 99%) as a yellow oil.

$^1$H-NMR (CDCl$_3$) δ 7.30-7.42 (4H, m), 7.19 (1H, d, J=3.4 Hz), 6.28 (1H, d, J=3.5 Hz), 5.07 (2H, s), 3.49 (2H, s), 2.39 (4H, brs), 1.53-1.63 (4H, m), 1.38-1.48 (2H, m).

(42-5) By a method similar to that in Example 11, 3-(4-{4-[4-(piperidin-1-ylmethyl)benzyloxy]thiophen-3-yl}-1H-1,2,3-triazol-1-yl)piperidine-2,6-dione was obtained as a pale-brown amorphous substance (10% yield) from 1-{4-[(4-bromothiophen-3-yloxy)methyl]benzyl}piperidine.

To a suspension of 3-(4-{4-[4-(piperidin-1-ylmethyl)benzyloxy]thiophen-3-yl}-1H-1,2,3-triazol-1-yl)piperidine-2,6-dione (212.9 mg, 0.46 mmol) in ethyl acetate (2 mL) was added 4.0 M hydrochloric acid/ethyl acetate solution (125.7 μL) at 0° C., and the mixture was stirred at 0° C. for 1 hr. The precipitate was collected by filtration, and the residue was recrystallized from ethyl acetate-methanol to give 3-(4-{4-[4-(piperidin-1-ylmethyl)benzyloxy]thiophen-3-yl}-1H-1,2,3-triazol-1-yl)piperidine-2,6-dione hydrochloride (133.0 mg, 57%) as a gray solid.

1-[4-({4-[(trimethylsilyl)ethynyl]thiophen-3-yloxy}methyl)benzyl]piperidine $^1$H-NMR (CDCl$_3$) δ 7.28-7.45 (5H, m), 6.23 (1H, d, J=3.3 Hz), 5.07 (2H, s), 3.48 (2H, s), 2.28-2.45 (4H, br), 1.52-1.61 (4H, m), 1.37-1.47 (2H, m), 0.24 (9H, s).

1-{4-[(4-ethynylthiophen-3-yloxy)methyl]benzyl}piperidine $^1$H-NMR (CDCl$_3$) δ 7.41 (1H, d, J=3.3 Hz), 7.30-7.40 (4H, m), 6.23 (1H, d, J=3.3 Hz), 5.08 (2H, s), 3.47 (2H, s), 3.17 (1H, s), 2.27-2.46 (4H, br), 1.52-1.64 (4H, m), 1.36-1.48 (2H, m).

3-(4-{4-[4-(piperidin-1-ylmethyl)benzyloxy]thiophen-3-yl}-1H-1,2,3-triazol-1-yl)piperidine-2,6-dione hydrochloride $^1$H-NMR (DMSO-d$_6$) δ 11.22 (1H, brs), 10.52-10.70 (1H, br), 8.32 (1H, s), 7.88 (1H, d, J=3.3 Hz), 7.54-7.66 (4H, m), 6.84 (1H, d, J=3.4 Hz), 5.89 (1H, dd, J=5.0, 12.4 Hz), 5.25 (2H, s), 4.23 (2H, d, J=5.3 Hz), 3.26 (2H, brd, J=11.8 Hz), 2.65-2.96 (5H, m), 2.28-2.40 (1H, m), 1.63-1.87 (5H, m), 1.24-1.43 (1H, m).

Example 43 (Compound 43)

3-{4-[4-(4-chlorobenzyloxy)thiophen-3-yl]-1H-1,2,3-triazol-1-yl}piperidine-2,6-dione (43-1) To a solution of methyl 4-bromo-3-hydroxythiophene-2-carboxylate (1.00 g, 4.22 mmol) in tetrahydrofuran (85 mL) were added p-chloro benzyl alcohol (0.90 g, 6.31 mmol) and triphenylphosphine (2.21 g, 8.43 mmol), and diisopropyl azodicarboxylate (1.66 mL, 8.43 mmol) was added dropwise thereto at 0° C. Under an argon atmosphere, and the mixture was stirred at 0° C. to room temperature for 17 hr. The reaction mixture was concentrated, and the concentrated residue was purified by column chromatography (hexane/ethyl acetate) to give methyl 4-bromo-3-(4-chlorobenzyloxy)thiophene-2-carboxylate (1.48 g, 97%) as a white solid.

$^1$H-NMR (CDCl$_3$) δ 7.45-7.52 (2H, m), 7.41 (1H, s), 7.33-7.39 (2H, m), 5.17 (2H, s), 3.88 (3H, s).

(43-2) By a method similar to that in Example 33 (33-2) and Example 38 (38-2), 3-bromo-4-(4-chlorobenzyloxy)thiophene was obtained as a white solid (97% yield) from methyl 4-bromo-3-(4-chlorobenzyloxy)thiophene-2-carboxylate.

4-bromo-3-(4-chlorobenzyloxy)thiophene-2-carboxylic acid

¹H NMR (CD₃OD) δ 7.68 (1H, s), 7.48-7.54 (2H, m), 7.33-7.40 (2H, m), 5.18 (2H, s).

3-bromo-4-(4-chlorobenzyloxy)thiophene

¹H-NMR (CDCl₃) δ 7.33-7.42 (4H, m), 7.20 (1H, d, J=3.5 Hz), 6.27 (1H, d, J=3.5 Hz), 5.05 (2H, s).

(43-3) By a method similar to that in Example 11, 3-{4-[4-(4-chlorobenzyloxy)thiophen-3-yl]-1H-1,2,3-triazol-1-yl}piperidine-2,6-dione was obtained as a white solid (19% yield) from 3-bromo-4-(4-chlorobenzyloxy)thiophene.

{[4-(4-chlorobenzyloxy)thiophen-3-yl]ethynyl}trimethylsilane

¹H-NMR (CDCl₃) δ 7.32-7.44 (5H, m), 6.22 (1H, d, J=3.3 Hz), 5.05 (2H, s), 0.25 (9H, s).

3-(4-chlorobenzyloxy)-4-ethynylthiophene

¹H-NMR (CDCl₃) δ 7.42 (1H, d, J=3.3 Hz), 7.32-7.41 (4H, m), 6.21 (1H, d, J=3.3 Hz), 5.07 (2H, s), 3.18 (1H, s).

3-{4-[4-(4-chlorobenzyloxy)thiophen-3-yl]-1H-1,2,3-triazol-1-yl}piperidine-2,6-dione ¹H-NMR (DMSO-d₆) δ 11.23 (1H, brs), 8.28 (1H, s), 7.89 (1H, d, J=3.4 Hz), 7.50-7.55 (2H, m), 7.44-7.49 (2H, m), 6.82 (1H, d, J=3.4 Hz), 5.85 (1H, dd, J=5.2, 12.5 Hz), 5.21 (2H, s), 2.64-2.93 (3H, m), 2.28-2.40 (1H, m).

Example 44 (Compound 44)

3-{4-[4-(1-phenylethoxy)thiophen-3-yl]-1H-1,2,3-triazol-1-yl}piperidine-2,6-dione By a method similar to that in Example 43, an optical isomer mixture of 3-{4-[4-(1-phenylethoxy)thiophen-3-yl]-1H-1,2,3-triazol-1-yl}piperidine-2,6-dione was obtained as a white solid (15% yield) from methyl 4-bromo-3-hydroxythiophene-2-carboxylate and (±)-1-phenylethylalcohol.

methyl 4-bromo-3-(1-phenylethoxy)thiophene-2-carboxylate

¹H-NMR (CDCl₃) δ 7.43-7.50 (2H, m), 7.33 (1H, s), 7.24-7.38 (3H, m), 5.75 (1H, q, J=6.5 Hz), 3.83 (3H, s), 1.68 (3H, d, J=6.5 Hz).

4-bromo-3-(1-phenylethoxy)thiophene-2-carboxylic acid

¹H-NMR (CDCl₃) δ 7.45 (1H, s), 7.42-7.47 (2H, m), 7.28-7.38 (3H, m), 5.85 (1H, q, J=6.5 Hz), 1.73 (3H, d, J=6.5 Hz).

3-bromo-4-(1-phenylethoxy)thiophene

¹H-NMR (CDCl₃) δ 7.32-7.41 (4H, m), 7.24-7.30 (1H, m), 7.12 (1H, d, J=3.4 Hz), 6.02 (1H, d, J=3.5 Hz), 5.18 (1H, q, J=6.5 Hz), 1.67 (3H, d, J=6.4 Hz).

trimethyl{[4-(1-phenylethoxy)thiophen-3-yl]ethynyl}silane

¹H-NMR (CDCl₃) δ 7.23-7.44 (6H, m), 6.00 (1H, d, J=3.3 Hz), 5.20 (1H, q, J=6.4 Hz), 1.65 (3H, d, J=6.4 Hz), 0.27 (9H, s).

3-ethynyl-4-(1-phenylethoxy)thiophene

¹H-NMR (CDCl₃) δ 7.24-7.41 (6H, m), 5.98 (1H, d, J=3.3 Hz), 5.20 (1H, q, J=6.5 Hz), 3.20 (1H, s), 1.67 (3H, d, J=6.5 Hz).

3-{4-[4-(1-phenylethoxy)thiophen-3-yl]-1H-1,2,3-triazol-1-yl}piperidine-2,6-dione ¹H-NMR (DMSO-d₆) δ 11.26 (1H, s), 8.45 (0.8H, s, major), 8.43 (0.2H, s, minor), 7.82 (1H, d, J=3.4 Hz), 7.43-7.48 (2H, m), 7.31-7.38 (2H, m), 7.23-7.30 (1H, m), 6.55 (0.2H, d, J=3.4 Hz, minor), 6.52 (0.8H, d, J=3.4 Hz, major), 5.92 (1H, dd, J=4.9, 12.2 Hz), 5.46 (1H, q, J=6.3 Hz), 2.66-2.96 (3H, m), 2.31-2.41 (1H, m), 1.64 (3H, d, J=6.4 Hz).

Example 45 (Compound 45)

3-(4-{4-[4-(2-morpholinoethyl)benzyloxy]thiophen-3-yl}-1H-1,2,3-triazol-1-yl)piperidine-2,6-dione hydrochloride (45-1) By a method similar to that in Example 43 (43-1) and Example 33 (33-2), 4-bromo-3-[4-(2-morpholinoethyl)benzyloxy]thiophene-2-carboxylic acid was obtained as a white solid (86% yield) from methyl 4-bromo-3-hydroxythiophene-2-carboxylate and [4-(2-morpholinoethyl)phenyl]methanol.

methyl 4-bromo-3-[4-(2-morpholinoethyl)benzyloxy]thiophene-2-carboxylate

¹H-NMR (CDCl₃) δ 7.47 (2H, d, J=8.1 Hz), 7.40 (1H, s), 7.23 (2H, d, J=8.1 Hz), 5.16 (2H, s), 3.87 (3H, s), 3.74 (4H, t, J=4.7 Hz), 2.78-2.86 (2H, m), 2.56-2.63 (2H, m), 2.46-2.56 (4H, m).

4-bromo-3-[4-(2-morpholinoethyl)benzyloxy]thiophene-2-carboxylic acid

¹H-NMR (DMSO-d₆) δ 7.95 (1H, s), 7.36-7.41 (2H, m), 7.22-7.27 (2H, m), 5.13 (2H, s), 3.54-3.63 (4H, m), 2.72-2.80 (2H, m), 2.43-2.59 (6H, m).

(45-2) To a solution of 4-bromo-3-[4-(2-morpholinoethyl)benzyloxy]thiophene-2-carboxylic acid (331.0 mg, 0.78 mmol) in dimethylsulfoxide (3.9 mL) were added silver carbonate (24.0 mg, 0.09 mmol) and acetic acid (49 µL, 0.86 mmol), and the mixture was stirred at 120° C. for 15 min. Silver carbonate (48.6 mg, 0.18 mmol) was added to divide two times at 5 min and 10 min later. The reaction mixture was cooled to room temperature, 1.0 M hydrochloric acid and ethyl acetate were added, and the mixture was stirred for some time, and neutralized with saturated aqueous sodium bicarbonate. The reaction mixture was filtered and extracted with ethyl acetate. The organic layer was washed with saturated brine, dried over anhydrous magnesium sulfate and concentrated. The concentrated residue (266.1 mg) was dissolved in chloroform (2 mL), 4.0 M hydrochloric acid/ethyl acetate solution (0.3 mL, 1.2 mmol), and then diethyl ether (2 mL) were added, and the precipitate was collected by filtration to give 4-{4-[(4-bromothiophen-3-yloxy)methyl]phenethyl}morpholine hydrochloride (278.4 mg, 85%) as a white solid.

$^1$H-NMR (DMSO-d$_6$) δ 10.73-10.96 (1H, br), 7.66 (1H, d, J=3.5 Hz), 7.41-7.47 (2H, m), 7.29-7.35 (2H, m), 6.84 (1H, d, J=3.5 Hz), 5.08 (2H, s), 3.94-4.03 (2H, m), 3.77 (2H, brt, J=11.5 Hz), 3.44-3.53 (2H, m), 3.28-3.38 (2H, m), 3.02-3.16 (4H, m).

(45-3) By a method similar to that in Example 40 (40-2), 4-[4-({4-[(trimethylsilyl)ethynyl]thiophen-3-yloxy}methyl)phenethyl]morpholine (192.8 mg, 73%) was obtained as a red-brown oil from 4-{4-[(4-bromothiophen-3-yloxy)methyl]phenethyl}morpholine hydrochloride (278.4 mg, 0.66 mol).

$^1$H-NMR (CDCl$_3$) δ 7.35-7.40 (3H, m), 7.19-7.24 (2H, m), 6.22 (1H, d, J=3.3 Hz), 5.06 (2H, s), 3.72-3.77 (4H, m), 2.78-2.85 (2H, m), 2.48-2.63 (6H, m), 0.25 (9H, s).

(45-4) To a solution of 4-[4-({4-[(trimethylsilyl)ethynyl]thiophen-3-yloxy}methyl)phenethyl]morpholine (164.9 mg, 0.41 mmol) and acetic acid (0.24 mL, 4.19 mmol) in tetrahydrofuran (1.7 mL) was added 1 M tetrabutylammonium fluoride/tetrahydrofuran solution (2.1 mL, 2.10 mmol) at 0° C. and the mixture was stirred at 0° C. to room temperature for 6 hr. The reaction mixture was diluted with ethyl acetate, washed with saturated aqueous sodium bicarbonate and saturated brine, dried over anhydrous magnesium sulfate and concentrated. The concentrated residue was purified by column chromatography (ethyl acetate/methanol) to give 4-{4-[(4-ethynylthiophen-3-yloxy)methyl]phenethyl}morpholine (116.1 mg, 85%) as a red-brown oil.

$^1$H-NMR (CDCl$_3$) δ 7.41 (1H, d, J=3.4 Hz), 7.34-7.39 (2H, m), 7.19-7.24 (2H, m), 6.22 (1H, d, J=3.4 Hz), 5.07 (2H, s), 3.75 (4H, brt, J=4.6 Hz), 3.17 (1H, s), 2.77-2.87 (2H, m), 2.49-2.65 (6H, m).

(45-5) To a suspension of 4-{4-[(4-ethynylthiophen-3-yloxy)methyl]phenethyl}morpholine (101.8 mg, 0.31 mmol) in tert-butyl alcohol (1.2 mL) and water (1.2 mL) were added 3-azidopiperidine-2,6-dione (synthesized by the method of Example 1 (1-1)) (53.2 mg, 0.35 mmol), copper (II) sulfate pentahydrate (7.2 mg, 0.03 mmol) and sodium ascorbate (12.3 mg, 0.06 mmol), and the mixture was stirred under an argon atmosphere at room temperature for 17 hr. To the reaction mixture were added acetonitrile and methanol, and an insoluble material was dissolved, treated with activated carbon and concentrated. The concentrated residue was purified by column chromatography (dichloromethane/methanol) and the obtained compound was dissolved in ethyl acetate (1.5 mL) and methanol (0.5 mL), and 4.0 M hydrochloric acid/ethyl acetate solution (100 μL, 0.40 mmol) was added at 0° C. To the reaction mixture was added methanol, and the mixture was treated with activated carbon, and the solvent was evaporated. The residue was solidified in acetone to give 3-(4-{4-[4-(2-morpholinoethyl)benzyloxy]thiophen-3-yl}-1H-1,2,3-triazol-1-yl)piperidine-2,6-dione hydrochloride (39.8 mg, 26%) as a pale-brown solid.

$^1$H-NMR (DMSO-d$_6$) δ 11.24 (1H, brs), 11.07-11.30 (1H, br), 8.29 (1H, s), 7.88 (1H, d, J=3.3 Hz), 7.48 (2H, d, J=8.1 Hz), 7.30 (2H, d, J=8.1 Hz), 6.81 (1H, d, J=3.4 Hz), 5.88 (1H, dd, J=5.0, 12.3 Hz), 5.20 (2H, s), 3.98 (2H, brdd, J=2.3, 12.3 Hz), 3.80 (2H, brt, J=11.5 Hz), 3.47 (2H, brd, J=12.3 Hz), 3.25-3.37 (2H, m), 2.99-3.15 (4H, m), 2.63-2.95 (3H, m), 2.28-2.39 (1H, m).

Example 46 (Compound 46)

3-[4-(4-{4-[(dimethylamino)methyl]benzyloxy}thiophen-3-yl)-1H-1,2,3-triazol-1-yl]piperidine-2,6-dione hydrochloride (46-1) By a method similar to that in Example 36 (36-4), [4-({4-[(trimethylsilyl)ethynyl]thiophen-3-yloxy}methyl)phenyl]methanol (468.5 mg, 59%) was obtained as a red-brown oil from {4-[(4-bromothiophen-3-yloxy)methyl]phenyl}methanol (synthesized by the method of Example 42 (42-1, 42-2)) (754.3 mg, 2.52 mmol).

$^1$H-NMR (CDCl$_3$) δ 7.33-7.52 (5H, m), 6.22 (1H, d, J=3.3 Hz), 5.09 (2H, s), 4.71 (2H, d, J=5.9 Hz), 1.65 (1H, brt, J=6.0 Hz), 0.25 (9H, s).

(46-2) To a solution of [4-({4-[(trimethylsilyl)ethynyl]thiophen-3-yloxy}methyl)phenyl]methanol (468.5 mg, 1.48 mmol) in dichloromethane (5.9 mL) were added triethylamine (0.41 mL, 2.94 mmol) and methanesulfonyl chloride (0.17 mL, 2.20 mmol) at −20° C., and the mixture was stirred at −20° C. to −9° C. for 1 hr. The reaction mixture was diluted with dichloromethane, washed with 1.0 M hydrochloric acid and saturated brine, dried over anhydrous magnesium sulfate and concentrated. The concentrated residue (624.1 mg) was dissolved in dichloromethane (15 mL), 2 M dimethylamine/methanol solution (2.2 mL, 4.4 mmol) was added at 0° C., and the mixture was stirred at 0° C. to room temperature for 17.5 hr. To the reaction mixture was added saturated aqueous sodium bicarbonate and the mixture was extracted with dichloromethane. The organic layer was washed with saturated brine, dried over anhydrous magnesium sulfate and concentrated. The concentrated residue was purified by column chromatography (dichloromethane/methanol) to give 1-[4-({[4-(trimethylsilyl)ethynyl]thiophen-3-yloxy}methyl)phenyl]-N,N-dimethylmethaneamine mixture (373.7 mg) as a brown oil. To a solution of the obtained mixture (373.7 mg) in methanol (2.2 mL) was added potassium carbonate (303.9 mg, 2.20 mmol), and the mixture was stirred at room temperature for 25 hr. To the reaction mixture was added saturated brine and the mixture was extracted with ethyl acetate. The organic layer was washed with saturated brine, dried over anhydrous magnesium sulfate and concentrated. The concentrated residue was purified by column chromatography (dichloromethane/methanol) to give 1-{4-[(4-ethynylthiophen-3-yloxy)methyl]phenyl}-N,N-dimethylmethaneamine (175.7 mg, 44%) as a red-brown oil.

$^1$H-NMR (CDCl$_3$) δ 7.38-7.43 (3H, m), 7.29-7.35 (2H, m), 6.22 (1H, d, J=3.3 Hz), 5.09 (2H, s), 3.43 (2H, s), 3.17 (1H, s), 2.24 (6H, s).

(46-3) By a method similar to that in Example 1 (1-2), 3-[4-(4-{4-[(dimethylamino)methyl]benzyloxy}thiophen-3-yl)-1H-1,2,3-triazol-1-yl]piperidine-2,6-dione (227.5 mg) was obtained as a green oil from 1-{4-[(4-ethynylthiophen-3-yloxy)methyl]phenyl}-N,N-dimethylmethaneamine (175.7 mg, 0.65 mmol).

The obtained green oil (227.5 mg) was dissolved in ethyl acetate (2 mL) and methanol (2 mL), and 4.0 M hydrochloric acid/ethyl acetate solution (0.3 mL, 1.20 mmol) was added at room temperature. The solvent was evaporated, and the residue was dissolved in methanol and treated with activated carbon. The solvent was evaporated, and the obtained residue was suspended in methanol (0.5 mL). An insoluble material was removed by filtration and the filtrate was concentrated. The concentrated residue was dissolved in methanol (0.3 mL) at 40° C. and stood at 5° C. to allow for precipitation of a solid. Methanol (1.0 mL) was added, and the precipitate was collected by filtration, and washed with methanol, ethyl acetate and diethyl ether to give 3-[4-(4-{4-[(dimethylamino)methyl]benzyloxy}thiophen-3-yl)-1H-1,2,3-triazol-1-yl]piperidine-2,6-dione hydrochloride (87.6 mg, 29%) as a white solid.

$^1$H-NMR (DMSO-d$_6$) δ 11.23 (1H, brs), 10.07-10.60 (1H, br), 8.32 (1H, s), 7.88 (1H, d, J=3.4 Hz), 7.52-7.62 (4H, m), 6.82 (1H, d, J=3.4 Hz), 5.88 (1H, dd, J=5.0, 12.4 Hz), 5.26 (2H, s), 4.26 (2H, brs), 2.59-2.95 (9H, m), 2.28-2.40 (1H, m).

Example 47 (Compound 47)

3-{4-[4-(benzo[b]thiophen-2-ylmethoxy)thiophen-3-yl]-1H-1,2,3-triazol-1-yl}piperidine-2,6-dione (47-1) By a method similar to that in Example 43 (43-1), methyl 3-(benzo[b]thiophen-2-ylmethoxy)-4-bromothiophene-2-carboxylate (1.20 g, 93%) was obtained as a white solid from benzo[b]thiophene-2-methanol (0.72 g, 4.38 mmol) and methyl 4-bromo-3-hydroxythiophene-2-carboxylate (0.80 g, 3.37 mmol).

$^1$H-NMR (CDCl$_3$) δ 7.80-7.86 (1H, m), 7.73-7.79 (1H, m), 7.41 (1H, s), 7.37 (1H, brd, J=0.7 Hz), 7.31-7.38 (2H, m), 5.49 (2H, d, J=0.7 Hz), 3.90 (3H, s).

(47-2) Methyl 3-(benzo[b]thiophen-2-ylmethoxy)-4-bromothiophene-2-carboxylate (1.17 g, 3.05 mmol) was dissolved in tetrahydrofuran (70 mL)-water (9.4 mL) mixed solution, 1.25 M aqueous lithium hydroxide (18.8 mL, 23.5 mmol) was added at 0° C., and the mixture was stirred at 0° C. to room temperature for 17 hr. The reaction mixture was concentrated, 1.0 M hydrochloric acid (25 mL, 25 mmol) was added and the precipitate was collected by filtration to give 3-(benzo[b]thiophen-2-ylmethoxy)-4-bromothiophene-2-carboxylic acid (1.10 g, 98%) as a white solid.

$^1$H-NMR (DMSO-d$_6$) δ 7.90-8.00 (2H, m), 7.81-7.88 (1H, m), 7.47 (1H, s), 7.32-7.42 (2H, m), 5.53 (2H, s).

(47-3) By a method similar to that in Example 38 (38-2) and Example 40 (40-2, 40-3), 3-{4-[4-(benzo[b]thiophen-2-ylmethoxy)thiophen-3-yl]-1H-1,2,3-triazol-1-yl}piperidine-2,6-dione was obtained as a white solid (14% yield) from 3-(benzo[b]thiophen-2-ylmethoxy)-4-bromothiophene-2-carboxylic acid.

2-[(4-bromothiophen-3-yloxy)methyl]benzo[b]thiophene $^1$H-NMR (CDCl$_3$) δ 7.79-7.86 (1H, m), 7.72-7.79 (1H, m), 7.29-7.39 (3H, m), 7.20 (1H, d, J=3.5 Hz), 6.39 (1H, d, J=3.5 Hz), 5.34 (2H, d, J=0.8 Hz).

2-[(4-ethynylthiophen-3-yloxy)methyl]benzo[b]thiophene $^1$H-NMR (CDCl$_3$) δ 7.79-7.84 (1H, m), 7.73-7.77 (1H, m), 7.42 (1H, d, J=3.3 Hz), 7.29-7.39 (3H, m), 6.34 (1H, d, J=3.3 Hz), 5.35 (2H, d, J=0.9 Hz), 3.19 (1H, s).

3-{4-[4-(benzo[b]thiophen-2-ylmethoxy)thiophen-3-yl]-1H-1,2,3-triazol-1-yl}piperidine-2,6-dione $^1$H-NMR (DMSO-d$_6$) δ 11.11-11.30 (1H, brs), 8.28 (1H, s), 7.93-7.98 (1H, m), 7.91 (1H, d, J=3.4 Hz), 7.82-7.88 (1H, m), 7.58 (1H, d, J=0.3 Hz), 7.33-7.41 (2H, m), 6.96 (1H, d, J=3.4 Hz), 5.86 (1H, dd, J=5.0, 12.4 Hz), 5.52 (2H, s), 2.64-2.91 (3H, m), 2.29-2.40 (1H, m).

Example 48 (Compound 48)

3-[5-bromo-4-(thiophen-3-yl)-1H-1,2,3-triazol-1-yl]piperidine-2,6-dione

To a suspension of N-bromosuccinimide (1.19 g, 6.69 mmol) and silver nitrate (107.2 mg, 0.63 mmol) in acetone (30 mL) was added 3-ethynylthiophene (0.60 mL, 6.03 mmol), and the mixture was stirred in the dark at room temperature for 16.5 hr. The reaction mixture was diluted with hexane and washed with saturated brine and 1.0 M aqueous sodium thiosulfate. The organic layer was dried over anhydrous magnesium sulfate and concentrated to give 3-(bromoethynyl)thiophene mixture (1.21 g) as a brown oil. The obtained mixture (1.21 g) was dissolved in tetrahydrofuran (12 mL), 3-azidopiperidine-2,6-dione (synthesized by the method of Example 1 (1-1)) (0.97 g, 6.29 mmol), copper(II) acetate (53.6 mg, 0.30 mmol) and copper(I) iodide (56.1 mg, 0.29 mmol) were added, and the mixture was stirred under an argon atmosphere at 50° C. for 2 days. To the reaction mixture was added water (12 mL), and the precipitate was collected by filtration and washed with water and acetonitrile. The residue was recrystallized from dimethyl sulfoxide-water to give 3-[5-bromo-4-(thiophen-3-yl)-1H-1,2,3-triazol-1-yl]piperidine-2,6-dione (1.14 g, 55%) as a gray solid.

$^1$H-NMR (DMSO-d$_6$) δ 11.33 (1H, brs), 8.04 (1H, dd, J=1.3, 2.9 Hz), 7.75 (1H, dd, J=2.9, 5.0 Hz), 7.66 (1H, dd, J=1.3, 5.0 Hz), 5.86 (1H, dd, J=5.1, 12.6 Hz), 2.96 (1H, ddd, J=5.1, 13.1, 16.6 Hz), 2.83 (1H, dq, J=4.2, 12.7 Hz), 2.65-2.77 (1H, m), 2.37-2.46 (1H, m).

Example 49 (Compound 49)

3-[5-iodo-4-(4-methoxythiophen-3-yl)-1H-1,2,3-triazol-1-yl]piperidine-2,6-dione (49-1) To a solution of 3-ethynyl-4-methoxythiophene (synthesized by the method of Example 19) (136.5 mg, 0.99 mmol) in tetrahydrofuran (2.4 mL) were added N-iodomorpholine hydroiodide (420.2 mg, 1.23 mmol) and copper (I)iodide (10.2 mg, 0.05 mmol), and the mixture was stirred at room temperature for 26.5 hr. To the reaction mixture was added hexane, and the mixture was washed with saturated brine and 1.0 M aqueous sodium thiosulfate. The organic layer was dried over anhydrous magnesium sulfate and concentrated to give 3-(iodoethynyl)-4-methoxythiophene (232.2 mg, 89%) as a red-brown oil.

$^1$H-NMR (CDCl$_3$) δ 7.38 (1H, d, J=3.3 Hz), 6.19 (1H, d, J=3.3 Hz), 3.86 (3H, s).

(49-2) To a solution of 3-(iodoethynyl)-4-methoxythiophene (232.2 mg, 0.88 mmol) in tetrahydrofuran (1.8 mL) were added 3-azidopiperidine-2,6-dione (145.6 mg, 0.94 mmol), tris[(1-benzyl-1H-1,2,3-triazol-4-yl)methyl]amine (25.4 mg, 0.05 mmol) and copper(I) iodide (9.2 mg, 0.05 mmol), and the mixture was stirred at room temperature for 4 days. The reaction mixture was concentrated, and the concentrated residue was purified by column chromatography (hexane/ethyl acetate) to give a pale-green solid (287.0 mg). The obtained pale-green solid was washed with methanol and ethyl acetate, and then chloroform and methanol, and dissolved in dimethyl sulfoxide (1 mL). Water (0.8 mL) was added and the precipitate was collected by filtration. The residue was washed with methanol and ethyl acetate to give 3-[5-iodo-4-(4-methoxythiophen-3-yl)-1H-1,2,3-triazol-1-yl]piperidine-2,6-dione (157.5 mg, 43%) as a white solid.

$^1$H-NMR (DMSO-d$_6$) δ 11.15-11.42 (1H, brs), 7.66 (1H, d, J=3.3 Hz), 6.75 (1H, d, J=3.3 Hz), 5.77 (1H, dd, J=5.1, 12.4 Hz), 3.78 (3H, s), 2.98 (1H, ddd, J=5.3, 12.9, 16.8 Hz), 2.74-2.88 (1H, m), 2.70 (1H, ddd, J=2.8, 4.0, 16.8 Hz), 2.30-2.43 (1H, m).

Example 50: Human TNF-α Production Suppression Test

Peripheral blood of a healthy adult was collected in a vacuum blood collection tube (Terumo, containing EDTA/2Na), and then diluted two-fold with an equal volume of OTSUKA NORMAL SALINE (Otsuka Pharmaceutical Co., Ltd.). The diluted blood was mixed with Lymphoprep (AXIS-SHIELD) in half the volume of the diluted blood, dispensed into a 15 mL conical tube, and centrifuged at room temperature for 20 min (2,100 rpm). The mononuclear cells accumulated at the interface between Lymphoprep and plasma was transferred to a 50 mL conical tube, diluted with OTSUKA NORMAL SALINE, and the mononuclear cells suspension was centrifuged at room temperature for 10 min (1,150 rpm) and then the supernatant was removed. The mononuclear cells fraction obtained as a precipitate was suspended in an appropriate amount of 10% fetal calf serum (Thermo Fisher Scientific)-containing RPMI1640 medium (Thermo Fisher Scientific, hereinafter abbreviated as medium A), and diluted as appropriate with 0.4% trypan blue solution (Sigma-Aldrich Co. LLC.). The number of viable cells was counted with a hemocytometer (ERMA INC.). It was diluted with medium A such that the value obtained was 5×10$^5$ cells/mL. On the other hand, 75 μL of medium A, 5 μL of 0.4 mg/mL test compound solution (DMSO solution 10-fold diluted with medium A), and 20 μL of 10 μg/mL lipopolysaccharide (Sigma-Aldrich Co. LLC.) solution (diluted with medium A) were each added in advance to the same well of a Falcon 96-well flat bottom plate (Corning Incorporated), and the above-mentioned cell suspension was dispensed at 0.1 mL/well. 5 μL of DMSO diluted 10-fold with medium A was added to the control well instead of the compound solution. After culturing at 37° C. in a 5% CO$_2$ stream for 24 hr, the culture solution was centrifuged at 4° C., 1,000 rpm for 3 min and the supernatant was recovered. The content of TNF-α in the supernatant was measured using an ELISA kit (Peprotech) according to a conventional method. The amount of TNF-α produced in the well containing the test compound was determined with the amount of TNF-α produced in the control well as 100, and the suppression rate was calculated for each test. As shown in Table 1, the compound of the present invention showed a strong TNF-α production suppressive activity at 10 μg/mL.

TABLE 1

Table 1 TNF-α production suppressive rate (%)

| | |
|---|---|
| compound 1 | 90 |
| compound 2 | 98 |
| compound 3 | 59 |
| compound 4 | 67 |
| compound 5 | 71 |
| compound 6 | 67 |
| compound 7 | 73 |
| compound 8 | 64 |
| compound 9 | 41 |
| compound 10 | 50 |
| compound 11 | 81 |
| compound 12 | 84 |
| compound 13 | 35 |
| compound 14 | 75 |
| compound 15 | 85 |
| compound 16 | 100 |
| compound 17 | 92 |
| compound 18 | 100 |
| compound 19 | 83 |
| compound 20 | 87 |
| compound 21 | 30 |
| compound 22 | 48 |
| compound 23 | 62 |
| compound 24 | 75 |
| compound 25 | 49 |
| compound 26 | 83 |
| compound 27 | 39 |
| compound 28 | 37 |
| compound 29 | 57 |
| compound 30 | 79 |
| compound 31' | 82 |
| compound 32 | 100 |
| compound 33 | 100 |
| compound 34 | 97 |
| compound 35 | 70 |
| compound 36 | 98 |
| compound 37 | 81 |
| compound 38 | 89 |
| compound 39 | 81 |
| compound 40 | 86 |
| compound 41 | 93 |
| compound 42 | 96 |
| compound 43 | 87 |
| compound 44 | 79 |
| compound 45 | 76 |
| compound 46 | 80 |
| compound 47 | 63 |
| compound 48 | 51 |
| compound 49 | 79 |

(' suppressive rate at 3 μg/mL)

Example 51: Human Myeloma Cell Line MM.1S Proliferation Suppression Test

MM.1S cells (ATCC, CRL-2974) were suspended in 10% fetal calf serum (Thermo Fisher Scientific)-containing RPMI1640 medium (ATCC, hereinafter abbreviated as medium B), and diluted as appropriate with 0.4% trypan blue solution (Sigma-Aldrich Co. LLC.). The number of viable cells was counted with a hemocytometer (ERMA INC.). It was diluted with medium B such that the value obtained was 2×10$^5$ cells/mL. On the other hand, 50 μL of a solution obtained by diluting 4 mM DMSO solution of the test compound 200-fold with medium B was added to each well of a Falcon 96-well flat bottom plate (Corning Incorporated), and the above-mentioned cell suspension was dispensed at 50 μL/well (final concentration of test compound 10 μM). 50 μL of a solution obtained by diluting DMSO 200-fold with medium B was added to the control well. After culturing at 37° C. in a 5% CO$_2$ stream for 3 days, the cell proliferation activity was measured using WST-1 (DOJINDO LABORATORIES) or WST-8 Kit (KISHIDA CHEMICAL Co., Ltd.) and according to each instruction manual attached thereto. As shown in Table 2, the compound of the present invention showed obvious MM.1S cell proliferation suppressive activity.

Example 52: Human Diffuse Large B-Cell Lymphoma Cell Line Pfeiffer Proliferation Suppression Test Pfeiffer cells (ATCC, CRL-2632) were suspended in medium B, and diluted as appropriate with 0.4% trypan blue solution (Sigma-Aldrich Co. LLC.). The number of viable cells was counted with a hemocytometer (Funakoshi Co., Ltd.). A cell suspension obtained by diluting with medium B such that the value obtained was $1.3 \times 10^5$ cells/mL was dispensed into a Falcon 96 well flat bottom plate (Corning Incorporated) at 75 μL/well, and culture was started at 37° C. under 5% $CO_2$ stream. The next day, a solution obtained by diluting 4 mM DMSO solution of the test compound 100-fold with medium B was added by 25 μL to each well (final concentration of test compound 10 μM). 25 μL of a solution obtained by diluting DMSO 100-fold with medium B was added to the control well. After culturing at 37° C. in a 5% $CO_2$ stream for 3 days, the cell culture medium was uniformly suspended with a multi channel pipette, 14 μL per well was transferred into another new Falcon 96 well flat bottom plate. A solution obtained by diluting 4 mM DMSO solution of the same test compound as the first time 400-fold with medium B was added by 86 μL to a total amount of 100 μL (final concentration of test compound 10 μM). After culturing at 37° C. in a 5% $CO_2$ stream for 3 days, the cell proliferation activity was measured according to the instruction manual attached to WST-8 Kit (KISHIDA CHEMICAL Co., Ltd.). As shown in Table 2, the compound of the present invention showed obvious Pfeiffer cell proliferation suppressive activity.

Example 53: Human Mantle Cell Lymphoma Cell Line REC-1 Proliferation Suppression Test REC-1 cells (ATCC, CRL-3004) were suspended in medium B, and diluted as appropriate with 0.4% trypan blue solution (Sigma-Aldrich Co. LLC.). The number of viable cells was counted with a hemocytometer (Funakoshi Co., Ltd.). A cell suspension obtained by diluting with medium B such that the value obtained was $1.3 \times 10^5$ cells/mL was dispensed into a Falcon 96 well flat bottom plate (Corning Incorporated) at 75 μL/well, and culture was started at 37° C. under 5% $CO_2$ stream. The next day, a solution obtained by diluting 4 mM DMSO solution of the test compound 100-fold with medium B was added by 25 μL to each well (final concentration of test compound 10 μM). 25 μL of a solution obtained by diluting DMSO 100-fold with medium B was added to the control well. After culturing at 37° C. in a 5% $CO_2$ stream for 3 days, the cell proliferation activity was measured according to the instruction manual attached to WST-8 Kit (KISHIDA CHEMICAL Co., Ltd.). As shown in Table 2, the compound of the present invention showed obvious REC-1 cell proliferation suppressive activity.

Example 54: Human Burkitt Lymphoma Cell Line Daudi Proliferation Suppression Test Daudi cells (National Institutes of Biomedical Innovation, Health and Nutrition (NIBIOHN), JCRB9071) were suspended in medium B, and diluted as appropriate with 0.4% trypan blue solution (Sigma-Aldrich Co. LLC.). The number of viable cells was counted with a hemocytometer (ERMA INC.). A cell suspension obtained by diluting with medium B such that the value obtained was $1.3 \times 10^5$ cells/mL was dispensed into a Falcon 96 well flat bottom plate (Corning Incorporated) at 75 μL/well, and culture was started at 37° C. under 5% $CO_2$ stream. The next day, a solution obtained by diluting 4 mM DMSO solution of the test compound 100-fold with medium B was added by 25 μL to each well (final concentration of test compound 10 μM). 25 μL of a solution obtained by diluting DMSO 100-fold with medium B was added to the control well. After culturing at 37° C. in a 5% $CO_2$ stream for 3 days, the cell proliferation activity was measured according to the instruction manual attached to WST-8 Kit (KISHIDA CHEMICAL Co., Ltd.). As shown in Table 2, the compound of the present invention showed obvious Daudi cell proliferation suppressive activity.

Example 55: Human Acute Lymphoblastic Leukemia Cell Line Kasumi-7 Proliferation Suppression Test Kasumi-7 cells (NIBIOHN, JCRB1401) were suspended in 20% fetal calf serum (Thermo Fisher Scientific, Inc.)-containing RPMI1640 medium (ATCC, hereinafter abbreviated as medium C), and diluted as appropriate with 0.4% trypan blue solution (Sigma-Aldrich Co. LLC.). The number of viable cells was counted with a hemocytometer (Funakoshi Co., Ltd.). A cell suspension obtained by diluting with medium C such that the value obtained was $1.3 \times 10^5$ cells/mL was dispensed into a Falcon 96 well flat bottom plate (Corning Incorporated) at 75 μL/well, and culture was started at 37° C. under 5% $CO_2$ stream. The next day, a solution obtained by diluting 4 mM DMSO solution of the test compound 100-fold with medium C was added by 25 μL to each well (final concentration of test compound 10 μM). 25 μL of a solution obtained by diluting DMSO 100-fold with medium C was added to the control well. After culturing at 37° C. in a 5% $CO_2$ stream for 3 days, the cell proliferation activity was measured according to the instruction manual attached to WST-8 Kit (KISHIDA CHEMICAL Co., Ltd.). As shown in Table 2, the compound of the present invention showed obvious Kasumi-7 cell proliferation suppressive activity.

Example 56: Cytotoxicity Test Using Human Peripheral Blood Mononuclear Cells (PBMC)

Peripheral blood of a healthy adult was collected in a Venoject II vacuum blood collection tube (Terumo, containing EDTA/2Na), and then diluted two-fold with an equal volume of OTSUKA NORMAL SALINE (Otsuka Pharmaceutical Co., Ltd.). The diluted blood was mixed with Lymphoprep (AXIS-SHIELD) in half the volume of the diluted blood, dispensed into a 15 mL conical tube, and centrifuged at room temperature for 20 min (2,100 rpm). The mononuclear cells accumulated at the interface between Lymphoprep and plasma was transferred to a 50 mL conical tube, diluted with OTSUKA NORMAL SALINE, and the mononuclear cells suspension was centrifuged at room temperature for 10 min (1,150 rpm) and then the supernatant was removed. The mononuclear cells fraction obtained as a precipitate was suspended in an appropriate amount of medium A, and diluted as appropriate with 0.4% trypan blue solution (Sigma-Aldrich Co. LLC.). The number of viable cells was counted with a hemocytometer (ERMA INC.). It was diluted with medium A such that the value obtained was $5 \times 10^5$ cells/mL. On the other hand, 37.5 μL of medium A, 2.5 μL of 0.4 mg/mL test compound solution (DMSO solution 10-fold diluted with medium A), and 10 μL of 10 μg/mL lipopolysaccharide (Sigma-Aldrich Co. LLC.) solution (diluted with medium A) were each added in advance to the same well of a Falcon 96-well flat bottom plate (Corning Incorporated), and the above-mentioned cell suspension was dispensed at 50 μL/well (final concentration of test compound 10 μg/mL). 2.5 μL of DMSO diluted 10-fold with medium A was added to the control well instead of the compound solution. After culturing at 37° C. in a 5% $CO_2$ stream for 24 hr, the cell survival rate was measured using WST-1 (DOJINDO LABORATORIES) or WST-8 kit (KISHIDA CHEMICAL Co., Ltd.) and according to each instruction manual attached thereto. As shown in Table 2, the compound of the present invention did not show a strong cytotoxicity.

TABLE 2

Cell proliferation inhibitory activity

| compound | cell survival rate (% of control) | | | | | cell survival rate (% of control) |
|---|---|---|---|---|---|---|
| (10 μM) | MM.1S | Pfeiffer | REC-1 | Daudi | Kasumi-7 | PBMC* |
| 1 | 33 | 89 | 43 | 61 | 65 | 106 |
| 2 | 50 | 80 | 36 | 71 | 68 | 100 |
| 3 | 59 | 96 | 65 | 78 | 81 | 89 |
| 4 | 87 | 98 | 93 | 82 | 91 | 112 |
| 5 | 66 | 98 | 53 | 82 | 72 | 97 |
| 6 | 63 | 100 | 52 | 79 | 72 | 96 |
| 7 | 57 | 101 | 44 | 75 | 69 | 101 |
| 8 | 94 | 107 | 99 | 93 | 94 | 97 |
| 9 | 77 | 100 | 70 | 83 | 90 | 129 |
| 10 | 78 | 113 | 57 | 85 | 72 | 97 |
| 11 | 63 | 114 | 56 | 94 | 78 | 115 |
| 12 | 74 | 94 | 77 | 87 | 89 | 101 |
| 13 | 79 | 100 | 100 | 95 | 93 | 132 |
| 14 | 43 | 74 | 34 | 49 | 64 | 113 |
| 15 | 55 | 87 | 36 | 61 | 60 | 105 |
| 16 | 85 | 98 | 85 | 83 | 90 | 90 |
| 17 | 32 | 72 | 23 | 50 | 48 | 49 |
| 18 | 27 | 70 | 18 | 51 | 52 | 53 |
| 19 | 24 | 11 | 4 | 4 | 24 | 99 |
| 20 | 35 | 81 | 22 | 55 | 53 | 104 |
| 21 | 75 | 106 | 63 | 86 | 79 | 116 |
| 22 | 73 | 97 | 65 | 81 | 82 | 132 |
| 23 | 75 | 97 | 70 | 76 | 76 | 104 |
| 24 | 63 | 91 | 46 | 69 | 72 | 91 |
| 25 | 69 | 84 | 57 | 68 | 73 | 118 |
| 26 | 40 | 82 | 23 | 51 | 50 | 42 |
| 27 | 82 | 98 | 80 | 70 | 83 | 107 |
| 28 | 68 | 91 | 58 | 78 | 75 | 89 |
| 29 | 89 | 110 | 86 | 79 | 84 | 104 |
| 30 | 59 | 99 | 49 | 76 | 62 | 70 |
| 31 | 27 | 82 | 27 | 39 | 43 | 106** |
| 32 | 27 | 60 | 15 | 23 | 36 | 66 |
| 33 | 49 | 71 | 27 | 27 | 38 | 78 |
| 34 | 50 | 104 | 33 | 48 | 45 | 95 |
| 35 | 55 | 104 | 39 | 67 | 53 | 100 |
| 36 | 16 | 34 | 2 | 6 | 19 | 59 |
| 37 | 24 | 71 | 17 | 20 | 38 | 99 |
| 38 | 24 | 29 | 5 | 7 | 23 | 110 |
| 39 | 26 | 69 | 24 | 30 | 36 | 98 |
| 40 | 35 | 91 | 33 | 46 | 41 | 96 |
| 41 | 32 | 72 | 20 | 24 | 26 | 110 |
| 42 | 27 | 63 | 13 | 17 | 26 | 103 |
| 43 | 30 | 89 | 23 | 36 | 42 | 98 |
| 44 | 33 | 94 | 30 | 41 | 40 | 105 |
| 45 | 31 | 78 | 26 | 40 | 39 | 110 |
| 46 | 35 | 84 | 23 | 29 | 35 | 110 |
| 47 | 64 | 99 | 33 | 87 | 56 | 106 |
| 48 | 85 | 98 | 98 | 80 | 95 | 138 |
| 49 | 48 | 75 | 24 | 42 | 56 | 102 |
| Thalidomide | 79 | 104 | 94 | 81 | 96 | — |

*PBMC cell survival rate was measured at compound 10 μg/mL
**Changed to 3 μg/mL due to precipitation of compound in medium
*—: no data

INDUSTRIAL APPLICABILITY

The present invention provides novel thiophene derivatives having a TNF-α production suppressive activity and hematologic cancer cell proliferation inhibitory activity, and useful for the treatment of rheumatoid arthritis, Crohn's disease, ulcerative colitis and further, hematologic cancer, and a medicament containing the same. The present invention is useful in the field of pharmaceutical products.

This application is based on patent application No. 2018-010984 filed in Japan (filing date: Jan. 25, 2018) and patent application No. 2018-084202 filed in Japan (filing date: Apr. 25, 2018), the contents of which are encompassed in full herein.

The invention claimed is:

1. A compound represented by the following general formula (I):

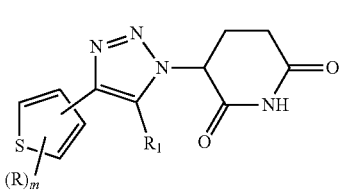

(I)

wherein:
$R_1$ is hydrogen or halogen;
R in the number of m are each independently halogen, C1-6 alkyl, C1-6 hydroxyalkyl, C1-6 alkoxy optionally having a substituent, C1-6 alkoxycarbonyl, or C1-6 alkylcarbonyl, or
two R on adjacent ring carbon atoms are bonded to each other to form, together with the two adjacent ring carbon atoms linked thereto, a 5- or 6-membered ring containing 1-2 oxygen atoms; and
m is 0, 1, 2 or 3,
or a salt thereof.

2. The compound according to claim 1 or a salt thereof, wherein the compound represented by the general formula (I) is a compound represented by the following general formula (IA) or (IB):

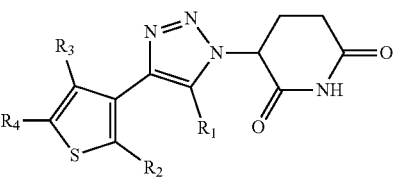

(IA)

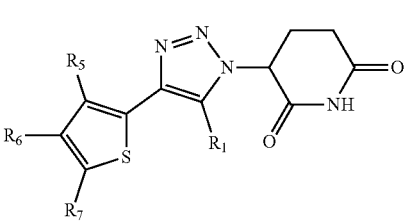

(IB)

wherein:
$R_1$ is hydrogen or halogen;
$R_2$ is hydrogen, halogen, C1-6 alkyl, C1-6 hydroxyalkyl, C1-6 alkoxy, C1-6 alkoxycarbonyl, or C1-6 alkylcarbonyl;
$R_3$ is hydrogen, halogen, C1-6 alkyl, or C1-6 alkoxy optionally having a substituent;
$R_4$ is hydrogen, halogen, C1-6 alkyl, C1-6 hydroxyalkyl, C1-6 alkoxy, C1-6 alkoxycarbonyl, or C1-6 alkylcarbonyl;

$R_5$ is hydrogen, halogen, C1-6 alkyl, C1-6 hydroxyalkyl, C1-6 alkoxy, C1-6 alkoxycarbonyl, or C1-6 alkylcarbonyl;

$R_6$ is hydrogen, halogen, C1-6 alkyl, C1-6 hydroxyalkyl, C1-6 alkoxy, C1-6 alkoxycarbonyl, or C1-6 alkylcarbonyl, or $R_5$ and $R_6$ are bonded to each other to form, together with a carbon atom linked thereto, a 5- or 6-membered ring containing 1-2 oxygen atoms; and $R_7$ is hydrogen, halogen, C1-6 alkyl, C1-6 hydroxyalkyl, C1-6 alkoxy, C1-6 alkoxycarbonyl, or C1-6 alkylcarbonyl.

3. The compound according to claim 2 or a salt thereof, wherein $R_1$ is hydrogen or halogen;

$R_2$ is hydrogen, halogen, or C1-6 alkoxy;

$R_3$ is hydrogen, halogen, C1-6 alkyl, or C1-6 alkoxy optionally having a substituent;

$R_4$ is hydrogen, halogen, C1-6 alkyl, C1-6 hydroxyalkyl, C1-6 alkoxy, or C1-6 alkoxycarbonyl;

$R_5$ and $R_6$ are each hydrogen, or $R_5$ and $R_6$ are bonded to each other to form, together with a carbon atom linked thereto, a 5- or 6-membered ring containing 1-2 oxygen atoms; and $R_7$ is hydrogen, halogen, C1-6 alkyl, or C1-6 alkylcarbonyl.

4. The compound according to claim 1, or a salt thereof, wherein the C1-6 alkoxy optionally having a substituent for R is C1-6 chain alkoxy, C3-6 cycloalkoxy, or alkoxy represented by the formula: —O—X—Y wherein:

X is a linear or branched chain C1-6 alkylene; and

Y is C3-6 cycloalkyl, or pyridine, naphthalene or benzothiophene, each of which optionally has a substituent, or a substituent represented by the general formula (II):

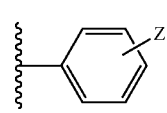
(II)

Z is hydrogen, C1-6 alkoxy, C1-6 alkoxymethyl, halogen, or a substituent represented by the following general formula (III), (IV), (V) or (VI):

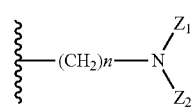
(III)

wherein $Z_1$ and $Z_2$ are each independently hydrogen or C1-6 alkyl, or $Z_1$ and $Z_2$ are bonded to each other to form, together with a nitrogen atom linked thereto, a 5- or 6-membered ring; and n is 1 or 2

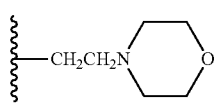
(IV)

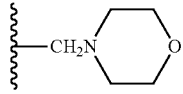
(V)

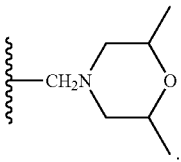
(VI)

5. The compound according to claim 4, wherein X is $CH_2$, $CH(CH_3)$ or $CH_2CH_2$, or a salt thereof.

6. The compound according to claim 2, or an acid addition salt thereof, wherein $R_1$ is hydrogen, iodo, bromo or chloro;

$R_2$ is hydrogen, bromo or methoxy;

$R_3$ is hydrogen, bromo, chloro, methyl, methoxy, ethoxy, propoxy, isopropoxy, butoxy, cyclopentyloxy, cyclopropylmethoxy, cyclopentylmethoxy, cyclohexylmethoxy, benzyloxy, 1-phenylethoxy, pyridin-2-ylmethoxy, pyridin-3-ylmethoxy, pyridin-4-ylmethoxy, benzo[b]thiophen-2-ylmethoxy, 4-methoxybenzyl oxy, 4-(methoxymethyl)benzyloxy, 4-chlorobenzyloxy, 4-(pyrrolidin-1-ylmethyl)benzyloxy, 4-(piperidin-1-ylmethyl)benzyloxy, 4-[(dimethylamino)methyl]benzyloxy, 4-(2-morpholinoethyl)benzyloxy, 2-(morpholinomethyl)benzyloxy, 3-(morpholinomethyl)benzyloxy, 4-(morpholinomethyl)benzyloxy or 4-{[(2S,6R)-2,6-dimethylmorpholino]methyl}benzyloxy;

$R_4$ is hydrogen, bromo, chloro, methyl, hydroxymethyl, methoxy, ethoxy or methoxycarbonyl;

$R_5$ and $R_6$ are each hydrogen, or $R_5$ and $R_6$ are bonded to each other to form, together with a carbon atom linked thereto, a 6-membered ring containing two oxygen atoms; and $R_7$ is hydrogen, chloro, bromo, methyl or acetyl.

7. The compound according to claim 1, or a salt thereof, wherein the compound or the salt is selected from 3-[4-(4-bromothiophen-3-yl)-1H-1,2,3-triazol-1-yl]piperidine-2,6-dione, 3-[4-(thiophen-3-yl)-1H-1,2,3-triazol-1-yl]piperidine-2,6-dione, 3-[4-(thiophen-2-yl)-1H-1,2,3-triazol-1-yl]piperidine-2,6-dione, 3-[5-chloro-4-(thiophen-3-yl)-1H-1,2,3-triazol-1-yl]piperidine-2,6-dione, 3-[4-(5-methylthiophen-2-yl)-1H-1,2,3-triazol-1-yl]piperidine-2,6-dione, 3-[4-(5-methylthiophen-3-yl)-1H-1,2,3-triazol-1-yl]piperidine-2,6-dione, 3-[4-(4-methylthiophen-3-yl)-1H-1,2,3-triazol-1-yl]piperidine-2,6-dione, 3-[4-(5-acetylthiophen-2-yl)-1H-1,2,3-triazol-1-yl]piperidine-2,6-dione, 3-{4-[5-(hydroxymethyl)thiophen-3-yl]-1H-1,2,3-triazol-1-yl}piperidine-2,6-dione, 3-[4-(2,3-dihydrothieno[3,4-b][1,4]dioxin-5-yl)-1H-1,2,3-triazol-1-yl]piperidine-2,6-dione, 3-[4-(5-chlorothiophen-2-yl)-1H-1,2,3-triazol-1-yl]piperidine-2,6-dione, 3-[4-(5-bromothiophen-2-yl)-1H-1,2,3-triazol-1-yl]piperidine-2,6-dione, 3-[4-(2,5-dibromothiophen-3-yl)-1H-1,2,3-triazol-1-yl]piperidine-2,6-dione,
3-[4-(4-chlorothiophen-3-yl)-1H-1,2,3-triazol-1-yl]piperidine-2,6-dione,
3-[4-(4-methoxy-5-methylthiophen-3-yl)-1H-1,2,3-triazol-1-yl]piperidine-2,6-dione,
methyl 4-[1-(2,6-dioxopiperidin-3-yl)-1H-1,2,3-triazol-4-yl]-3-methoxythiophene-2-carboxylate,
3-[4-(4-ethoxythiophen-3-yl)-1H-1,2,3-triazol-1-yl]piperidine-2,6-dione,
3-[4-(2-methoxythiophen-3-yl)-1H-1,2,3-triazol-1-yl]piperidine-2,6-dione,
3-[4-(4-methoxythiophen-3-yl)-1H-1,2,3-triazol-1-yl]piperidine-2,6-dione,
3-[4-(5-methoxythiophen-3-yl)-1H-1,2,3-triazol-1-yl]piperidine-2,6-dione,
3-[4-(4-propoxythiophen-3-yl)-1H-1,2,3-triazol-1-yl]piperidine-2,6-dione,
3-[4-(5-chloro-4-methoxythiophen-3-yl)-1H-1,2,3-triazol-1-yl]piperidine-2,6-dione,
3-[4-(5-bromo-4-methoxythiophen-3-yl)-1H-1,2,3-triazol-1-yl]piperidine-2,6-dione,
3-[4-(5-ethoxythiophen-3-yl)-1H-1,2,3-triazol-1-yl]piperidine-2,6-dione,
3-[4-(4-butoxythiophen-3-yl)-1H-1,2,3-triazol-1-yl]piperidine-2,6-dione,
3-[4-(4-isopropoxythiophen-3-yl)-1H-1,2,3-triazol-1-yl]piperidine-2,6-dione,
3-{4-[4-(cyclopentyloxy)thiophen-3-yl]-1H-1,2,3-triazol-1-yl}piperidine-2,6-dione,
3-{4-[4-(cyclopropylmethoxy)thiophen-3-yl]-1H-1,2,3-triazol-1-yl}piperidine-2,6-dione,
3-{4-[4-(cyclopentylmethoxy)thiophen-3-yl]-1H-1,2,3-triazol-1-yl}piperidine-2,6-dione,
3-{4-[4-(cyclohexylmethoxy)thiophen-3-yl]-1H-1,2,3-triazol-1-yl}piperidine-2,6-dione,
3-{4-[4-(4-methoxybenzyloxy)thiophen-3-yl]-1H-1,2,3-triazol-1-yl}piperidine-2,6-dione,
3-{4-[4-(benzyloxy)thiophen-3-yl]-1H-1,2,3-triazol-1-yl}piperidine-2,6-dione,
3-{4-[4-(pyridin-4-ylmethoxy)thiophen-3-yl]-1H-1,2,3-triazol-1-yl}piperidine-2,6-dione,
3-{4-[4-(pyridin-2-ylmethoxy)thiophen-3-yl]-1H-1,2,3-triazol-1-yl}piperidine-2,6-dione,
3-{4-[4-(pyridin-3-ylmethoxy)thiophen-3-yl]-1H-1,2,3-triazol-1-yl}piperidine-2,6-dione,
3-(4-{4-[4-(morpholinomethyl)benzyloxy]thiophen-3-yl}-1H-1,2,3-triazol-1-yl)piperidine-2,6-dione,
3-(4-{4-[4-(methoxymethyl)benzyloxy]thiophen-3-yl}-1H-1,2,3-triazol-1-yl)piperidine-2,6-dione,
3-{4-[4-(4-{[(2S,6R)-2,6-dimethylmorpholino]methyl}benzyloxy)thiophen-3-yl]-1H-1,2,3-triazol-1-yl}piperidine-2,6-dione,
3-(4-{4-[3-(morpholinomethyl)benzyloxy]thiophen-3-yl}-1H-1,2,3-triazol-1-yl)piperidine-2,6-dione,
3-(4-{4-[2-(morpholinomethyl)benzyloxy]thiophen-3-yl}-1H-1,2,3-triazol-1-yl)piperidine-2,6-dione,
3-(4-{4-[4-(pyrrolidin-1-ylmethyl)benzyloxy]thiophen-3-yl}-1H-1,2,3-triazol-1-yl)piperidine-2,6-dione,
3-(4-{4-[4-(piperidin-1-ylmethyl)benzyloxy]thiophen-3-yl}-1H-1,2,3-triazol-1-yl)piperidine-2,6-dione,
3-{4-[4-(4-chlorobenzyloxy)thiophen-3-yl]-1H-1,2,3-triazol-1-yl}piperidine-2,6-dione,
3-{4-[4-(1-phenylethoxy)thiophen-3-yl]-1H-1,2,3-triazol-1-yl}piperidine-2,6-dione,
3-(4-{4-[4-(2-morpholinoethyl)benzyloxy]thiophen-3-yl}-1H-1,2,3-triazol-1-yl)piperidine-2,6-dione,
3-[4-(4-{4-[(dimethylamino)methyl]benzyloxy}thiophen-3-yl)-1H-1,2,3-triazol-1-yl]piperidine-2,6-dione,
3-{4-[4-(benzo[b]thiophen-2-ylmethoxy)thiophen-3-yl]-1H-1,2,3-triazol-1-yl}piperidine-2,6-dione,
3-[5-bromo-4-(thiophen-3-yl)-1H-1,2,3-triazol-1-yl]piperidine-2,6-dione, and
3-[5-iodo-4-(4-methoxythiophen-3-yl)-1H-1,2,3-triazol-1-yl]piperidine-2,6-dione, and acid addition salts thereof.

8. The compound according to claim 2 or a salt thereof, wherein the compound represented by the general formula (I) is a compound represented by the following general formula (IA):

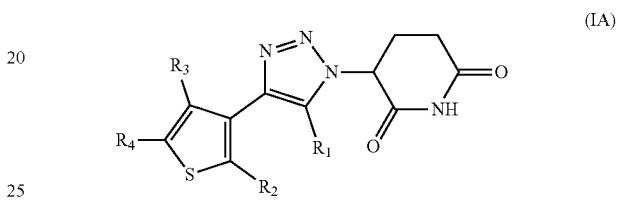

wherein:

$R_1$ is hydrogen;

$R_2$ is hydrogen;

$R_3$ is hydrogen or C1-6 alkoxy optionally having a substituent; and $R_4$ is hydrogen, C1-6 alkoxy or halogen.

9. The compound according to claim 8 or a salt thereof, wherein $R_3$ is hydrogen, C1-6 chain alkoxy, or alkoxy represented by the formula: —O—X—Y wherein:

X is linear C1-6 alkylene; and

Y is benzothiophene, pyridine or a substituent represented by the general formula (II):

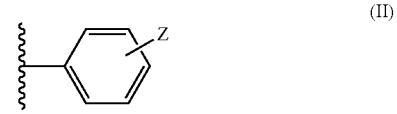

wherein Z is hydrogen, C1-6 chain alkoxymethyl, or a substituent represented by the following general formula (III), (IV), (V) or (VI):

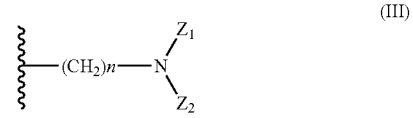

wherein $Z_1$ and $Z_2$ are each C1-6 chain alkyl, or $Z_1$ and $Z_2$ are bonded to each other to form, together with a nitrogen atom linked thereto, a 5- or 6-membered ring; and n is 1 or 2;

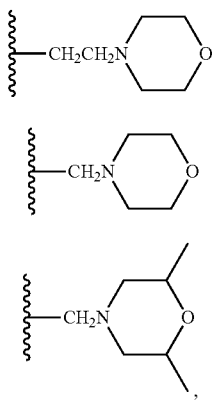

and
R₄ is hydrogen.

10. The compound according to claim 1, or a salt thereof, wherein the compound or the salt is selected from
3-[4-(5-methoxythiophen-3-yl)-1H-1,2,3-triazol-1-yl]piperidine-2,6-dione,
3-[4-(5-bromo-4-methoxythiophen-3-yl)-1H-1,2,3-triazol-1-yl]piperidine-2,6-dione,
3-[4-(4-methoxythiophen-3-yl)-1H-1,2,3-triazol-1-yl]piperidine-2,6-dione,
3-{4-[4-(benzyloxy)thiophen-3-yl]-1H-1,2,3-triazol-1-yl}piperidine-2,6-dione,
3-(4-{4-[4-(methoxymethyl)benzyloxy]thiophen-3-yl}-1H-1,2,3-triazol-1-yl)piperidine-2,6-dione,
3-{4-[4-(4-{[(2S,6R)-2,6-dimethylmorpholino] methyl}benzyloxy)thiophen-3-yl]-1H-1,2,3-triazol-1-yl}piperidine-2,6-dione,
3-(4-{4-[4-(pyrrolidin-1-ylmethyl)benzyloxy]thiophen-3-yl}-1H-1,2,3-triazol-1-yl)piperidine-2,6-dione,
3-(4-{4-[4-(piperidin-1-ylmethyl)benzyloxy]thiophen-3-yl}-1H-1,2,3-triazol-1-yl)piperidine-2,6-dione,
3-(4-{4-[4-(2-morpholinoethyl)benzyloxy]thiophen-3-yl}-1H-1,2,3-triazol-1-yl)piperidine-2,6-dione,
3-[4-(4-{4-[(dimethylamino)methyl]benzyloxy}thiophen-3-yl)-1H-1,2,3-triazol-1-yl]piperidine-2,6-dione, and
3-{4-[4-(benzo[b]thiophen-2-ylmethoxy)thiophen-3-yl]-1H-1,2,3-triazol-1-yl}piperidine-2,6-dione and
acid addition salts thereof.

11. The compound according to claim 1, or a salt thereof, wherein the compound or the salt is selected from
3-[4-(5-methoxythiophen-3-yl)-1H-1,2,3-triazol-1-yl]piperidine-2,6-dione,
3-[4-(4-methoxythiophen-3-yl)-1H-1,2,3-triazol-1-yl]piperidine-2,6-dione,
3-(4-{4-[4-(methoxymethyl)benzyloxy]thiophen-3-yl}-1H-1,2,3-triazol-1-yl)piperidine-2,6-dione,
3-{4-[4-(4-{[(2S,6R)-2,6-dimethylmorpholino] methyl}benzyloxy)thiophen-3-yl]-1H-1,2,3-triazol-1-yl}piperidine-2,6-dione, and
3-(4-{4-[4-(piperidin-1-ylmethyl)benzyloxy]thiophen-3-yl}-1H-1,2,3-triazol-1-yl)piperidine-2,6-dione, and
acid addition salts thereof.

12. The compound according to claim 1 or a salt thereof for use in the treatment of an inflammatory disease, an autoimmune disease, or a hematologic cancer.

13. A medicament comprising the compound according to claim 1 or a salt thereof as an active ingredient.

14. The medicament according to claim 13, wherein the medicament is a TNF-α production suppressor.

15. The medicament according to claim 13, wherein the medicament is a therapeutic agent for an inflammatory disease, an autoimmune disease, or a hematologic cancer.

16. The medicament according to claim 15, wherein the autoimmune disease is rheumatoid arthritis, Crohn's disease or ulcerative colitis.

17. The medicament according to claim 15, wherein the hematologic cancer is leukemia, malignant lymphoma, or multiple myeloma.

18. The medicament according to claim 15, wherein the hematologic cancer is multiple myeloma.

19. The medicament according to claim 15, wherein the hematologic cancer is malignant lymphoma.

20. The medicament according to claim 15, wherein the hematologic cancer is leukemia.

21. The medicament according to claim 17, wherein the malignant lymphoma is non-Hodgkin's lymphoma.

22. The medicament according to claim 21, wherein the non-Hodgkin's lymphoma is precursor lymphoid neoplasms or mature B-cell neoplasms.

23. A pharmaceutical composition comprising the compound according to claim 1 or a salt thereof as an active ingredient together with a pharmaceutically acceptable carrier.

24. A method for suppressing TNF-α production in a mammal, comprising administering an effective amount of the compound according to claim 1 or a salt thereof to the mammal.

25. A method for treating an inflammatory disease, an autoimmune disease, or a hematologic cancer, comprising administering a therapeutically effective amount of the compound according to claim 1 or a salt thereof to a mammal in need of the administration thereof.

* * * * *